United States Patent
Panitch et al.

(10) Patent No.: US 11,612,663 B2
(45) Date of Patent: Mar. 28, 2023

(54) PROTEOGLYCAN MIMETICS FOR ENHANCED WOUND HEALING, ANGIOGENESIS, AND VASCULAR REPAIR

(71) Applicants: The Regents of the University of California, Oakland, CA (US); Purdue Research Foundation, West Lafayette, IN (US)

(72) Inventors: Alyssa Panitch, Oakland, CA (US); Emily Michelle Misnick, Oakland, CA (US); Jenny B. Lin, Oakland, CA (US); Kit S. Lam, Davis, CA (US); Ruiwu Liu, Oakland, CA (US); Dake Hao, Oakland, CA (US); Aijun Wang, Sacramento, CA (US)

(73) Assignees: The Regents of the University of California, Oakland, CA (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/062,300

(22) Filed: Oct. 2, 2020

(65) Prior Publication Data
US 2021/0093728 A1   Apr. 1, 2021

Related U.S. Application Data

(63) Continuation of application No. PCT/US2019/026141, filed on Apr. 5, 2019.

(60) Provisional application No. 62/653,329, filed on Apr. 5, 2018.

(51) Int. Cl.
| | |
|---|---|
| A61K 38/00 | (2006.01) |
| A61K 47/61 | (2017.01) |
| A61K 47/64 | (2017.01) |
| A61K 47/60 | (2017.01) |
| A61P 9/00 | (2006.01) |
| C07K 7/06 | (2006.01) |
| C07K 7/08 | (2006.01) |

(52) U.S. Cl.
CPC .............. *A61K 47/61* (2017.08); *A61K 47/60* (2017.08); *A61K 47/64* (2017.08); *A61P 9/00* (2018.01); *C07K 7/06* (2013.01); *C07K 7/08* (2013.01); *A61K 38/00* (2013.01)

(58) Field of Classification Search
None
See application file for complete search history.

(56) References Cited

U.S. PATENT DOCUMENTS

| | | |
|---|---|---|
| 7,556,925 B2 | 7/2009 | Koide et al. |
| 2009/0305994 A1 | 12/2009 | D'Andrea et al. |
| 2013/0101628 A1 | 4/2013 | Webber et al. |
| 2016/0017000 A1 | 1/2016 | Lam et al. |
| 2016/0052994 A1 | 2/2016 | Sekiguchi et al. |
| 2016/0166654 A1 | 6/2016 | Paderi et al. |

FOREIGN PATENT DOCUMENTS

| | | | |
|---|---|---|---|
| WO | 2016/061145 | * | 4/2016 |
| WO | 2016/065083 A1 | | 4/2016 |
| WO | 2019/195780 A1 | | 10/2019 |

OTHER PUBLICATIONS

Campbell, I.D., et al Integrin Structure, Activation, and Interactions, Cold Spring Harb Perspect Biol 2011; 3, pp. 1-14 (Year: 2011).*

* cited by examiner

*Primary Examiner* — Thomas S Heard
(74) *Attorney, Agent, or Firm* — Kilpatrick Townsend & Stockton LLP

(57) ABSTRACT

The present disclosure provides pro-angiogenic proteoglycan mimetics that can provide a provisional, pro-angiogenic scaffold to support tissue regeneration while limiting systemic exposure to VEGF activity. These mimetics can protect a collagen matrix from rapid degradation, and in conjunction with EPCs promote angiogenesis in order to accelerate ischemic wound healing. For example, the provided compounds can be delivered from the end of a catheter following balloon angioplasty to coat the collagen exposed areas, prevent platelet binding and thrombosis, support capture of EPCs from blood to facilitate reendothelialization, and reduce late-lumen loss (neointimal hyperplasia).

17 Claims, 36 Drawing Sheets
Specification includes a Sequence Listing.

Vascularization score indicated in upper right corner

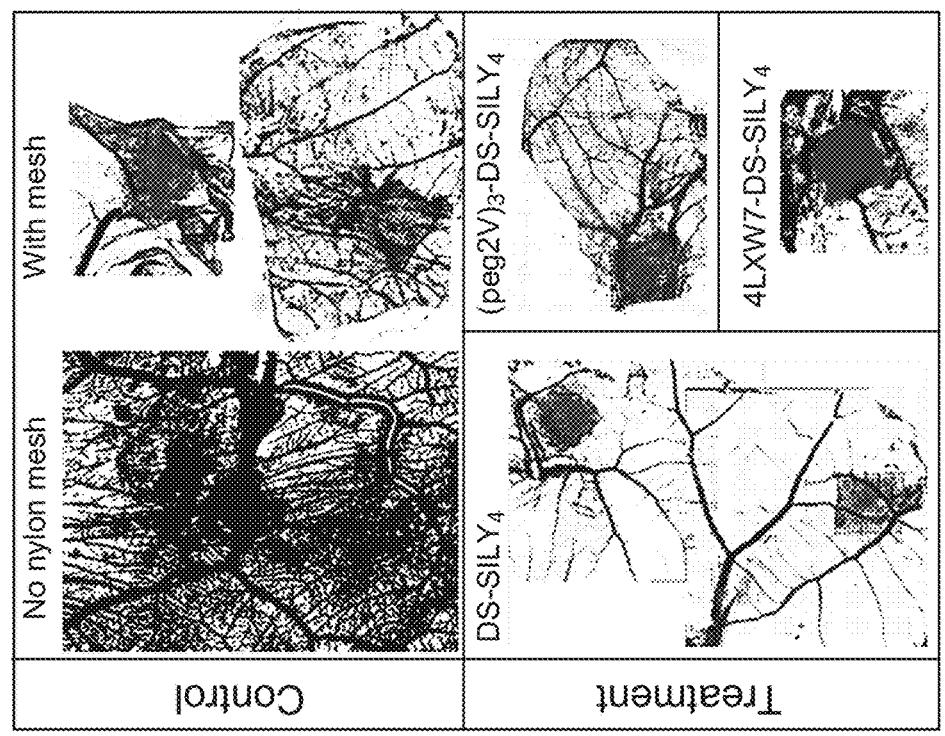
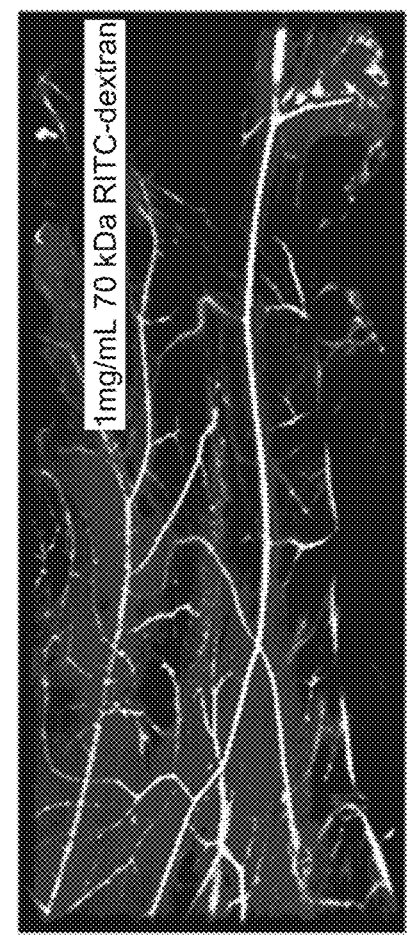
FIG. 28

FIG. 31
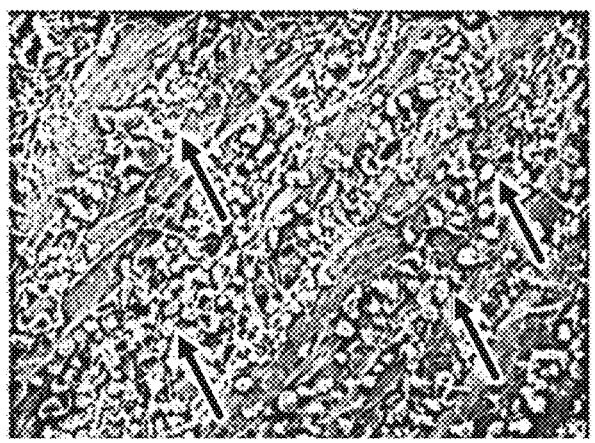 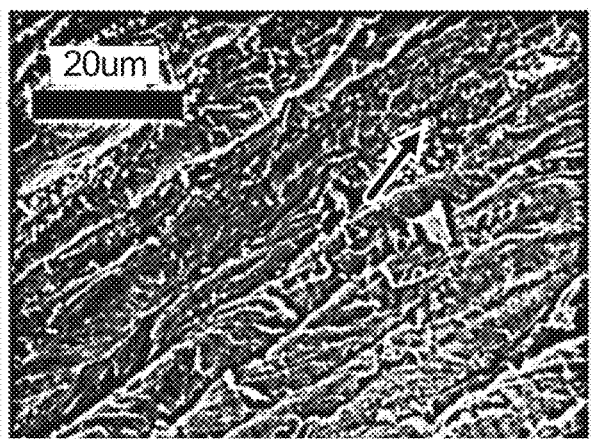
High platelet deposition on ballooned artery (arrows)
Scarce platelet deposition observed with DS-SILY
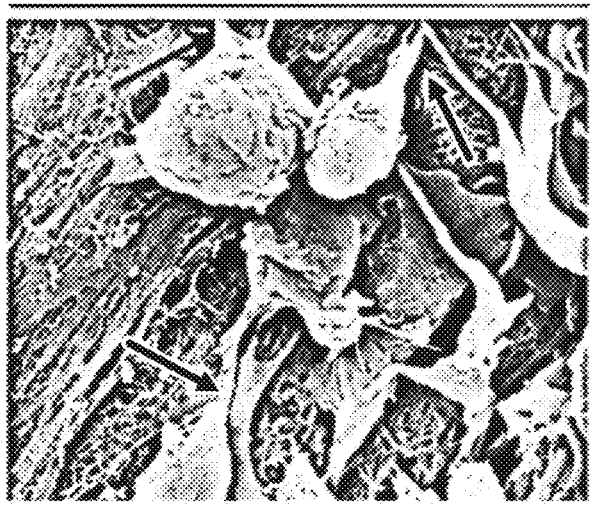 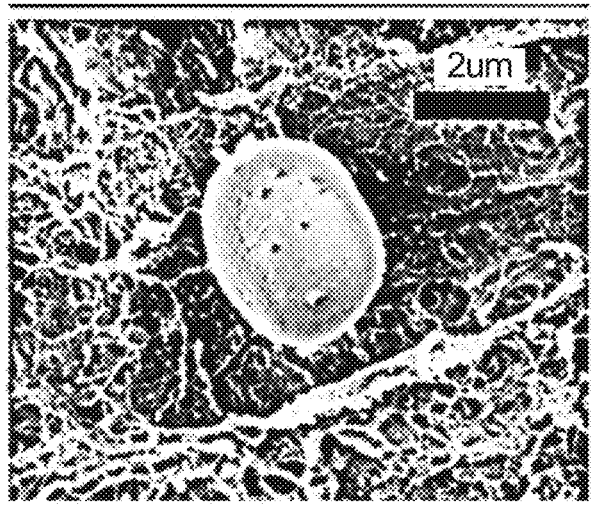
Activated platelets with numerous projections (arrows)
Rounding indicates platelets not activated

FIG. 32
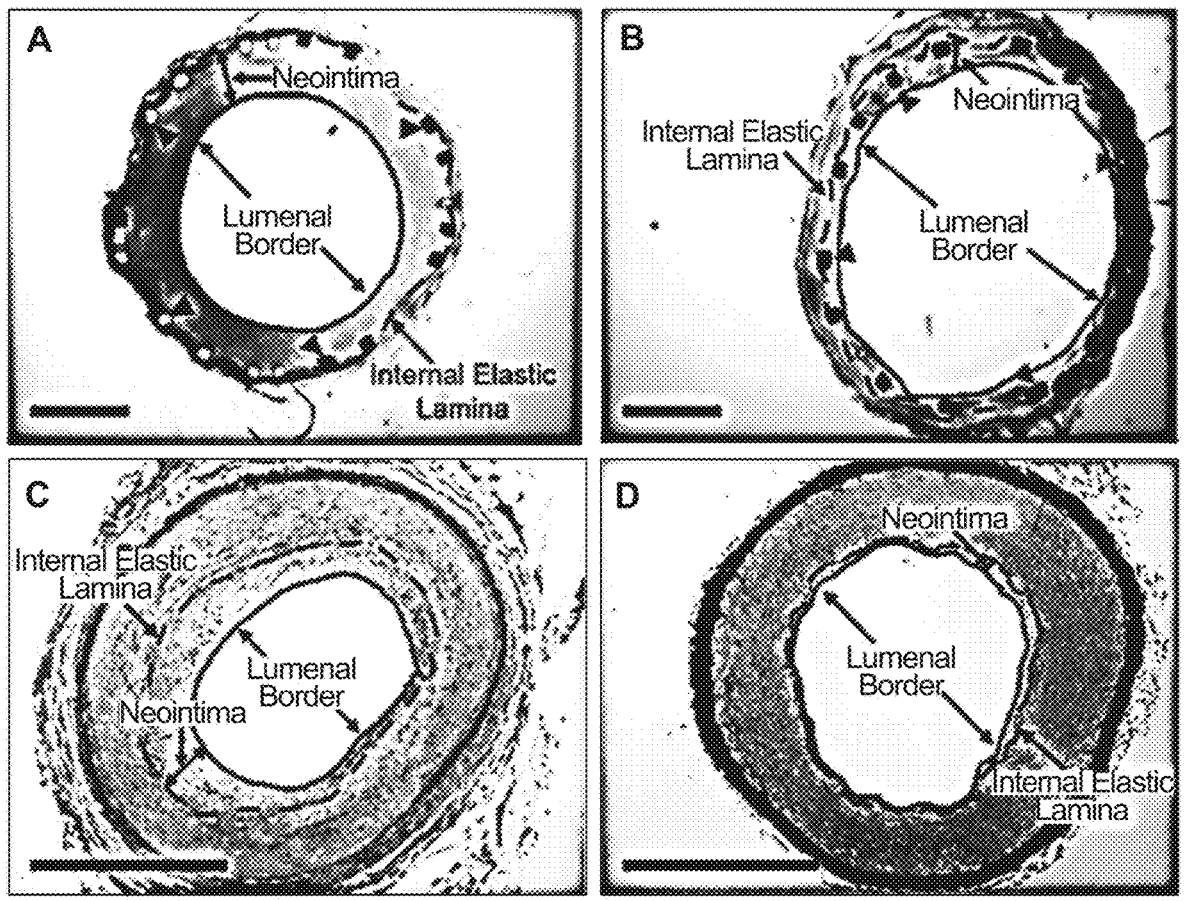
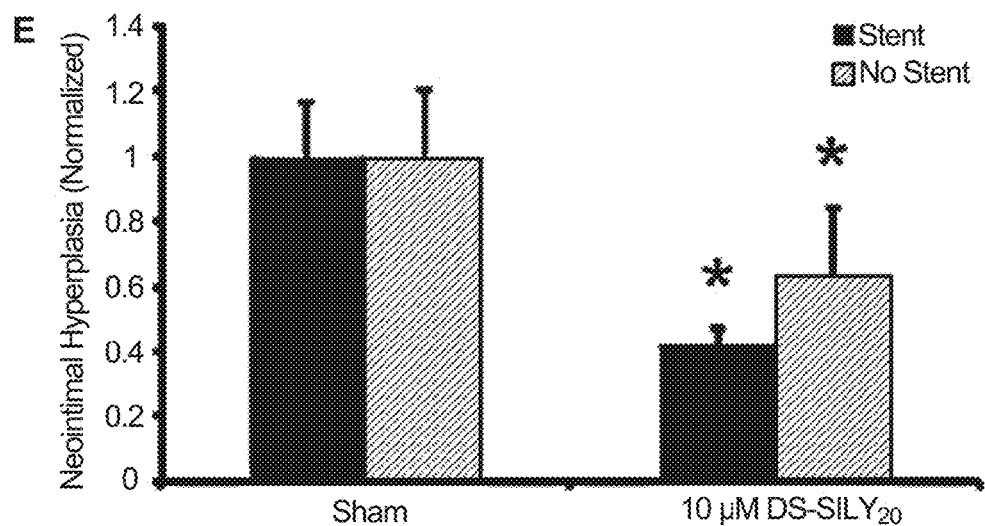

FIG. 33
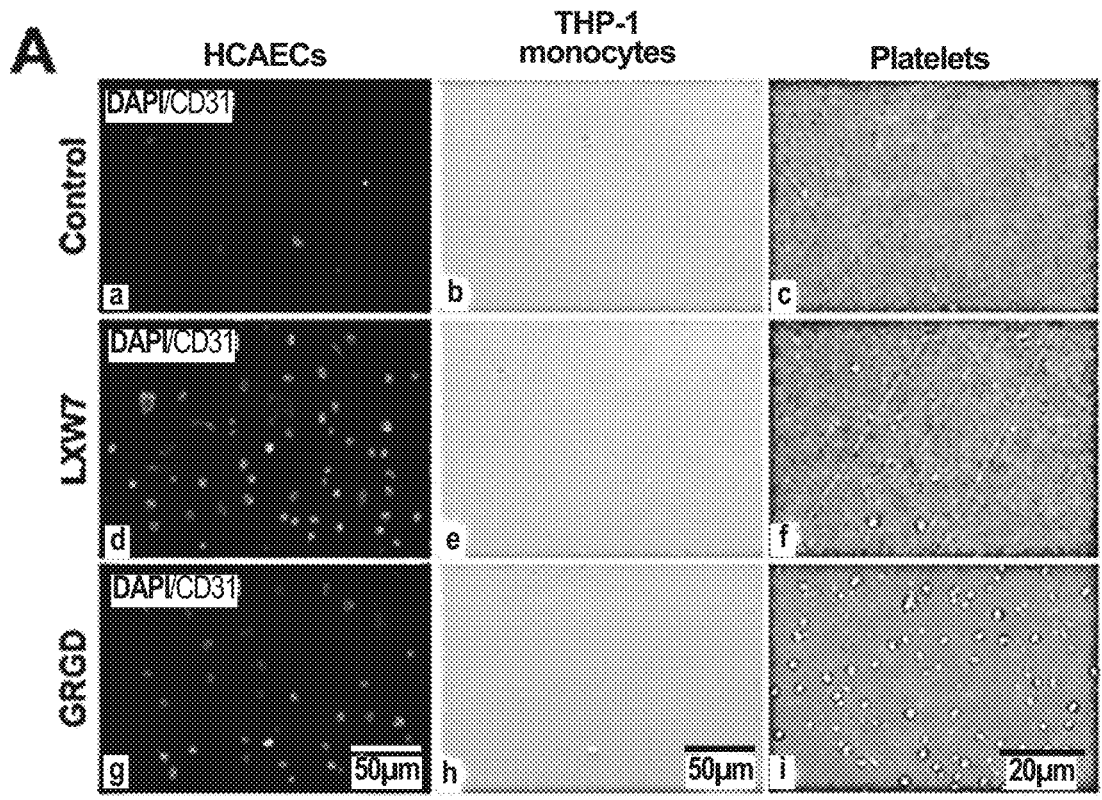
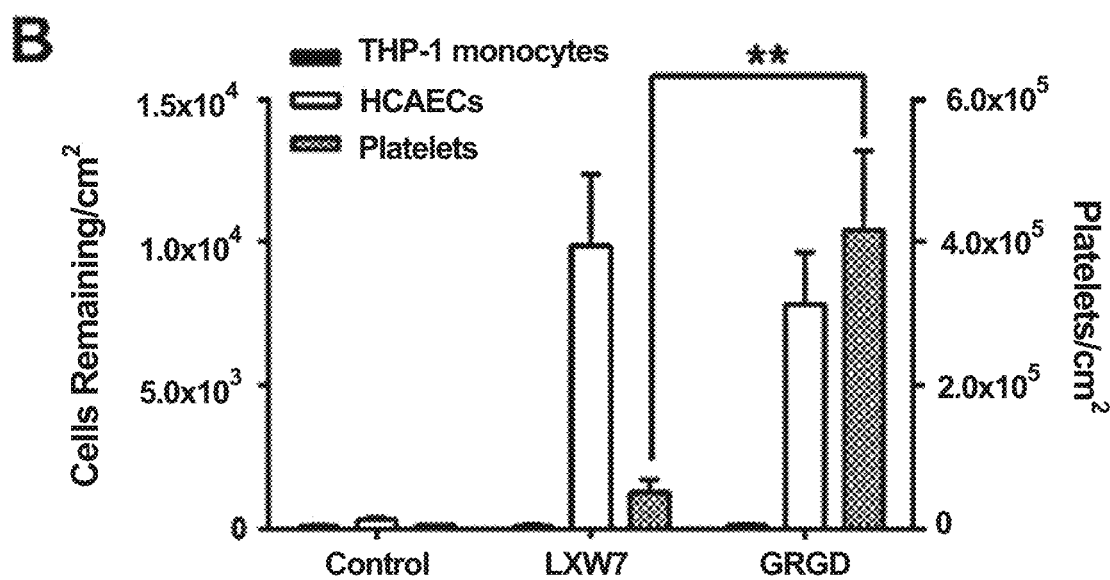

SEQUENCE LISTING

```
<160> NUMBER OF SEQ ID NOS: 8

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Ala Asn Ala Ala Leu Lys Ala Gly Glu Leu Tyr Lys Ser Ile
1               5                   10                  15

Leu Tyr

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Arg Gly Asp
1

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Leu Thr Trp Gln Glu Leu Tyr Gln Leu Lys Tyr Lys Gly Ile
1               5                   10                  15

<210> SEQ ID NO 4
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Lys Leu Thr Trp Gln Glu Leu Tyr Gln Leu Lys Tyr Lys Gly Ile Gly
1               5                   10                  15

Ser Gly

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Thr Trp Gln Glu Leu Tyr Gln Leu Lys Tyr Lys Gly Ile
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Ala Asn Ala Ala Leu Lys Ala Gly Glu Leu Tyr Lys Ser Ile
1               5                   10                  15

Leu Tyr Gly Ser Gly
            20

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Lys Glu Lys Glu Lys Glu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Glu Lys Glu Lys Glu Lys Glu
1               5
```

PROTEOGLYCAN MIMETICS FOR ENHANCED WOUND HEALING, ANGIOGENESIS, AND VASCULAR REPAIR

CROSS-REFERENCE TO RELATED APPLICATIONS

This application is a continuation of International Patent Application No. PCT/US2019/026141, filed Apr. 5, 2019, which claims priority to U.S. Provisional Patent Application No. 62/653,329, filed Apr. 5, 2018, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. DK101001 awarded by the National Institutes of Health (NIH). The Government has certain rights in the invention.

BACKGROUND

According to the Centers for Disease Control and Prevention (CDC) 2014 National Diabetes Statistics Report, between 15-25% of the approximately 29 million diabetic Americans develop serious foot ulcers. Approximately 65% of these ulcers have ischemic pathology and become chronic wounds due to impaired healing (Armstrong et al. (2011) J. Diabetes Sci. Technol. 5:1591). To improve healing of these chronic ischemic ulcers, researchers have sought to increase angiogenesis at the wound site using angiogenic growth factors. One key angiogenic mediator is the vascular endothelial growth factor (VEGF), which functions by improving the formation of granulation tissue, a loose fibrovascular tissue, during the early stages of the healing response. For example, in ischemic wounds, exogenous VEGF is known to increase granulation tissue formation up to 150% (Corral et al. (1999) Arch. Surg. 134:200). However, the clinical success of such growth factor therapies for chronic wounds has been limited largely due to the overexpression of matrix metalloproteases (MMPs) that can degrade or inactivate the growth factors in the wound environment (Fang and Galiano (2008) Biol. Targets Ther. 2:1). Excess MMPs can also promote the degradation of newly formed granulation tissue, thus counteracting healing. Furthermore, non-targeted angiogenic growth factor therapies are not restricted to the wound site, and can potentially diffuse into systemic circulation and cause malignancies.

Coronary atherosclerosis is currently the leading cause of death in society. Moreover, atherosclerotic conditions in an individual can be greatly exacerbated by the presence of risk factors such as metabolic syndrome ("pre-diabetes"), which itself often progresses to full-blown type-2 diabetes. Percutaneous coronary intervention (PCI) procedures are commonly performed in coronary arteries to open atherosclerotic or occluded vessels which would otherwise lead to ischemia if left untreated. PCI treatment involves threading a balloon catheter to the occluded vessel, whereupon the balloon is deployed to widen the vessel. A typical consequence of this procedure is damage to the vessel wall at the site of balloon deployment. The layer of endothelial cells (ECs) covering the internal lumen of the vessel can be stripped, and the underlying collagenous connective tissue can become exposed, initiating coagulation and inflammatory cascades of the body of the patient under treatment. These cascade responses within the patient's body in turn trigger thrombus formation, inflammation, smooth muscle cell (SMC) proliferation and migration, and extracellular matrix deposition. Together these effects can negatively impact both the safety and efficacy of the procedure. Left untreated, the lesions of atherosclerosis result in coronary arterial stenosis (narrowing) or blockage and consequent disruption of blood flow, culminating in myocardial infarction (heart attack) and death.

When conventional balloon angioplasty alone is used to open blocked vessels, in greater than 50% of cases the reopened artery closed again due to restenosis after the angioplasty. As a result, the patient with restenosis, or overgrowth of SMCs, often will require a second angioplasty or emergency bypass graft surgery. In part to address these complications, metallic coronary stents (wire meshes) were developed and introduced in 1993. While these stents have been effective in preventing abrupt artery closure due to vasoconstriction, serious injury to the blood vessels continue to occur, causing neointimal proliferation and leading to in-stent restenosis and the need for revascularization in approximately 20% of patients. This overgrowth of SMCs after surgery is similar to scar tissue formation in response to injury.

The problem of in-stent restenosis has been somewhat reduced by the introduction of drug-eluting stents (DESs) in 2003. For example, in early evaluations, sirolimus-eluting stents (CYPHER™ stents from Cordis in 2003) and PTX-eluting stents (TAXUS™ stents from Boston Scientific in 2004) have shown effective inhibition of neointimal hyperplasia and prevention of restenosis in single de novo coronary lesions, with revascularization only required in approximately 10% of patients. In 2008, the Food and Drug Administration (FDA) approved two more DES devices, Medtronic's ENDEAVOR® stent delivering zotarolimus, and Abbott Laboratories' XIENCE™ V stent delivering everolimus. However, recent evidence shows that ten years post-angioplasty, the performance of DES devices may be statistically no better than that of bare metal stents.

In addition to suggesting that DES devices do not improve outcomes relative to the use of bare metal stents at later time points, recent data indicates that that the DES devices may be susceptible to both early and late in-stent thrombosis. Early stage thrombosis is generally due to initial denudation of ECs and exposure of the underlying collagen. Late stent thrombosis is characterized by the persistence of fibrin and incomplete endothelialization at time points beyond 30 days from the time of stenting. These partially endothelialized, fibrin-rich sites provide a stimulus for surface-induced thrombosis, with the presence of activated platelets possibly helping to exacerbate inflammation. Importantly, even if the incidence of thrombosis is low, such conditions are still of great concern as 90% of all thrombotic events lead to death. Additionally, late stent thrombosis has been associated with an increased frequency of other chronic maladies, including renal insufficiency, decreased left ventricular function, and diabetes. Accordingly, patients having stent thrombosis are typically prescribed antiplatelet medications, such as aspirin and PLAVIX® or TICLID®, indefinitely.

The near epidemic of pre-diabetes and progression of patients to type 2 diabetes threatens to compound coronary disease morbidity and mortality, increasing the need for coronary stenting, and increasing the incidence of stent thrombosis. In addition, diabetes can lead to serious wound sites such as those of foot ulcers as described above. In view of this, there is a need in the art for materials and methods that can provide enhanced wound healing, angiogenesis, and vascular repair in diverse medical applications. The present disclosure satisfies this need and provides other advantages as well.

BRIEF SUMMARY

One provided compound comprises: one or more P1 subunits, wherein P1 is a synthetic peptide comprising an amino acid sequence that comprises a collagen-binding domain; one or more P2 subunits, wherein P2 is a synthetic peptide comprising an amino acid sequence that comprises an integrin-binding domain; and a glycan, wherein each P1 subunit and each P2 subunit is linked to the glycan. In some embodiments, P1 is a synthetic peptide comprising an amino acid sequence having at least 80% sequence identity with the amino acid sequence RRANAALKAGELYKSILY (SEQ ID NO: 1). In some embodiments, P1 is a synthetic peptide of up to about 40 amino acids comprising the amino acid sequence RRANAALKAGELYKSILY (SEQ ID NO: 1). In some embodiments, P2 is a synthetic peptide comprising an amino acid sequence that comprises an $\alpha v \beta 3$-binding domain. In some embodiments, P2 is LXW7. In some embodiments, P2 is peg2V. In some embodiments, the glycan is a glycosaminoglycan or polysaccharide. In some embodiments, the glycan is selected from the group consisting of alginate, agarose, dextran, chondroitin, dermatan, dermatan sulfate, heparan, heparin, keratin, and hyaluronan. In some embodiments, the glycan is selected from the group consisting of dermatan sulfate, dextran, and heparin.

Also provided is a compound comprising: one or more P1 subunits, wherein P1 is a synthetic peptide comprising an amino acid sequence that comprises a collagen-binding domain; and one or more P2 subunits, wherein P2 is a synthetic peptide comprising an amino acid sequence that comprises an integrin-binding domain. In some embodiments, P1 is a synthetic peptide comprising an amino acid sequence having at least 80% sequence identity with the amino acid sequence RRANAALKAGELYKSILY (SEQ ID NO: 1). In some embodiments, P1 is a synthetic peptide of up to about 40 amino acids comprising the amino acid sequence RRANAALKAGELYKSILY (SEQ ID NO: 1). In some embodiments, P2 is a synthetic peptide comprising an amino acid sequence that comprises an $\alpha v \beta 3$-binding domain. In some embodiments, P2 is LXW7.

Also provided is a composition comprising any of the disclosed compounds described above and one or more pharmaceutically acceptable excipients, diluents, or a combination thereof.

Also provided is a method for improving endothelialization and vascularization of endothelial cells and/or endothelial progenitor cells in a subject, the method comprising administering one or more compositions, each comprising one or more of any of the disclosed compounds described above to the subject. In some embodiments, at least one of the one or more compositions further comprises one or more pharmaceutically acceptable excipients, diluents, or a combination thereof. In some embodiments, the subject is a patient suffering from a disease associated with endothelial dysfunction. In certain aspects, the disease is an ulcer. In some embodiments, the subject is in need of coronary stenting.

BRIEF DESCRIPTION OF THE DRAWINGS

FIG. 28 presents images of vasculature invading implanted collagen gels visualized with high molecular weight fluorescent dextran.
FIG. 31. Following endothelial denudation by balloon angioplasty in Ossabaw pigs, vessels were treated with saline (left) or DS-SILY (right). The saline treated vessel had high amounts of platelet binding (arrows in top left) while the DS-SILY treated vessel almost completely inhibited platelet binding (top right). Platelets that were present in the DS-SILY treated vessel remained rounded (bottom right) indicating they were not activated. Conversely, the platelets on the saline treated vessel had many protrusions (arrows in bottom left), indicating activation.

FIG. 32. Representative histology sections of (A, B) arteries with stents and (C, D) arteries without stents treated with (A, C) saline or (B, D) 10 µM DS-SILY20. Arrowheads indicate location of some stent struts; internal elastic lamina (dotted line) and luminal border (solid line) are identified, indicating the boundaries of the neointima formed following injury. (E) Neointimal hyperplasia was quantified by measuring the distance from a stent strut or the elastic lamina to the vessel lumen in arteries with or without stents, respectively. Analysis with stents: sham (n=4), DS-SILY20 (n=3); without stents: sham (n=8), DS-SILY20 (n=5). Scale bar=1 mm. * represents significance from sham-treated vessels.

FIG. 33. Attachment of cells and platelets to LXW7 and GRGD (SEQ ID NO: 2) treated surfaces. (A) Images of attached HCAECs (left panels), THP-1 monocytes (middle panels) and platelets (right panels) on surfaces treated by D-Biotin (a-c) (control), LXW7 (d-f) or GRGD (SEQ ID NO: 2) (g-i). Scale bars in a, b, d, e, g and h are 50 µm. Scale bars in c, f and i are 20 µm. (B) The number of cells or platelets attached on different treated surfaces were quantified and statistical analyses were performed. Data were expressed as mean±standard deviation: **$p<0.01$ (n=4).

DETAILED DESCRIPTION

I. General

Figure 1A:
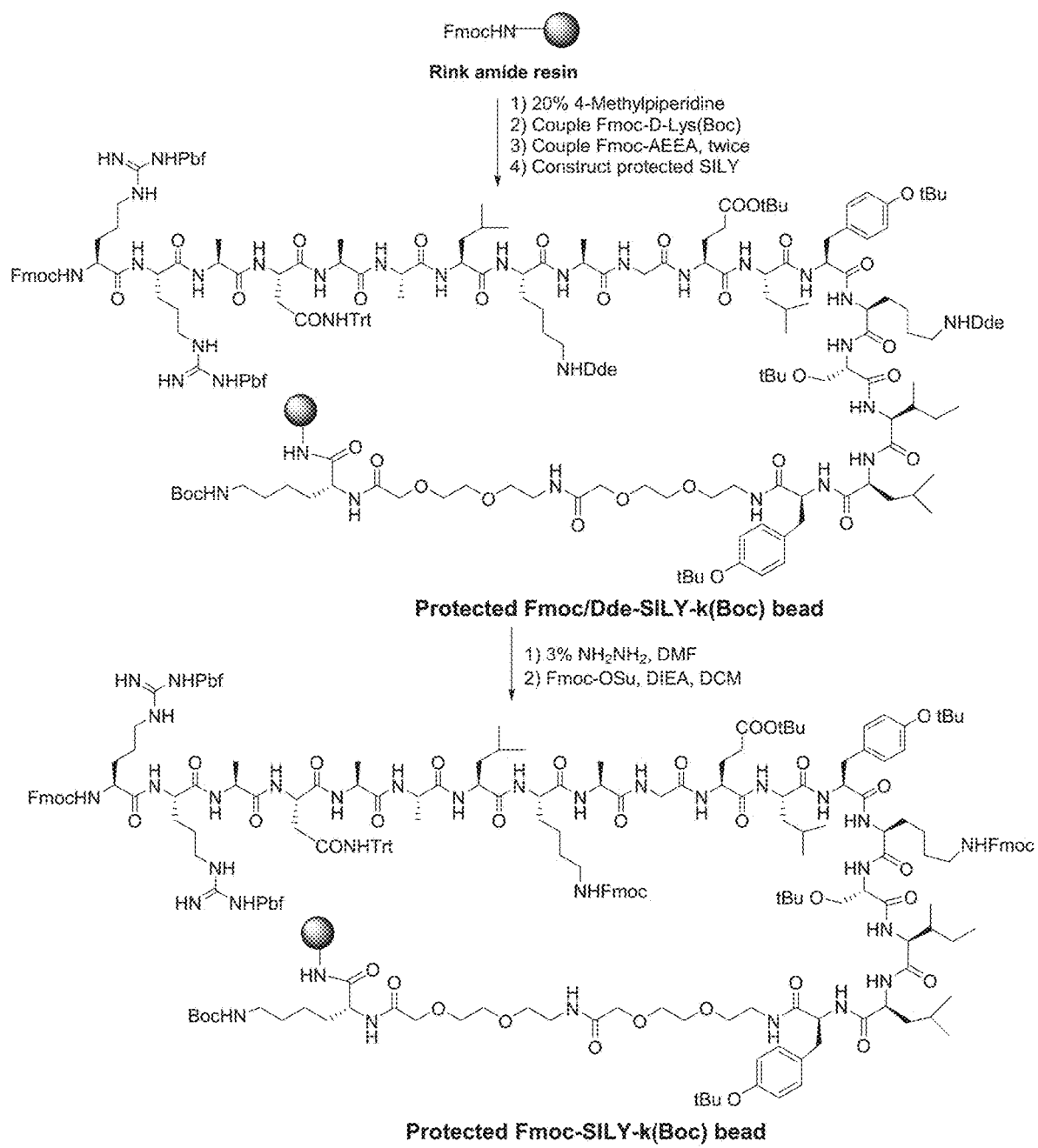
FIGS. 1A and 1B illustrate the synthetic scheme of SILY-DBCO.

The present disclosure is based, in part, on the discovery that administration of collagen-binding, pro-angiogenic proteoglycan mimetics, such as LXW7-DS-SILY, and/or a peg2V-DS-SILY variant, can provide a provisional, pro-angiogenic scaffold to support tissue regeneration while limiting systemic exposure to VEGF activity. These mimetics can protect a collagen matrix from rapid degradation, and in conjunction with EPCs promote angiogenesis in order to accelerate ischemic wound healing. For example, the addition of LXW7 to the DS-SILY molecule, (LXW7-DS-SILY), will result in a molecule that can be delivered from the end of a catheter following balloon angioplasty to coat the collagen exposed areas, prevent platelet binding and thrombosis, support capture of EPCs from blood to facilitate reendothelialization, and reduce late-lumen loss (neointimal hyperplasia). This disclosure can therefore provide a therapeutic that can selectively affect damaged areas without long-term complications of permanent stents including late stent thrombosis and a foreign body response that promotes scarring. This new therapeutic can alleviate the need for long-term daily administration of anti-clotting agents. The new therapeutic can thus substantially lower the complications associated with current drug-eluting stents.

The provided approach in preventing restenosis and late thrombosis is different from the existing method of delivering non-specific drugs, such as sirolimus and paclitaxel. The disclosed approach is innovative in allowing suppression of platelet binding and inflammation while promoting reendothelialization, and eliminating the need for implantation of a stent. In addition, the delivery is consistent with current clinical practice and is agnostic to type of balloon that is used. Advantageously, the procedure causes denudation of the blood vessel and exposes collagen, which in turn promotes platelet binding and activation. Platelet activation can lead to thrombosis and activation of the inflammatory system. Temporary anti-thrombotic coating with LXW7-DS-SILY limits both early and late stage thrombosis and inflammation, and thus promotes proper vessel recovery. In addition, the LXW7 peptide can capture circulating EPCs through specific interaction with the $\alpha_v\beta_3$ integrin and promote reendothelialization of the damaged vessel. LXW7 will not capture platelets, monocytes, or other blood cells. The provided approach is also surprisingly effective in eliminating multiple limitations of current DES technology. The new approach will block early term thrombosis, inhibit inflammation, limit SMC proliferation, and promote reendothelialization to promote vessel healing and prevent late term thrombosis.

II. Definitions

The term "scaffold" refers to a matrix that provides a three-dimensional structure suitable for cell culture, tissue engineering, or tissue regeneration. The structure of a scaffold can have, for example, the form of a stent, a shunt, a patch, a graft, or an implant. Scaffolds can be modified to promote cell recruitment, adhesion, or proliferation. Exemplary modifications include, but are not limited to, incorporation of one or more cell adhesion promoters, surface coatings, or functional groups.

The term "amino acid" refers to naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol with "D" as prefix (e.g., DArg, D-Arg or DArg for D-arginine) or by a lower-case one-letter amino acid symbol (e.g., r for D-arginine).

Amino acids can be characterized by at least one of several properties. For example, amino acids can be basic, acidic,-polar or hydrophobic. Basic amino acids are those having a basic or positively charged side chain at pH values below the pKa, and include, but are not limited to, Lys, Arg, HoArg, Agp, Agb, Dab, Dap and Orn and stereoisomers thereof. Acidic amino acids are those having an acidic or negatively charged side chain at physiological pH, and include, but are not limited to, Asp, Glu, Aad, Bec and stereoisomers thereof. Basic amino acids can generally be referred by the symbol "X$^+$" and acidic amino acids by "X$^-$". Polar amino acids generally refer to those having a polar and uncharged side chain and include, but are not limited to, Asn, Ser, Thr, Gln, and stereoisomers thereof. Similarly, hydrophobic amino acids generally refer to those having a hydrophobic side chain and include, but are not limited to, Val, Leu, Ile, Met, and Phe. One of skill in the art will appreciate that other basic and acidic amino acids are known in the art.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins*, 1984)

The term "peptide" refers to a compound made up of a single chain of D or L amino acids or a mixture of D and L amino acids joined by peptide bonds. Generally, peptides are about 2 to about 50 amino acids in length.

The term "biopolymer" refers to either a naturally occurring polymer, or a synthetic polymer that is compatible with a biological system or that mimics naturally occurring polymers. For example, and not by way of limitation, biopolymers of the present disclosure include oligosaccharides, proteins, polyketides, peptoids, hydrogels, poly(glycols) such as poly(ethylene glycol), and polylactates.

The term "ligand" refers to a molecule that selectively binds, covalently or noncovalently, to another specific molecule or to a specific part of a molecule.

The term "bind" includes any physical or chemical attachment or close association, which may be permanent or temporary.

The term "noncovalent interactions" refers to the interaction of two species in close proximity that does not form a covalent bond. Types of noncovalent interactions include, for example, hydrogen bonding, van der Waals interaction, coordination, pi-pi interaction, hydrophobic interactions and hydrophilic interactions.

The term "covalent interaction" refers to the interaction of two species in close proximity that form a covalent bond.

The term "αvβ3 integrin" refers to a receptor of vitronectin. αvβ3 integrin serves as a receptor for a variety of extracellular matrix proteins displaying the arginine-glycine-aspartic acid (RGD) tripeptide sequence. These proteins include vitronectin, fibronectin, fibrinogen, laminin, collagen, and Von Willibrand's factor.

The term "subject" refers to animals such as mammals, including, but not limited to, primates (e.g., humans), cows, sheep, goats, horses, dogs, cats, rabbits, rats, mice and the like. In certain embodiments, the subject is a human.

The term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "alkoxy" refers to an alkyl group having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "halogen" refers to fluorine, chlorine, bromine and iodine.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbomane, decahydronaphthalene and adamantane. For example, $C_3$-scycloalkyl includes cyclopropyl, cyclobutyl, cyclopentyl, cyclohexyl, cyclooctyl, and norbornane.

As used herein, the term "alkyl-cycloalkyl" refers to a radical having an alkyl component and a cycloalkyl component, where the alkyl component links the cycloalkyl component to the point of attachment. The alkyl component is as defined above, except that the alkyl component is at least divalent in order to link to the cycloalkyl component and to the point of attachment. In some instances, the alkyl component can be absent. The cycloalkyl component is as defined within. Examples of alkyl-cycloalkyl include methylene-cyclohexane, among others.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent in order to link to the heterocycloalkyl component and to the point of attachment. In some instances, the alkyl component can be absent. The heterocycloalkyl component is as defined above. Examples of alkyl-heterocycloalkyl include methylene-piperidinyl, among others.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferably as aryl is naphthyl, phenyl, or phenyl mono- or di-substituted by alkoxy, phenyl, halogen, alkyl, or trifluoromethyl; especially phenyl or phenyl mono- or di-substituted by alkoxy, halogen, or trifluoromethyl; and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O)R', —NR'R", —SR', —R', —CN, —NO$_2$, —CO$_2$R', —CONR' R", —C(O)R', —OC(O)NR' R", —NR"C(O)R', —NR"C(O)$_2$R', —NR'—C(O)NR"R'", —NH—C(NH$_2$)=NH, —NR' C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-heteroaryl" refers to a radical having an alkyl component and a heteroaryl component, where the alkyl component links the heteroaryl component to the point of attachment. The alkyl component is as defined above, except that the alkyl component is at least divalent in order to link to the heteroaryl component and to the point of attachment. In some instances, the alkyl component can be absent. The heteroaryl component is as defined within. Examples of alkyl-heteroaryl include methylene-pyridyl, among others.

III. Compounds

The compounds provided herein each include one or more synthetic collagen-binding peptides P1, and one or more synthetic integrin-binding peptides P2. In some embodiments, the synthetic peptide P1 includes an amino acid sequence having at least 80% sequence identity with the amino acid sequence RRANAALKAGELYKSILY (SEQ ID NO: 1). In certain aspects, the synthetic peptide P1 includes the amino acid sequence RRANAALKAGELYKSILY (SEQ ID NO: 1). Variability can be present in the P1 sequence. For example, the synthetic peptide P1 can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Accordingly, the P1 sequence can be modified such that a sequence having at least about 80% sequence identity, or at least about 83% sequence identity, or at least about 85% sequence identity, or at least about 90% sequence identity, or at least about 95% sequence identity, or at least about 98% sequence identity thereto is incorporated in the scaffold compound, provided the sequence is capable of binding to collagen.

The amino acid length of synthetic peptide P1 can be, for example, between 20 and 60, e.g., between 20 and 44, between 24 and 48, between 28 and 52, between 32 and 56, or between 36 and 60. In terms of upper limits, the amino acid length of P1 can be less than 60, e.g., less than 56, less than 52, less than 48, less than 44, less than 40, less than 36, less than 32, less than 32, less than 28, or less than 24. In terms of lower limits, the amino acid length of P1 can be up to 20, e.g., up to 24, up to 28, up to 32, up to 32, up to 36, up to 40, up to 44, up to 48, up to 52, or up to 56. Longer lengths, e.g., greater than 60, and shorter lengths, e.g., less than 20, are also contemplated.

The synthetic peptide P2 can be a peptide ligand including an integrin-binding domain. Peptide ligands suitable for use with the present disclosure can be selected to increase the attachment of endothelial cells and/or endothelial progenitor cells to the scaffold. For example, the peptide ligand can be a compound of Formula I:

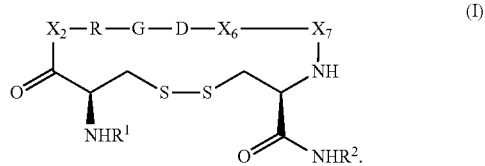

(I)

$X_2$, $X_6$, and $X_7$ can each independently be an amino acid, wherein at least one of $X_2$, $X_6$, and $X_7$ is a D-amino acid. $R^1$ of formula I can be H, $C_{1-6}$ alkyl, —C(O)$R^{1a}$, or L-A. $R^{1a}$ can be $C_{1-6}$ alkyl, $C_{1-6}$ heteroalkyl, $C_{1-6}$ alkyl-NH$_2$, $C_{1-6}$ alkyl-C(O)N(H)—$C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, or $C_{1-6}$ alkyl-heteroaryl, wherein the cycloalkyl, heterocycloalkyl, heteroaryl, and aryl groups are optionally substituted with a halogen, —NO$_2$, —OH, —CN, $C_{1-6}$ alkyl, $C_{1-6}$ alkoxy, $C_{1-6}$ haloalkyl, or $C_{1-6}$ haloalkoxy. $R^2$ can be H, $C_{1-6}$ alkyl, or L-A. Radical L is a linker and radical A is an active agent.

The compounds of formula I can include basic amino acids, such as those having a positively charged side chain. Non-limiting examples of basic amino acids are Lys, Arg, HoArg, Agp, Agb, Dab, Dap and Orn, and stereoisomers thereof. The compounds of formula I can also include acidic amino acids, such as those with a negatively charged side chain. Non-limiting examples of acidic amino acids are Asp, Glu, Aad, and Bec, and stereoisomers thereof. Basic amino acids can generally be referred by the symbol "X$^+$" and acidic amino acids by "X$^-$". One of skill in the art will appreciate that other basic and acidic amino acids are known in the art.

Amino acids useful in the compounds of the present disclosure include naturally-occurring amino acids, as well as those amino acids that are later modified, e.g., γ-carboxyglutamate and O-phosphoserine, as well as unnatural amino acids. Naturally-occurring α-amino acids include (shown with the corresponding 3 letter and single letter codes), without limitation, alanine (Ala, A), cysteine (Cys, C), aspartic acid (Asp, D), glutamic acid (Glu, E), phenylalanine (Phe, F), glycine (Gly, G), histidine (His, H), isoleucine (Ile, I), arginine (Arg, R), lysine (Lys, K), leucine (Leu, L), methionine (Met, M), asparagine (Asn, N), proline (Pro, P), glutamine (Gln, Q), serine (Ser, S), threonine (Thr, T), valine (Val, V), tryptophan (Trp, W) and tyrosine (Tyr, Y). Stereoisomers of a naturally-occurring α-amino acids include, without limitation, D-alanine (DAla, a), D-cysteine (DCys, c), D-aspartic acid (DAsp, d), D-glutamic acid (DGlu, e), D-phenylalanine (DPhe, f), D-histidine (DHis, h), D-isoleucine (DIle, i), D-arginine (DArg, r), D-lysine (DLys, k), D-leucine (DLeu, l), D-methionine (DMet, m), D-asparagine (DAsn, n), D-proline (DPro, p), D-glutamine (DGln, q), D-serine (DSer, s), D-threonine (D-Thr, t), D-valine (D-Val, v), D-tryptophan (DTrp, w) and D-tyrosine (DTyr, y).

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups. Suitable unnatural amino acids include, without limitation, α-aminohexanedioic acid (Aad), α-aminobutyric acid (Abu), 3-aminobenzoic acid (3Abz), azetidine-2-carboxylic acid (Aca), 1-aminocyclobutane-1-carboxylic acid (Acb), α-amino-3-chloro-4,5-dihydro-5-isoazoleacetic acid (Acdi), 4-amino-4-carboxy-1,1-dioxo-tetrahydrothiopyran (Acdt), 1-amino-1-cyclohexane carboxylic acid (Ach), 1-aminocyclopentane-1-carboxylic acid (Acp), 1-aminocyclopropane-1-carboxylic acid (Acpc), 4-amino-4-carboxytetrahydropyran (Actp), 8-amino-1,4-dioxaspiro[4.5]decane-8-carboxylic acid (Aecc), (S)-2-amino-4-guanidino-butanoic acid (Agb), allylglycine (Agl), (S)-2-amino-3-guanidino-propanoic acid (Agp), 2-aminoheptanoic acid (Aha), 1-amino-1-(4-hydroxycyclohexyl) carboxylic acid (Ahch), α-aminoisobutyric acid (Aib), 2-aminoindane-2-carboxylic acid (Aic), 1-amino-1-(4-ketocyclohexyl) carboxylic acid (Akch), 2-aminooctanoic acid (Aoa), 2-amino-2-naphthylacetic acid (Ana), 1-amino-1-(3-piperidinyl) carboxylic acid (3Apc), 1-amino-1-(4-piperidinyl) carboxylic acid (4Apc), 2-amino-3-(4-piperidinyl) propionic acid (4App), homoarginine (HoArg), Nα-methyl-arginine ((NMe)Arg), Nα-methyl-aspartic acid ((NMe)Asp), α-aminooctanedioic acid (Asu), (R)-2-amino-3-(2-carboxyethylsulfanyl)propanoic acid (Bec), 4,4'-biphenylalanine (Bipa), (R)-2-amino-3-(carboxymethylsulfanyl)propanoic acid (Bmc), 4-carboxymethoxyphenylalanine (Bmp), 4-benzoylphenylalanine (Bpa), 3-benzothienylalanine (Bta), 5H-thiazolo[3,2-a]pyridine-3-carboxylic acid (Btd), β-t-butylalaine (Bua), α-tert-butylglycine (Bug), 4-cyano-2-aminobutyric acid (Cab), cyclobutylalanine (Cba), cyclohexylalanine (Cha), homocyclohexylalanine (HoCha), α-cyclohexylglycine (Chg), citrulline (Cit), homocitrulline (HoCit), cyclopropylalanine (Cpa), cyclopentylglycine (Cpeg), 3-carboxymethyl-1-phenyl-1,3,8-triazaspiro[4,5]decan-4-one (Cptd), homocysteine (HoCys,), α,γ-diaminobutyric acid (Dbu), diethylglycine (Deg), 3,3-diphenyl-alanine (Dpa), di-n-propylglycine (Dpg), α,β-diaminopropionic acid (Dap), α,γ-diaminobutyric acid (Dab), 2-furyl-Alanine (Fua), homoarginine (HoArg), hydroxyproline (Hyp), O-benzyl-hydroxyproline (Hyp (Bzl)), homoleucine (HoLeu), 2-Indanylglycine (Ing), methionine sulfoxide (Met(O)), methionine methylsulfonium (Met (S-Me)), 3-(1-naphthyl)alanine (Nal1), 3-(2-naphthyl)alanine (Nal2), 3-(carboxymethylamino)propanoic acid (Nglu), nipecotic acid (Nip), isonipecotic acid (IsoNip), norleucine (Nle), norvaline (Nva), octahydroindole-2-carboxylic acid (Oic), ornithine (Orn), 2-pyridylalanine (2 Pal), 3-(3-pyridyl)alanine (3 Pal), 3-(4-pyridyl)alanine (4 Pal), penicillamine (Pen), homophenylalanine (HoPhe), Nα-methyl-phenylalanine ((NMe)Phe), 2-chloro-phenylalanine (Phe(2C$_1$)), α-methyl-phenylalanine ((CαMe)Phe), 3,4-dimethoxy-phenylalanine (Phe(3,4-di OMe)), 4-carboxyphenylalanine (Phe(4COOH)), 4-nitro-phenylalanine (Phe(4-NO$_2$)), 4-trifluoromethyl-phenylalanine (Phe(4-CF$_3$)), 4-tert-butyl-phenylalanine (Phe(4-tBu)), 3,4-dichloro-phenylalanine (Phe(3,4-diCl)), phenylglycine (Phg), (2S,5R)-5-phenyl pyrrolidine-2-carboxylic acid (Ppca), propargylglycine (Pra), homoproline (HoPro), β-homoproline (βHoPro), 2-quinoylalanine (2Qal), Nα-methylglycine (Sar), homoserine (HoSer), 3-styryl-alanine (Sta), taurine (Tau), 4-thiazoylalanine (Tha), 3-(2-thienyl)alanine (2Thi), 3-(3-thienyl)alanine (3Thi), thiazolidine-4-carboxylic acid (Thz), thiazolidine-2-carboxylic acid (Thz(2-COOH)), tetrahydro-isoquinoline-3-carboxylic acid (3Tic), (R)-1,2,3,4-tetrahydroisoquinoline-3-carboxylic acid (Tic), 3,5-dinitrotyrosine (Tyr(3,5di NO$_2$)), 3-nitrotyrosine (Tyr(3-NO$_2$)), 3,5-diiodotyrosine (Tyr(diI)), and Nα-methyl-valine ((NMe)-Val), a phenylalanine analog, derivatives of lysine, and stereoisomers thereof (see, Liu and Lam, Anal. Biochem., 295:9-16 (2001)). As such, the unnatural α-amino acids are present either as unnatural L-α-amino acids, unnatural D-α-amino acids, or combinations thereof.

The amino acids can also be categorized as basic, acidic, hydrophobic and/or polar. Some suitable basic amino acids of the disclosure are Lys, Arg, HoArg, Agp, Agb, Dab, Dap, Orn and stereoisomers thereof. Some suitable acidic amino acids are Asp, Glu, Aad, Bec and stereoisomers thereof. Hydrophobic amino acids include, but are not limited to, Val, Leu, Ile, Met and Phe, and stereoisomers thereof. Polar amino acids include, but are not limited to, Asn, Ser, Gln, Thr, and stereoisomers thereof.

Suitable phenylalanine analogs include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe(2,4-diCl)), 3,4-dichlorophenylalanine (Phe(3,4-diCl)), 4-benzoylphenylalanine (Bpa), 4-carboxyphenylalanine (Phe(4COOH)), 4,4'-biphenylalanine (Bip), 2,3,4,5,6-pentafluorophenylalanine (Phe(F$_5$)), 3,4,5-trifluorophenylalanine (Phe(F3)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr (Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and Dbu, include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81,stereoisomers thereof, and combinations thereof. See, Table 1 for a description of the structures for each of the lysine derivatives. Derivatives of Orn and Dbu are similar to the lysine derivatives with corresponding carboxylic acid attached to the side chain of Orn and Dbu, respectively.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF₃), N-methyl-Phe(4-CF₃), N-methyl-Phe(4-NO₂), N-methyl-Phe(4-CN), N-methyl-Bpa, N-methyl-Phg(4-Cl), N-methyl-Phg(4-Br), N-methyl-Tyr (Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Amino acid mimetics are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

N-substituted glycines are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Examples of N-substituted glycines suitable for use in the present disclosure include, without limitation, N-(2-aminoethyl)glycine, N-(3-aminopropyl)glycine, N-(2-methoxyethyl)glycine, N-benzylglycine, (S)—N-(1-phenylethyl)glycine, N-cyclohexylmethylglycine, N-(2-phenylethyl) glycine, N-(3-phenylpropyl)glycine, N-(6-aminogalactosyl) glycine, N-(2-(3'-indolylethyl)glycine, N-(2-(p-methoxyphenylethyl))glycine, N-(2-(p-chlorophenylethyl) glycine, and N-[2-(p-hydroxyphenylethyl)]glycine. N-substituted glycine oligomers, referred to herein as "peptoids," have been shown to be protease resistant (Miller et al., *Drug Dev. Res.*, 35:20-32 (1995)). As such, peptoids containing at least one unnatural α-amino acid, D-amino acid, or a combination thereof are within the scope of the present disclosure.

In still other embodiments, radicals $R^1$ and $R^2$ of formula I can each independently be H, $C_{1-6}$ alkyl or L-A. And radical L can be a linker and radical A can be an active agent.

In still other embodiments, $R^1$ can be acetyl, 3-amino propanoyl, Ebes, isobutyryl, valeryl, cyclohexyl acetyl, 5-bromo-2-furoyl, 3-phenyl propionyl, p-chlorophenyl acetyl, 4-nitrobezoyl, 3,5-dihydroxy beznoyl, 4-(trifluoromethyl)benzoyl, 2-Methylthiazole-4-carbonyl, nicotinyl, 2-naphthoyl, or biphenyl-4-carbonyl.

In some embodiments, radical $X_2$ of formula I can be Gly, Ala, Sar or β-alanine, and stereoisomers thereof. Similarly, radical $X_6$ can be Val, Leu, Ile, Met, Phe, Asn, Glu, Gln, His, Lys, Arg, Asp, Gly, Ala, Ser, Thr, Tyr, Trp, Pro, Aad, Bec, Bmc, Bmp, Phe(4COOH), Hyp, HoSer, Tha, Ahch, Actp, Akch, Tyr(diI), Trp, Thz, 2Thi, 3Thi, Cit, HoCit, Aib, Nglu, or Fua, and stereoisomers thereof. In addition, radical $X_7$ can be Val, Leu, Ile, Met, Phe, Asn, Glu, Gln, His, Lys, Arg, Asp, Gly, Ala, Ser, Thr, Tyr, Trp, Pro, Bmp, HoSer, Nglu, HoCit, Bec, Aad, Hyp, Ahch, Phe(4COOH), Akch, Aecc, Abu, Phe(3,4-diOMe), Cpa, 2Thi, 3Thi, Thz, Phg, Phe(4-NO₂), Nle, (NMe)Phe, Aic, Chg, Bta, Bpa, Nal2, Nal1, Tic, Ppca, Cha, Bipa, Deg, Dpg, Acpc, Bmc, Cit, Sar, Tha, Pra, Actp, Aib, Agl, Acbc, Fua, Nva, Trp, Bug, Ach, (NMe)Val, Cpeg, (CαMe)Phe, Tyr(diI), Phe(2-Cl), Bua, HoPhe, HoLeu, Sta, Ing, Phe(4-CF₃), Oic, Dpa, Phe(4-t-Bu), HoCha or Phe(3, 4-diCl), and stereoisomers thereof. In other embodiments, each of radicals $X_2$, $X_6$ and $X_7$ can be a D-amino acid.

In other embodiments, the P2 peptide ligand of the scaffold of the present disclosure can have formula Ia:

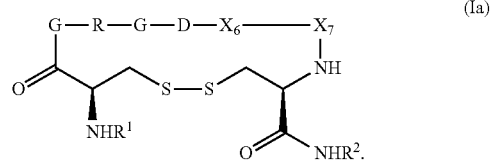

(Ia)

Radicals $R^1$ and $R^2$ of formula Ia are as described above. In some embodiments, radical $X_6$ can be DSer, DAsp, Ahch, Bmp, DGlu, Nglu or DCit, and radical $X_7$ can be DPhe, DGlu, DSer, DBug, DBta, DVal, DAgl DPra, D(NMe)Val, D(CαMe)Val, DAbu, DIng, DIle, Actp, DTha, DAsp, DNal1 or Ppca. In some other embodiments, radical $X_6$ can be DAsp or DSer, and radical $X_7$ can be DGlu, DPhe, DSer, DVal, DBug or DBta.

$R^1$ and $R^2$ of formula Ia can each independently be H or $C_{1-6}$ alkyl. In some embodiments, $R^1$ is H. In some embodiments, $R^2$ is H. In some embodiments, $R^1$ and $R^2$ are both H.

$X^6$ of formula Ia can be DSer, DAsp, DGlu, or DCit. $X^7$ of formula Ia can be DPhe, DGlu, DSer, DBug, DBta, DVal, DAgl, DPra, D(NMe)Val, D(CαMe)Val, DAbu, DIng, DIle, DTha, DAsp, or DNal1. In some embodiments, $X^6$ is DAsp and DSer. In some embodiments, $X^7$ is DGlu, DPhe, DSer, DVal, DBug, or DBta.

In another embodiment, the P2 peptide ligand of the present disclosure can be cGRGDsfc, cGRGDdfc, cGRGD-sec, cGRGDdsc, cGRGDd-DBug-c, cGRGDd-DBta-c, cGRGDd-DBta-c, cGRGDdvc, CGRGDdvc, cGRGDdvC, CGRGDdvC, DPen-GRGDdv-DPen, DPen-GRGDdvc, cGRGDdv-DPen, Ac-cGRGDdvc, (β-alanine)-cGRGDdvc, (Ebes)-cGRGDdvc, caRGDdvc, c-Sar-RGDdvc, c-β-alanine-RGDdvc, cG-HoArg-GDdvc, cG-Agp-GDdvc, cG-Agp-GEdvc, cGRGDd-DAgl-c, cGRGDd-DPra-c, cGRGDd-DBug-c, cGRGDd-D(NMe)Val-c, cGRGDd-D(CαMe)Val-c, cGRGDd-DAbu-c, CGRGDd-DIng-c, c-Sar-RGD-Ahch-ic, c-Sar-RGD-Ahch-DBug-c, cGRGDd-DAgl-C, C—Sar-RGDd-DPra-C, C—Sar-RGDd-Actp-C, c-Sar-RGDd-DPra-C, c-Sar-RGDd-Actp-C, CGRGDd-DTha-C, cGRGDd-DPra-C, cGRGDd-Actp-C, c-Sar-RGD-Ahch-iC, c-Sar-RGD-Ahch-DBug-C, C—Sar-RGD-Bmp-dC, CGRGDe-Ppca-c, cGRGD-Nglu-Ppca-c, cGRGDd-DNal1-c orcGRGDd-DBta-c. In other embodiments, the P2 peptide of the present disclosure can be cGRGDsfc, cGRGDdfc, cGRGDsec, cGRGDdsc, cGRGDdvc, cGRGDd-DBug-c or cGRGDd-DBta-c.

In another embodiment, the P2 peptide ligand of the present disclosure can be cGRGDsfc, cGRGDdfc, cGRGDsec, cGRGDdsc, cGRGDdvc, CGRGDdvc, cGRGDdvC, CGRGDdvC, caRGDdvc, c-Sar-RGDdvc, c-β-alanine-RGDdvc, cGRGDd-DAgl-c, cGRGDd-DPra-c, cGRGDd-DBug-c, DPen-GRGDdv-DPen, DPen-GRGDdvc, cGRGDdv-DPen, cGRGDd-D(NMe)Val-c, cGRGDd-D(CαMe)Val-c, cGRGDd-DAbu-C, cGRGDdic, cGRGDd-DIng-c, c-Sar-RGD-Ahch-ic, c-Sar-RGD-Ahch-DBug-c, cGRGDd-DAgl-C, C—Sar-RGDd-DPra-C, C—Sar-RGDd-Actp-C, c-Sar-RGDd-DPra-C, c-Sar-RGDd-Actp-C, CGRGDd-DTha-C, cGRGDd-DPra-C, cGRGDd-Actp-C, c-Sar-RGD-Ahch-iC, c-Sar-RGD-Ahch-DBug-C, C—Sar-RGD-Bmp-dC, CGRGDe-Ppca-c, CGRGD-Nglu-Ppca-c, CGRGDd-DNal1-C, CGRGD-D3Thi-Ppca-c, cGRGDd-DBta-c, cG-HoArg-GDdvc, cG-(NMe)Arg-GDdvc, cGR-Sar-Ddvc, cGRG-(NMe)Asp-dvc, cG-Agp-GDdvc, cG-Agp-GEdvc, cGRGDsdC, cGRGDd-DIng-c, cGRGDd-DNal1-c, cGRGDd-DNal2-c, cGRGDd-D3Thi-c, cGRGDd-D2Thi-c, cGRGDdwc, cGRGDd-DTha-c, cGRGD-DCit-Ppca-c, cGRGDe-Ppca-c, cGRGD-NGlu-Ppca-c, cGRGD-DCit-DBta-c, cGRGD-DBec-Ahch-c, or cGRGD-DBec-DPra-c. In some embodiments, the peptide ligand is cGRGDdvc (LXW7). In some embodiments, the P2 peptide ligand is peg2V (described in further detail below).

The P2 peptide ligand can function to increase the attachment of endothelial cells and/or endothelial progenitor cells. The P2 peptide ligand can have an affinity for a cell surface integrin. The integrin can regulate retention, mobilization, vascularization, or endothelialization of cells. In some embodiments, the P2 peptide ligand binds to one or more of integrins α4β1, α5β1, α6β1, αvβ3 and avβ5. In some embodiments, the P2 peptide ligand binds to integrin αvβ3 on the cells.

In some embodiments, the scaffold compound further includes a glycan, wherein each P1 subunit and each P2 subunit is linked to the glycan. The glycan of the scaffold compound can be, for example, a glycosaminoglycan or a polysaccharide. The glycosaminoglycan can be selected from the group consisting of alginate, agarose, dextran, chondroitin, dermatan, dermatan sulfate, heparin, heparan sulfate, keratin, and hyaluronan. In one embodiment, the glycan is selected from the group consisting of dermatan sulfate, dextran, and heparin. In some embodiments, the glycan is dermatan sulfate (DS). Dermatan sulfate is a natural glycosaminoglycan found mostly in skin, but also in blood vessels, heart valves, tendons, lungs and intestinal mucosa. In addition to its role as a major constituent of the skin and other organs, dermatan sulfate is believed to play a part in repairing wounds, regulating the coagulation of blood, and responding to infections, though its role in these processes is not well understood.

The P1 and P2 synthetic peptides can be directly linked to the glycosaminoglycan, or linked to the glycosaminoglycan via a linker. The linker can include one or more bivalent fragments selected independently in each instance from the group consisting of alkylene, heteroalkylene, cycloalkylene, cycloheteroalkylene, arylene, and heteroarylene, each of which is optionally substituted. As used herein heteroalkylene represents a group resulting from the replacement of one or more carbon atoms in a linear or branched alkylene group with an atom independently selected in each instance from the group consisting of oxygen, nitrogen, phosphorus and sulfur.

IV. Pharmaceutical Compositions and Methods

The compounds described herein can be administered to a subject (e.g., a patient in need of treatment for a disease such as an ulcer, or in need of coronary stenting). In various embodiments, the compounds can be administered intravenously or into muscle, for example. Suitable routes for parenteral administration include intravascular, intravenous, intraarterial, intramuscular, cutaneous, subcutaneous, percutaneous, intradermal, and intraepidermal delivery. Suitable means for parenteral administration include needle (including microneedle) injectors, infusion techniques, and catheter-based delivery.

Pharmaceutical compositions of any of the compounds described herein can be formulated for parenteral administration or catheter-based delivery. For example, such compositions can include: a) a pharmaceutically active amount of one or more of the compounds; b) a pharmaceutically acceptable pH buffering agent to provide a pH in the range of about pH 4.5 to about pH 9; c) an ionic strength modifying agent in the concentration range of about 0 to about 300 millimolar; and d) a water soluble viscosity modifying agent in the concentration range of about 0.25% to about 10% total formula weight; or any individual component a), b), c), or d); or any combinations of a), b), c) and d).

In various embodiments described herein, the pH buffering agents for use in the compositions and methods herein described are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In various embodiments described herein, the ionic strength modifying agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and non-ionic water soluble polymers; crosslinked acrylic acid polymers such as the "carbomer" family of polymers, e.g., carboxypolyalkylenes that can be obtained commercially under the CARBOPOL® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or basic agent are employed in order to facilitate achieving the desired pH of the formulation.

In various embodiments described herein, parenteral formulations can be suitably formulated as a sterile non-aqueous solution or as a dried form to be used in conjunction with a suitable vehicle such as sterile, pyrogen-free water. The preparation of parenteral formulations under sterile conditions, for example, by lyophilization, can readily be accomplished using standard pharmaceutical techniques available to those skilled in the art.

In various embodiments described herein, the solubility of compounds used in the preparation of a parenteral formulation can be increased by the use of appropriate formulation techniques, such as the incorporation of solubility-enhancing compositions such as mannitol, ethanol, glycerin, polyethylene glycols, propylene glycol, poloxomers, and others known to those of skill in the art.

In various embodiments described herein, formulations for parenteral administration can be formulated to be for immediate and/or modified release. Modified release formulations include delayed, sustained, pulsed, controlled, targeted and programmed release formulations. Thus, one or more compounds can be formulated as a solid, semi-solid, or thixotropic liquid for administration as an implanted depot providing modified release of the active compound. Illustrative examples of such formulations include drug-coated stents and copolymeric(dl-lactic, glycolic)acid (PGLA) microspheres. In another embodiment, one or more scaffold compounds, or compositions comprising one or more scaffold compounds, can be continuously administered, where appropriate.

In any of the embodiments described herein, the compounds can be administered alone or in combination with suitable pharmaceutical carriers or diluents. Diluent or carrier ingredients used in the compound formulation can be selected so that they do not diminish the desired effects of the compounds. The compound formulation can be in any suitable form. Examples of suitable dosage forms include aqueous solutions of the compounds, for example, a solution in isotonic saline, 5% glucose, or other well-known pharmaceutically acceptable liquid carriers such as alcohols, glycols, esters, and amides.

Suitable dosages of the compounds can be determined by standard methods, for example by establishing dose-response curves in laboratory animal models or in clinical trials. Illustratively, suitable dosages of compounds (administered in a single bolus or over time) include from 1 ng/kg to about 10 mg/kg, 100 ng/kg to about 1 mg/kg, from about 1 μg/kg to about 500 μg/kg, or from about 100 μg/kg to about 400 μg/kg. In each of these embodiments, dose/kg refers to the dose per kilogram of patient mass or body weight. In other illustrative aspects, effective doses can range from about 0.01 μg to about 1000 mg per dose, 1 μg to about 100 mg per dose, or from about 100 μg to about 50 mg per dose, or from about 500 μg to about 10 mg per dose, or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose.

It is also contemplated that any of the formulations described herein can be used to administer the compounds (e.g., one or more types) either in the absence or the presence of a catheter-based device. The compounds can be formulated in an effective amount of an excipient. In any of the embodiments described herein, the excipient can have a concentration ranging from about 0.4 mg/mL to about 6 mg/mL. In various embodiments, the concentration of the excipient can range from about 0.5 mg/mL to about 10 mg/mL, about 0.1 mg/mL to about 6 mg/mL, about 0.5 mg/mL to about 3 mg/mL, about 1 mg/mL to about 3 mg/mL, about 0.01 mg/mL to about 10 mg/mL, or about 2 mg/mL to about 4 mg/mL.

The dosage of the compounds can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, an effective dose can range from about 1 ng/kg to about 10 mg/kg, from about 100 ng/kg to about 1 mg/kg, from about 1 μg/kg to about 500 μg/kg, or from about 100 μg/kg to about 400 μg/kg. In each of these embodiments, dose/kg refers to the dose per kilogram of patient mass or body weight. In other illustrative aspects, effective doses can range from about 0.01 μg to about 1000 mg per dose, from about 1 μg to about 100 mg per dose, or from about 100 μg to about 50 mg per dose, or from about 500 μg to about 10 mg per dose, or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses can range from about 0.01 μg to about 1000 mg per dose, about 1 μg to about 100 mg per dose, about 100 μg to about 1.0 mg, about 50 μg to about 600 μg, about 50 μg to about 700 μg, about 100 μg to about 200 μg, about 100 μg to about 600 μg, about 100 μg to about 500 μg, about 200 μg to about 600 μg, from about 100 μg to about 50 mg per dose, from about 500 μg to about 10 mg per dose, or from about 1 mg to 10 mg per dose. In other illustrative embodiments, effective doses can be 1 μg, 10 μg, 25 μg, 50 μg, 75 μg, 100 μg, 125 μg, 150 μg, 200 μg, 250 μg, 275 μg, 300 μg, 350 μg, 400 μg, 450 μg, 500 μg, 550 μg, 575 μg, 600 μg, 625 μg, 650 μg, 675 μg, 700 μg, 800 μg, 900 μg, 1.0 mg, 1.5 mg, 2.0 mg, 10 mg, 100 mg, or 100 mg to 30 grams.

Any effective regimen for administering the compounds can be used. For example, the compounds can be administered as a single dose, or as a multiple-dose daily regimen. Further, a staggered regimen, for example, one to five days per week can be used as an alternative to daily treatment.

In any of the embodiments herein described, it is to be understood that a combination of two or more compounds, for example, differing in the presence or absence of a glycan, can be used in place of a single compound.

Compounds can be sterilized before, during, and/or after formulation. As used herein, "sterilization" or "sterilize" or "sterilized" refers to disinfecting the compounds by removing unwanted contaminants including, but not limited to, endotoxins and infectious agents.

In various illustrative embodiments, the compounds can be disinfected and/or sterilized using conventional sterilization techniques including propylene oxide or ethylene oxide treatment, gas plasma sterilization, gamma radiation, electron beam, and/or sterilization with a peracid, such as peracetic acid. Sterilization techniques which do not adversely affect the structure and biotropic properties of the compounds can be used. Illustrative sterilization techniques include exposing the compounds to peracetic acid, 1-4 Mrads gamma irradiation (or 1-2.5 Mrads of gamma irradiation), ethylene oxide treatment, sterile filtration, or gas plasma sterilization. In some embodiments, the compounds are subjected to one or more sterilization processes. For example, the compounds can be subjected to sterile filtration. The compounds can be dispensed into any type of container, which can be wrapped in a plastic wrap or a foil wrap, and can be further sterilized after such placement in a container.

The compounds can be combined with minerals; amino acids; sugars; peptides; proteins; vitamins (such as ascorbic acid); laminin; collagen; fibronectin; hyaluronic acid; fibrin; elastin; aggrecan; growth factors (such as epidermal growth factor, platelet-derived growth factor, transforming growth factor beta, or fibroblast growth factor); glucocorticoids such as dexamethasone; viscoelastic altering agents such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid); poly(glycolic acid); copolymers of lactic and glycolic acids; or other polymeric agents both natural and synthetic.

V. Kits

The compounds and compositions disclosed herein can be provided in one or more types of kits. The kit can include packaging with one or more containers, at least one of which contains a scaffold compound. The kit can also contain instructions for use of the components of the kit. In one embodiment, the kit comprises one or more vessels, vials, or containers that hold one or more compounds. The kit can also include any of the following components: one or more formulations or concentrations (dosages) of compounds, a buffer, a sterilizing or disinfecting agent, a syringe, a needle, proteins or polysaccharides, and/or instructional materials describing methods for using the kit reagents. In any of these embodiments, the kit can contain a component selected from the group consisting of a catheter, a stent, a balloon, and a combination thereof. The compounds can be lyophilized, for example, in a buffer or in water.

Articles of manufacture are also contemplated for any of these embodiments. In any of the kit or article of manufacture embodiments described herein, the kit or article of manufacture can comprise a dose or multiple doses of the compounds. The compounds can be in a primary container, for example, a glass vial, such as an amber glass vial with a rubber stopper and/or an aluminum tear-off seal. In another embodiment, the primary container can be plastic or aluminum, and the primary container can be sealed. In another embodiment, the primary container is contained within a secondary container to further protect the composition from light.

In any of the embodiments described herein, the kit or article of manufacture can contain instructions for use. Other suitable kit or article of manufacture components include excipients, disintegrants, binders, salts, local anesthetics (e.g., lidocaine), diluents, preservatives, chelating agents, buffers, tonicity agents, antiseptic agents, wetting agents, emulsifiers, dispersants, stabilizers, and the like. These components can be available separately or admixed with the compounds. Any of the composition embodiments described herein can be used to formulate the kit or article of manufacture.

VI. Embodiments

The following embodiments are contemplated. All combinations of features and embodiments are contemplated.

Embodiment 1: A compound comprising: one or more P1 subunits, wherein P1 is a synthetic peptide comprising an amino acid sequence that comprises a collagen-binding domain; one or more P2 subunits, wherein P2 is a synthetic peptide comprising an amino acid sequence that comprises an integrin-binding domain; and a glycan, wherein each P1 subunit and each P2 subunit is linked to the glycan.

Embodiment 2: An embodiment of embodiment 1, wherein P1 is a synthetic peptide comprising an amino acid sequence having at least 80% sequence identity with the amino acid sequence RRANAALKAGELYKSILY (SEQ ID NO: 1).

Embodiment 3: An embodiment of embodiment 1, wherein P1 is a synthetic peptide of up to 40 amino acids comprising the amino acid sequence RRANAALKAGELYKSILY (SEQ ID NO: 1).

Embodiment 4: An embodiment of any one of embodiments 1-3, wherein P2 is a synthetic peptide comprising an amino acid sequence that comprises an avβ3-binding domain.

Embodiment 5: An embodiment of any one of embodiments 1-4, wherein P2 is LXW7.

Embodiment 6: An embodiment of any one of embodiments 1-4, wherein P2 is peg2V.

Embodiment 7: An embodiment of any one of embodiments 1-6, wherein the glycan is a glycosaminoglycan or polysaccharide.

Embodiment 8: An embodiment of embodiment 7, wherein the glycan is selected from the group consisting of alginate, agarose, dextran, chondroitin, dermatan, dermatan sulfate, heparan, heparin, keratin, and hyaluronan.

Embodiment 9: An embodiment of embodiment 8, wherein the glycan is selected from the group consisting of dermatan sulfate, dextran, and heparin.

Embodiment 10: A compound comprising: one or more P1 subunits, wherein P1 is a synthetic peptide comprising an amino acid sequence that comprises a collagen-binding domain; and one or more P2 subunits, wherein P2 is a synthetic peptide comprising an amino acid sequence that comprises an integrin-binding domain.

Embodiment 11: An embodiment of embodiment 10, wherein P1 is a synthetic peptide comprising an amino acid sequence having at least 80% sequence identity with the amino acid sequence RRANAALKAGELYKSILY (SEQ ID NO: 1).

Embodiment 12: An embodiment of embodiment 10, wherein P1 is a synthetic peptide of up to 40 amino acids comprising the amino acid sequence RRANAALKAGELYKSILY (SEQ ID NO: 1).

Embodiment 13: An embodiment of any one of embodiments 10-12, wherein P2 is a synthetic peptide comprising an amino acid sequence that comprises an avβ3-binding domain.

Embodiment 14: An embodiment of any one of embodiments 10-13, wherein P2 is LXW7.

Embodiment 15: A composition comprising the compound of an embodiment of any one of embodiments 1-14 and one or more pharmaceutically acceptable excipients, diluents, or a combination thereof.

Embodiment 16: A method for improving endothelialization and vascularization of endothelial cells and/or endothelial progenitor cells in a subject, the method comprising administering to the subject a composition comprising the compound of an embodiment of any one of embodiments 1-14.

Embodiment 17: An embodiment of embodiment 16, wherein the composition comprises one or more pharmaceutically acceptable excipients, diluents, or a combination thereof.

Embodiment 18: A method for improving endothelialization and vascularization of endothelial cells and/or endothelial progenitor cells in a subject, the method comprising: administering to the subject a first composition comprising the compound of an embodiment of any one of embodiments 1-9; and administering to the subject a second composition comprising the compound of an embodiment of any one of embodiments 10-14.

Embodiment 19: An embodiment of embodiment 18, wherein at least one of the first composition and the second composition comprises one or more pharmaceutically acceptable excipients, diluents, or a combination thereof.

Embodiment 20: An embodiment of embodiment 18 or 19, wherein the second composition is the first composition.

Embodiment 21: An embodiment of any one of embodiments 16-20, wherein the subject is a patient suffering from a disease associated with endothelial dysfunction.

Embodiment 22: An embodiment of embodiment 21, wherein the disease is an ulcer.

Embodiment 23: An embodiment of any one of embodiments 16-20, wherein the subject is in need of coronary stenting.

VII. Examples

The present disclosure will be described in greater detail by way of specific examples. The following examples are offered for illustrative purposes only, and are not intended to limit the disclosure in any manner. Those of skill in the art will readily recognize a variety of noncritical parameters which can be changed or modified to yield essentially the same results.

Example 1. Synthesis of SILY-DBCO

Figure 1B:
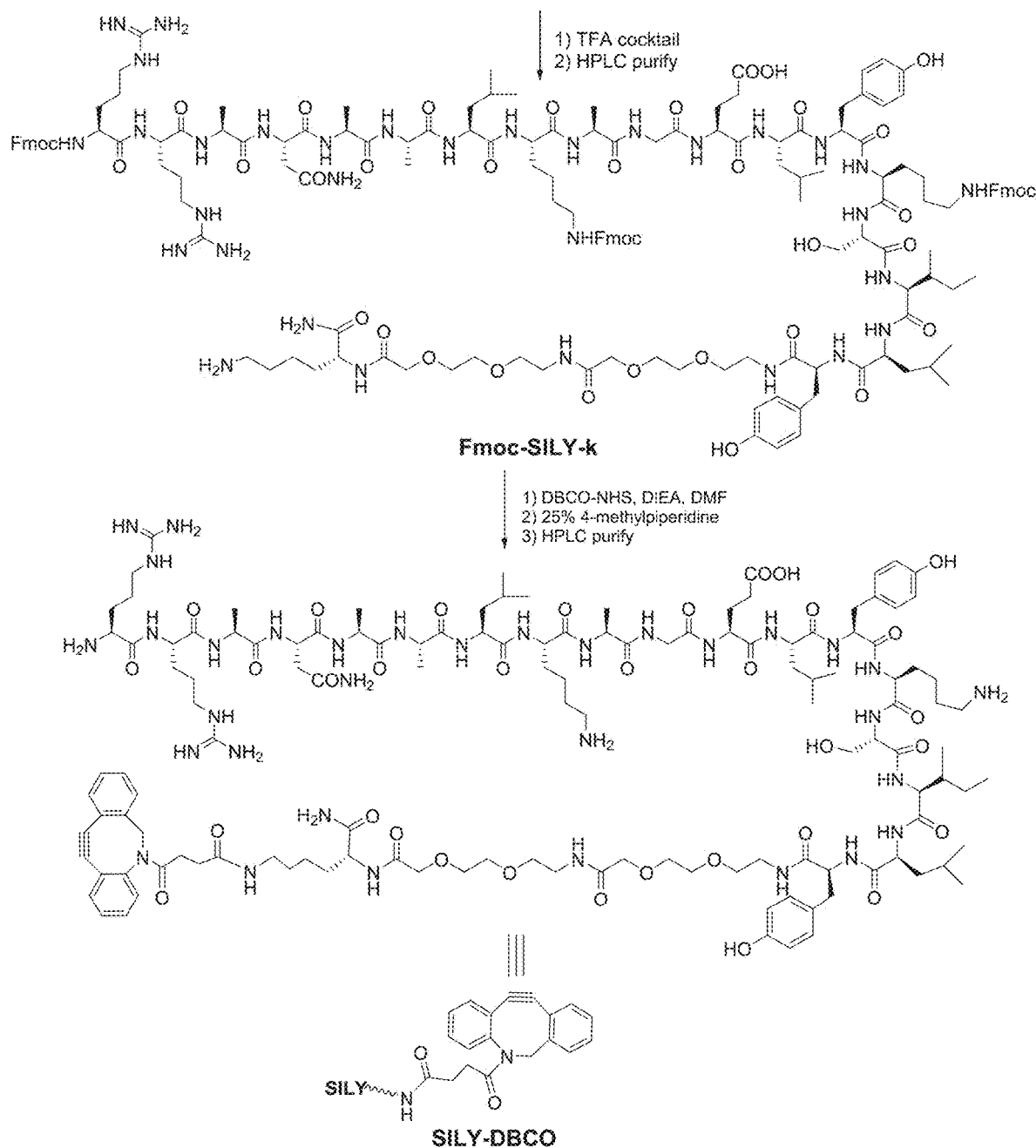

The synthetic scheme of SILY-DBCO is shown in FIGS. 1A and 1B. Fmoc-SILY-k was first synthesized by standard solid phase peptide synthesis (SSPS) approach, followed by DBCO coupling in solution phase with DBCO-OSu. Rink amide MBHA resin (1.0 g, 0.503 mmol, loading 0.503 mmol/g) was swollen in DMF for 3 hours before Fmoc-deprotection. Protected Fmoc/Dde-SILY-k(Boc) beads were prepared with automated peptide synthesizer (CS-Bio). Five-fold excess of Fmoc-amino acids were used for the coupling in presence of HCTU (6 eq.)/DIEA (12 eq.). The coupling times for the first 10 and the latter couplings were 2 hours and 3 hours, respectively. The Fmoc was removed with 20% 4-methylpiperidine twice (5 minutes, 15 minutes). The following Fmoc-amino acids were coupled sequentially: Fmoc-D-Lys(Boc)-OH, Fmoc-AEEA linker, Fmoc-AEEA linker, Fmoc-Tyr(tBu)-OH, Fmoc-Leu-OH, Fmoc-Ile-OH, Fmoc-Ser(tBu)-OH, Fmoc-Lys(Dde)-OH, Fmoc-Tyr(tBu)-OH, Fmoc-Leu-OH, Fmoc-Glu(tBu)-OH, Fmoc-Gly-OH, Fmoc-Ala-OH, Fmoc-Lys(Dde)-OH, Fmoc-Leu-OH, Fmoc-Ala-OH, Fmoc-Ala-OH, Fmoc-Asn(Trt)-OH, Fmoc-Ala-OH, Fmoc-Arg(pbf)-OH, Fmoc-Arg(Pbf)-OH. The beads were transferred to a 20-ml column from the synthesizer. The N-terminal Fmoc and Dde groups were removed with 3% $NH_2NH_2$ in DMF (10 minutes, 15 minutes). After washing with DMF, MeOH, and DCM respectively, the free amino groups were re-protected with Fmoc using Fmoc-OSu (10 eq.) in presence of DIEA (20 eq.) in DCM. This step was repeated until a Kaiser test was negative. The resulting Fmoc-protected SILY-k(Boc) beads were thoroughly washed with DMF, MeOH and DCM and then dried under vacuum for 1 hour before adding a cleavage cocktail of 82.5% TFA: 5% phenol: 5% thioanisole: 5% water: 2.5% TIS. The beads were rotated at room temperature for 4 hours. The liquid was collected and concentrated by blowing with nitrogen gas. The crude product was precipitated with cold ether and purified by reverse-phase HPLC and lyophilized to give Fmoc-SILY-k in powder form. The identity of the compound was confirmed by MALDI-TOF MS, calculated for $C_{155}H_{218}N_{32}O_{37}$(m/z): 3119.61; Found: 3120.82 (MH$^+$).

Fmoc-SILY-k (200 mg, 0.0577 mmol) was dissolved in anhydrous DMF (1 mL), then DBCO-OSu (25.6 mg, 0.06347 mmol) and DIEA (55 μL, 0.31735 mmol) were added to the solution. The reaction solution was stirred at room temperature for 1 hour. HPLC results indicated the completion of coupling. Cold ether was added to the liquid, and precipitate was collected and redissolved in 25% 4-methylpiperidine (1 mL). The solution was stirred at room temperature for 1 hour. Cold ether was added to precipitate the crude product which was purified by HPLC. The eluent was lyophilized to yield off-white powder SILY-DBCO. MALDI-TOF-MS, calculated for $C_{129}H_{201}N_{33}O_{33}$: 2740.51; Found: 2741.67 (MH$^+$).

Example 2. Synthesis of LXW7-2N3

Figure 2:
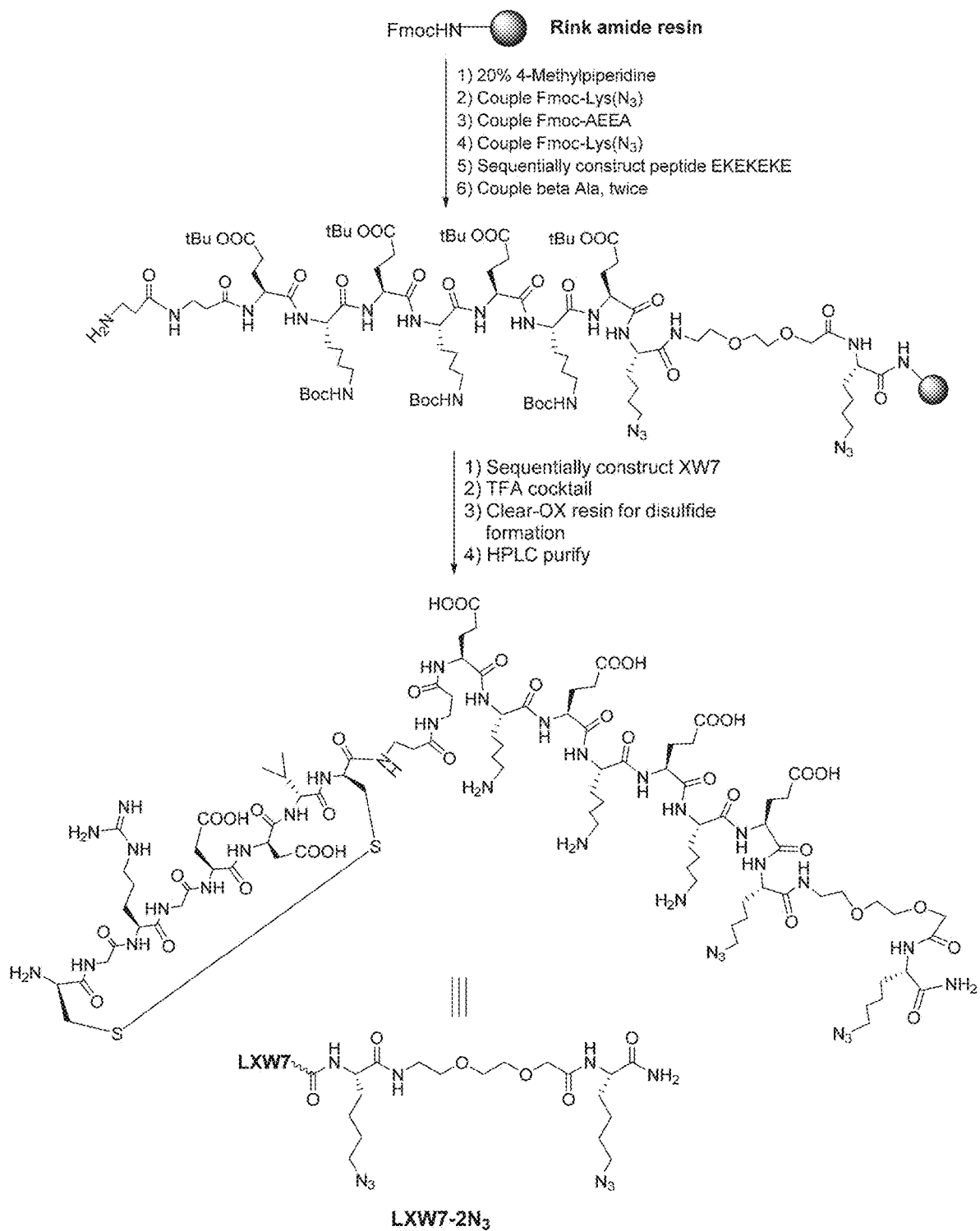
FIG. 2 illustrates the synthetic scheme of LXW7-2N3.

The synthesis of LXW7-2N3 was achieved employing SPPS by CS Bio synthesizer as shown in FIG. 2. The following Fmoc-amino acids were coupled to Fmoc-deprotected Rink amide resin sequentially with HCTU/DIEA coupling as described above: Fmoc-Lys(N$_3$)—OH, Fmoc-AEEA linker, Fmoc-Lys(N$_3$)—OH, Fmoc-Glu(tBu)-OH, Fmoc-Lys(Boc)-OH, Fmoc-Glu(tBu)-OH, Fmoc-Lys(Boc)-OH, Fmoc-Glu(tBu)-OH, Fmoc-Lys(Boc)-OH, Fmoc-Glu(tBu)-OH, Fmoc-beta Ala-OH, Fmoc-beta Ala-OH, Fmoc-D-Cys(Trt)-OH, Fmoc-D-Val-OH, Fmoc-D-Asp(tBu)-OH, Fmoc-Asp(tBu)-OH, Fmoc-Gly-OH, Fmoc-Arg(Pbf)-OH, Fmoc-Gly-OH, Fmoc-D-Cys(Trt)-OH. The linear peptide was cleaved off the beads with TFA cocktail as mentioned above. The linear crude peptide was precipitated with cold ether and cyclized with CLEAR OX resin in 50% 0.1 M ammonium acetate buffer in acetonitrile (ACN) for 3 hours (Ellman test was negative). The liquid was collected and lyophilized to give the crude peptide which was purified with HPLC. The eluent was lyophilized to give designed cyclic LXW7-2N3. MALDI-TPF MS confirmed the structure. Calculated for $C_{91}H_{153}N_{33}O_{34}S_2$: 2316.07; Found: 2317.40 (MH$^+$).

Example 3. Synthesis of LXW7-(SILY)$_2$ Conjugate

Figure 3:
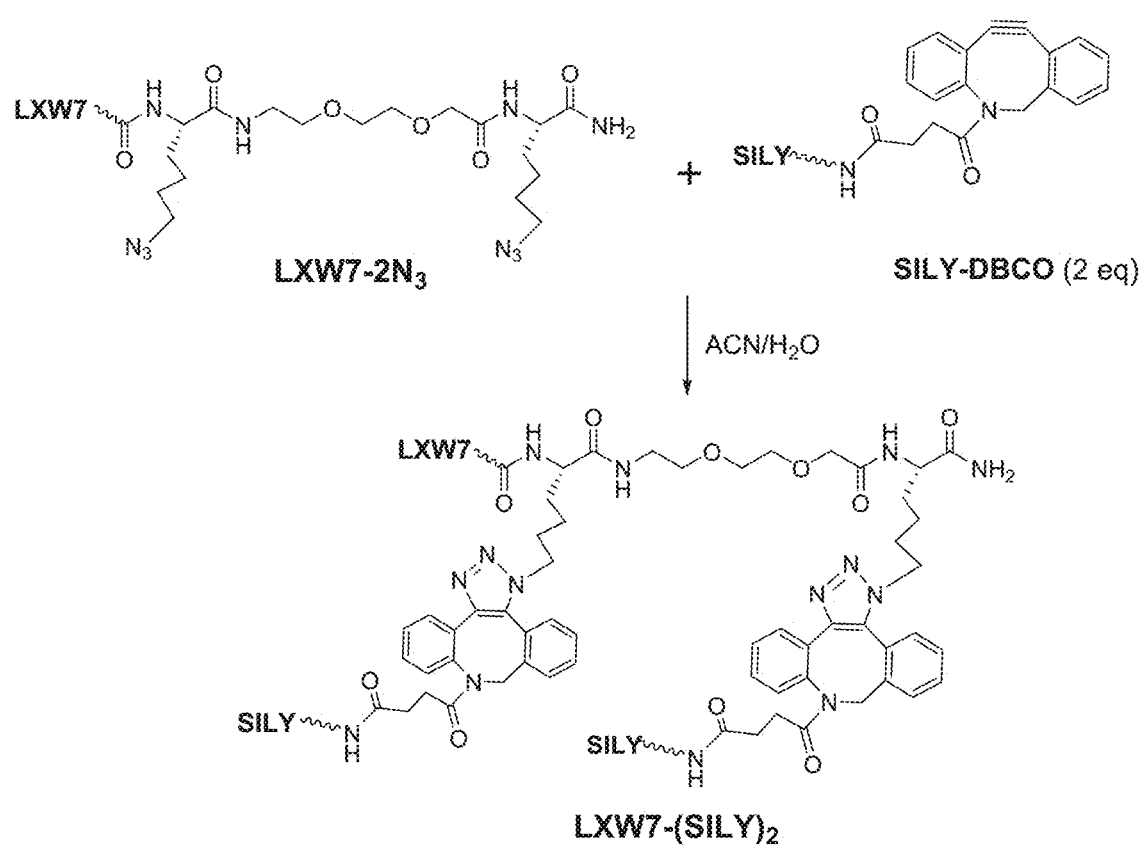
FIG. 3 illustrate the synthetic scheme of LXW7-(SILY)$_2$.

The LXW7-(SILY)$_2$ conjugate was synthesized by mixing the SILY-DBCO with LXW7-2N$_3$ in a mole ratio of 2:1 in acetonitrile/water (1:1) (FIG. 3). The resulting solution was stirred at room temperature for 3 h, then at 4° C. overnight. The solution was directly submitted for HPLC purification. The eluent was lyophilized to give LXW7-(SILY)$_2$ as off-white powder.

Example 4. Synthesis of LXW7-DBCO

Figure 4:
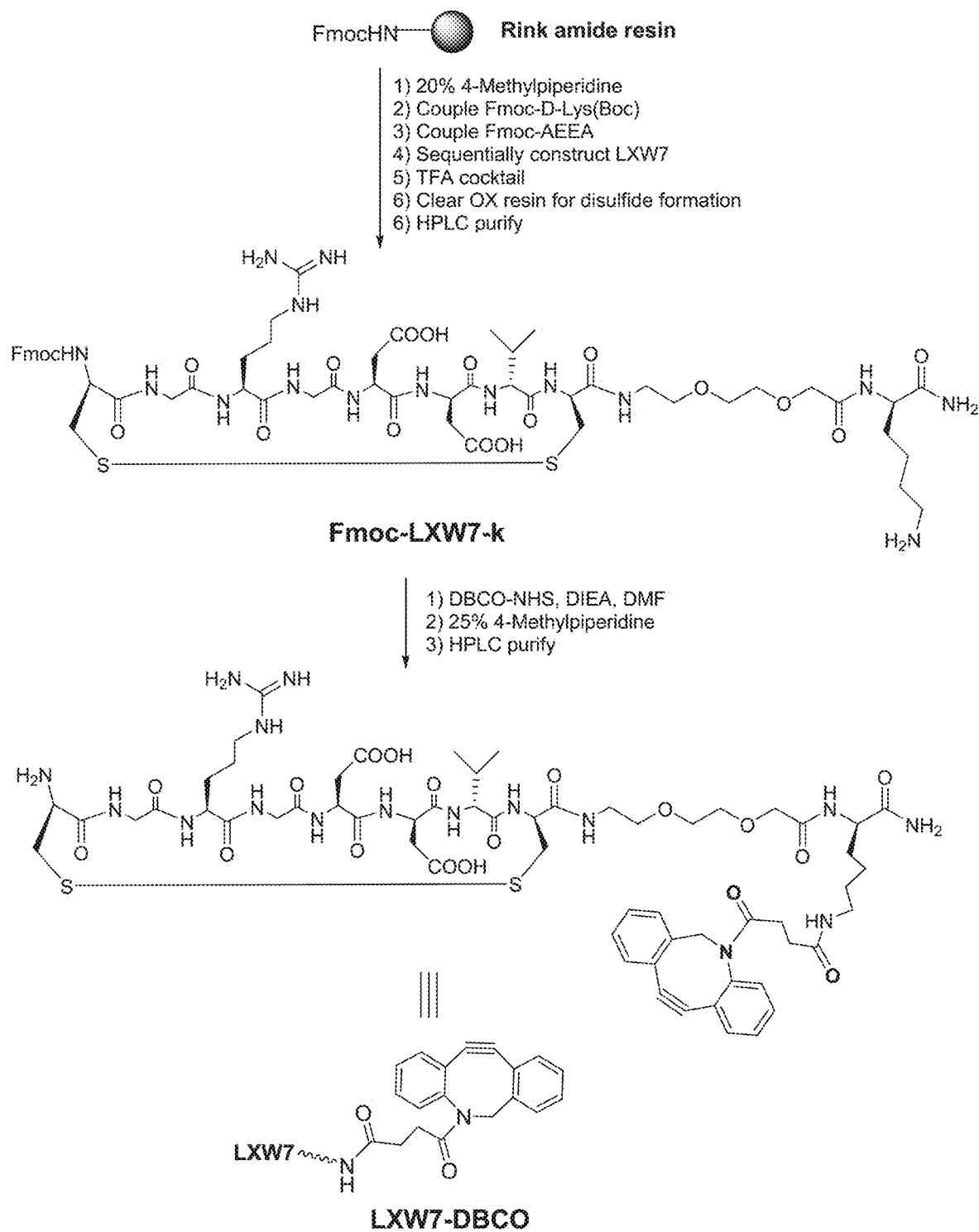
FIG. 4 illustrates the synthetic scheme of LXW7-DBCO.

The synthetic route of LXW7-DBCO is shown in FIG. 4. The synthesis of LXW7-DBCO was achieved using a strategy similar to that of SILY-DBCO as described above. The following Fmoc-amino acids were sequentially coupled to Fmoc-deprotected Rink amide resin: Fmoc-D-Lys(Boc)-OH, Fmoc-AEEA, Fmoc-D-Cys(Trt)-OH, Fmoc-D-Val-OH, Fmoc-D-Asp(tBu)-OH, Fmoc-Asp(tBu)-OH, Fmoc-Gly-OH, Fmoc-Arg(Pbf)-OH, Fmoc-Gly-OH and Fmoc-D-Cys(Trt)-OH. Linear Fmoc-LXW7-k was cleaved off the beads and purified by HPLC, followed by disulfide formation using CLEAR OX beads in 50% 0.1 M ammonium acetate buffer in ACN for 3 hours (until Ellman test was negative). The liquid was collected and lyophilized to give crude Fmoc-LXW7-k which was further purified with HPLC. The eluent was collected and lyophilized to yield cyclic Fmoc-LXW7-k as off-white powder. MALDI-TOF MS confirmed the identity. Calculated for $C_{56}H_{81}N_{15}O_{18}S_2$: 1315.53. Found: 1316.70 (MH$^+$).

Fmoc-LXW7-k was then coupled with DBCO-OSu, followed by Fmoc-deprotection and purification to give LXW7-DBCO, as described in synthesis of SILY-DBCO. MALDI-TOF MS calculated for $C_{60}H_{84}N_{16}O_{18}S_2$: 1380.56. Found: 1381.80 (MH$^+$).

Example 5. Synthesis of SILY-2N3

Figure 5:
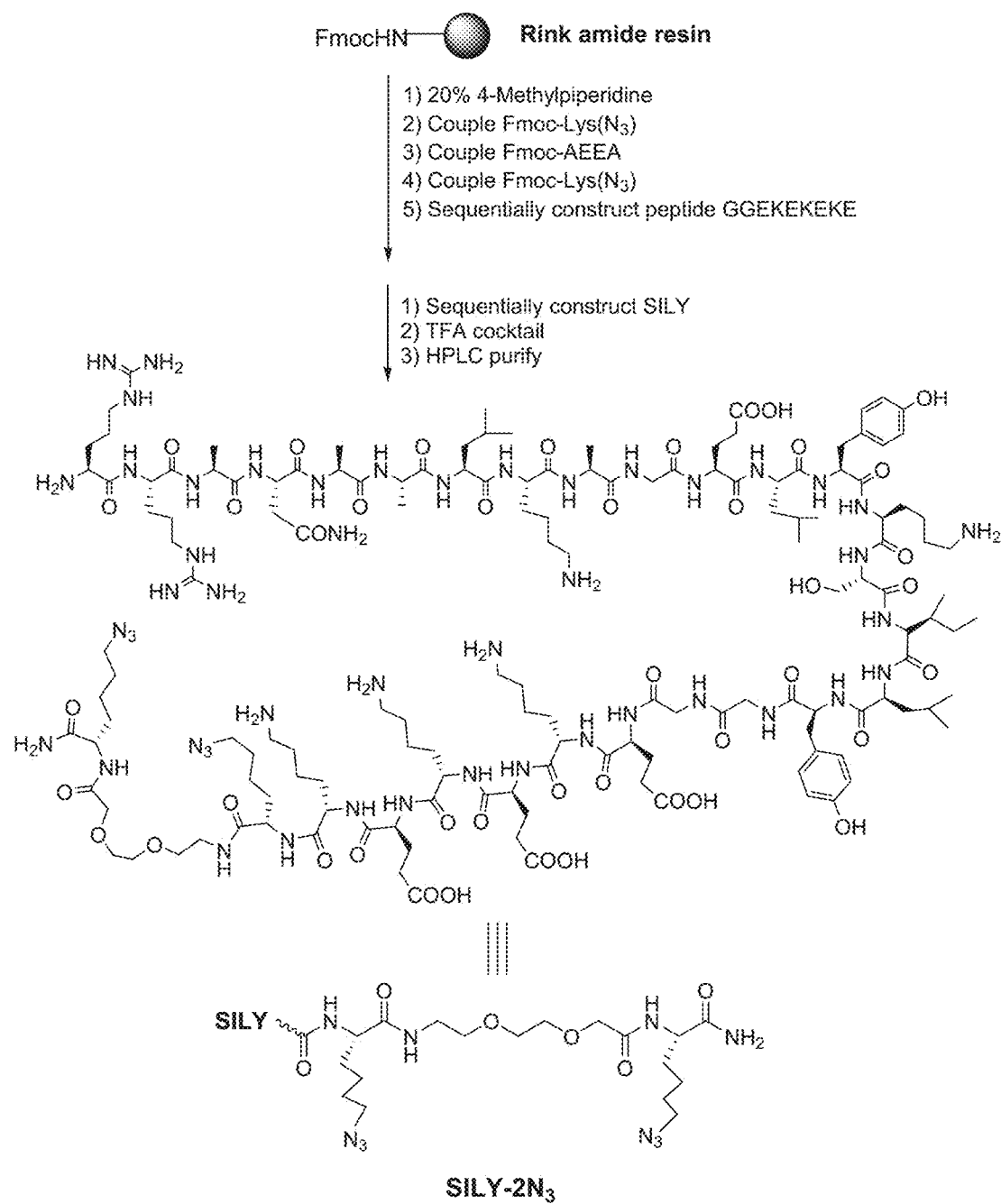
FIG. 5 illustrate the synthetic scheme of SILY-2N3.

The synthesis of SILY-2N3 was similar to that of LXW7-2N3, except that the di-peptide linker of (beta Ala)-(beta Ala) in LXW7-2N3 was replaced with GG in SILY-2N3. The scheme is shown in FIG. 5. MALDI-TOF MS calculated for $C_{147}H_{248}N_{48}O_{43}$: 3373.87. Found: 3374.95 (MH$^+$).

Example 6. Synthesis of SILY-(LXW7)$_2$ Conjugate

Figure 6:
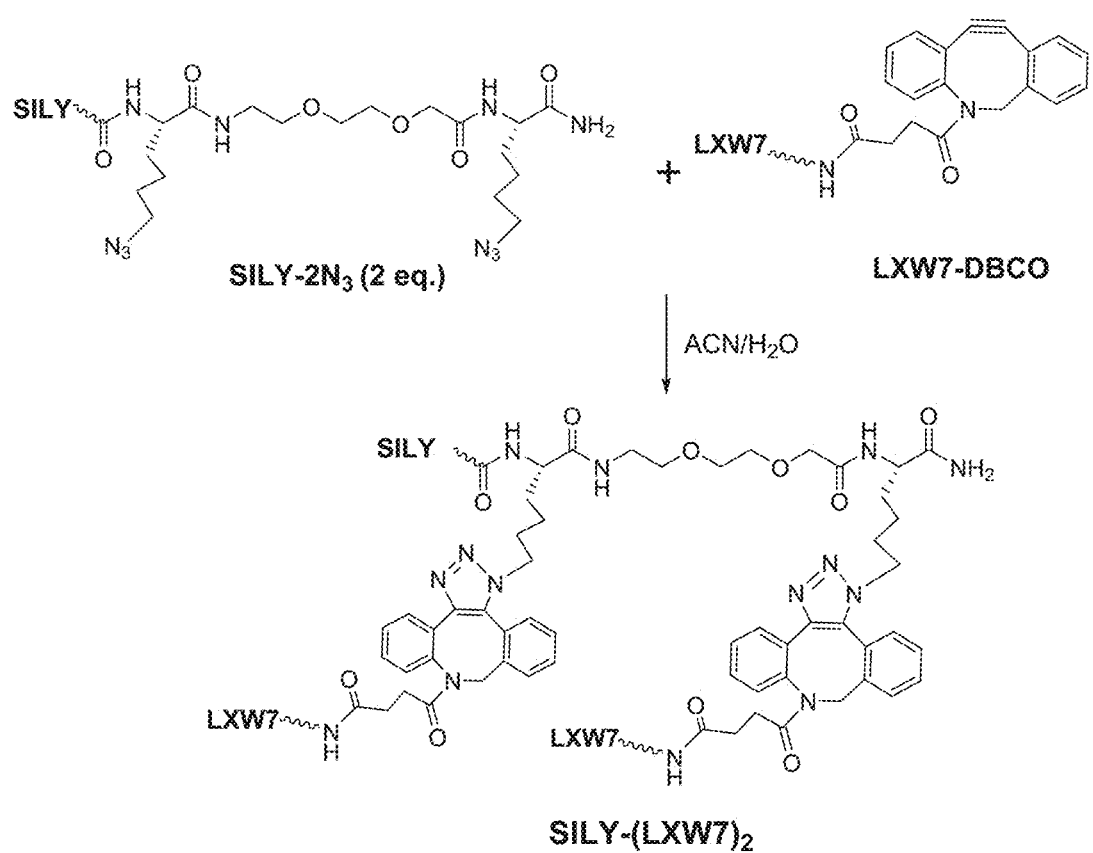
FIG. 6 illustrates the synthetic scheme of SILY-(LXW7)$_2$ conjugate.

The SILY-(LXW7)$_2$ conjugate was synthesized by mixing the LXW7-DBCO with SILY-2N3 in a mole ratio of 2:1 in acetonitrile/water (1:1) (FIG. 6). The resulting solution was stirred at room temperature for 3 hours, and then at 4° C. overnight. The solution was directly submitted for HPLC purification. The eluent was lyophilized to give SILY-(LXW7)$_2$ as off-white powder.

Example 7. EC Attachment on Collagen Surface Modified with LXW7-SILY (Collagen-LXW7-SILY)

Target culture wells in a 24-well plate were coated with 100 µg/mL Rat Tail Type I Collagen for 1 hour at 37° C. Collagen coated wells were rinsed 3 times with DPBS. LXW7-(SILY)2 or (LXW7)2-SILY was incubated in the wells at a concentration of 50 µM for 1 hour at 37° C. The wells were washed 3 times with DPBS and blocked with 1% BSA for 1 hour. After the wells were rinsed 3 times with DPBS, 5×10$^4$ human endothelial colony-forming cells (HECFCs) suspended in the EGM-2 EC growth medium were added to the wells which were then incubated for 5 minutes at 37° C. and 5% $CO_2$. The wells were rinsed 3 times with DPBS to wash off the unattached cells, and the attached cells were fixed in 10% formalin for 20 minutes. The cell nuclei were stained with DAPI and imaged using an Olympus IX81 microscope. Quantification of nuclei was performed using the ImageJ software (NIH).

Figure 7:
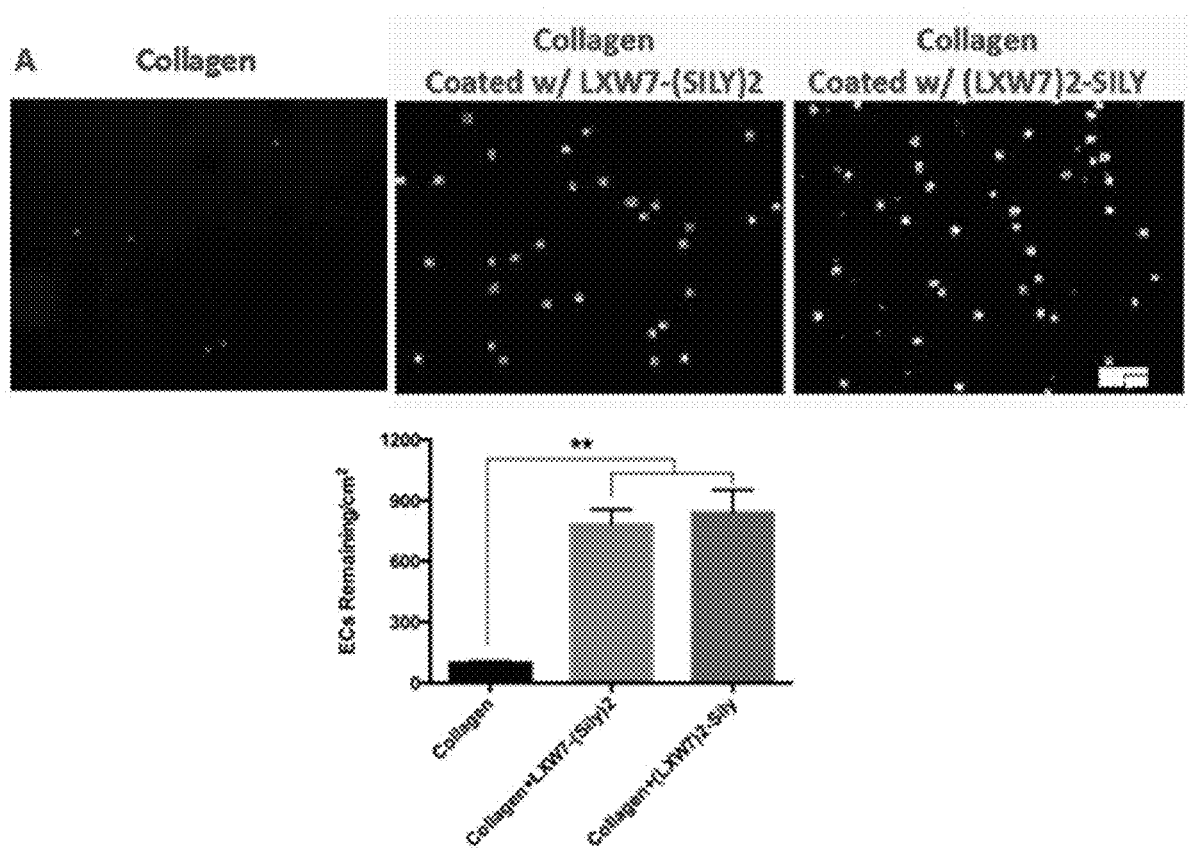
FIG. 7 presents images and a graph of human endothelial colony forming cells (HECFCs) binding on collagen surface (5 min).

As shown in FIG. 7, HECFC attachment on collagen surface modified with LXW7-(SILY)2 or (LXW7)2-SILY was significantly higher than collagen surface without modification. HECFC attachment on (LXW7)2-SILY was significantly higher than on LXW7-(SILY)2, which indicated that (LXW7)2-SILY modification of collagen surface was more effective in improving HECFC attachment.

Example 8. Effect of LXW7-SILY on EC Apoptosis Induced by Hypoxia

Target culture wells in a 96-well plate were coated with 100 µg/mL Rat Tail Type I Collagen for 1 hour at 37° C. Collagen coated wells were rinsed 3 times with DPBS. LXW7-(SILY)2 or (LXW7)2-SILY was added and incubated in the well at a concentration of 50 µM for 1 hour at 37° C. The wells were washed 3 times with DPBS and 2×10$^4$ HECFCs suspended in the EGM2 medium were added to the wells, and incubated overnight at 37° C. and 5% $CO_2$. The cells were transferred to 1% O2 and cultured for 48 hours in EBM2 (EC basal medium without growth factors) or EGM2 (complete EC growth medium with all growth factors) respectively. Caspase 3 activity assay was then performed to determine early apoptosis of the cultured cells according to the product manual.

Figure 8:
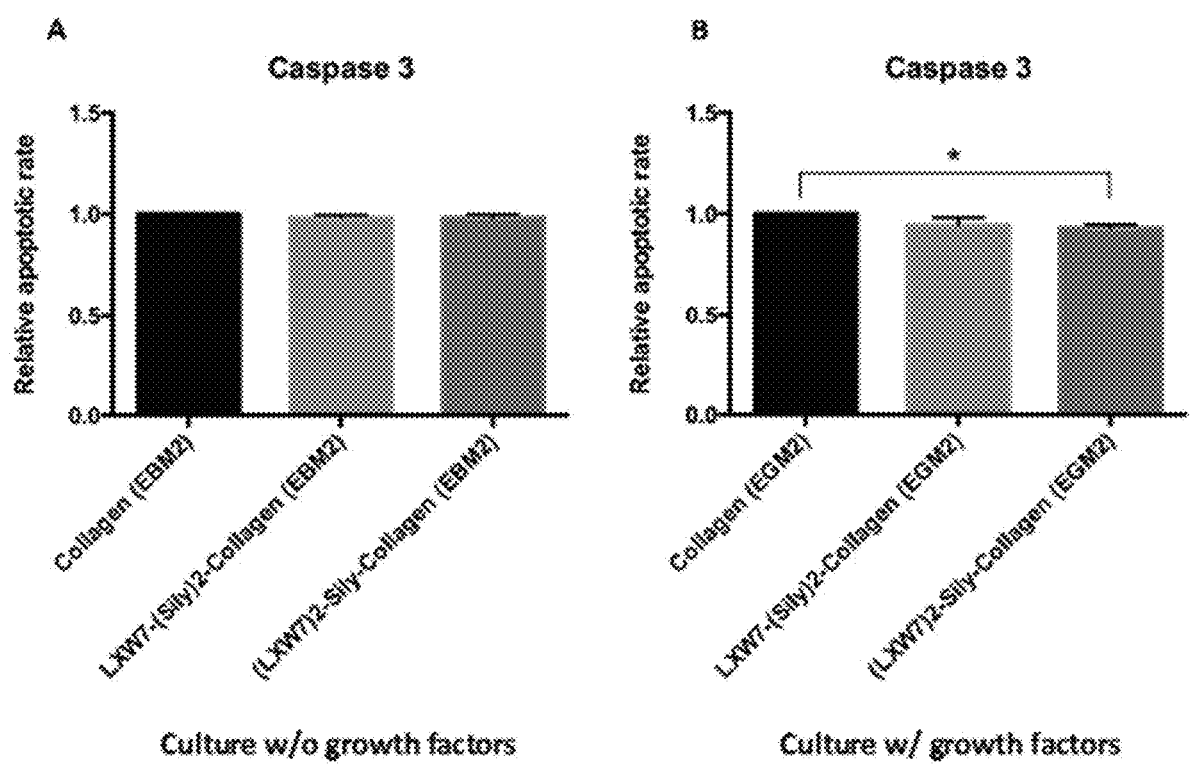
FIG. 8 presents graphs of the effect of LXW7-SILY on EC apoptosis induced by hypoxia.

As shown in FIG. 8, compared with collagen surface without modification, HECFCs cultured in EGM2 medium (in presence of VEGF) on LXW7-(SILY)2 or (LXW7)2-SILY modified collagen surface showed lower Caspase 3 activity. (LXW7)2-SILY modification showed significant lower Caspase 3 activity compared with the control collagen surface without modification.

Example 9. EC Attachment on SIS Scaffold with LXW7-SILY

Figure 9:
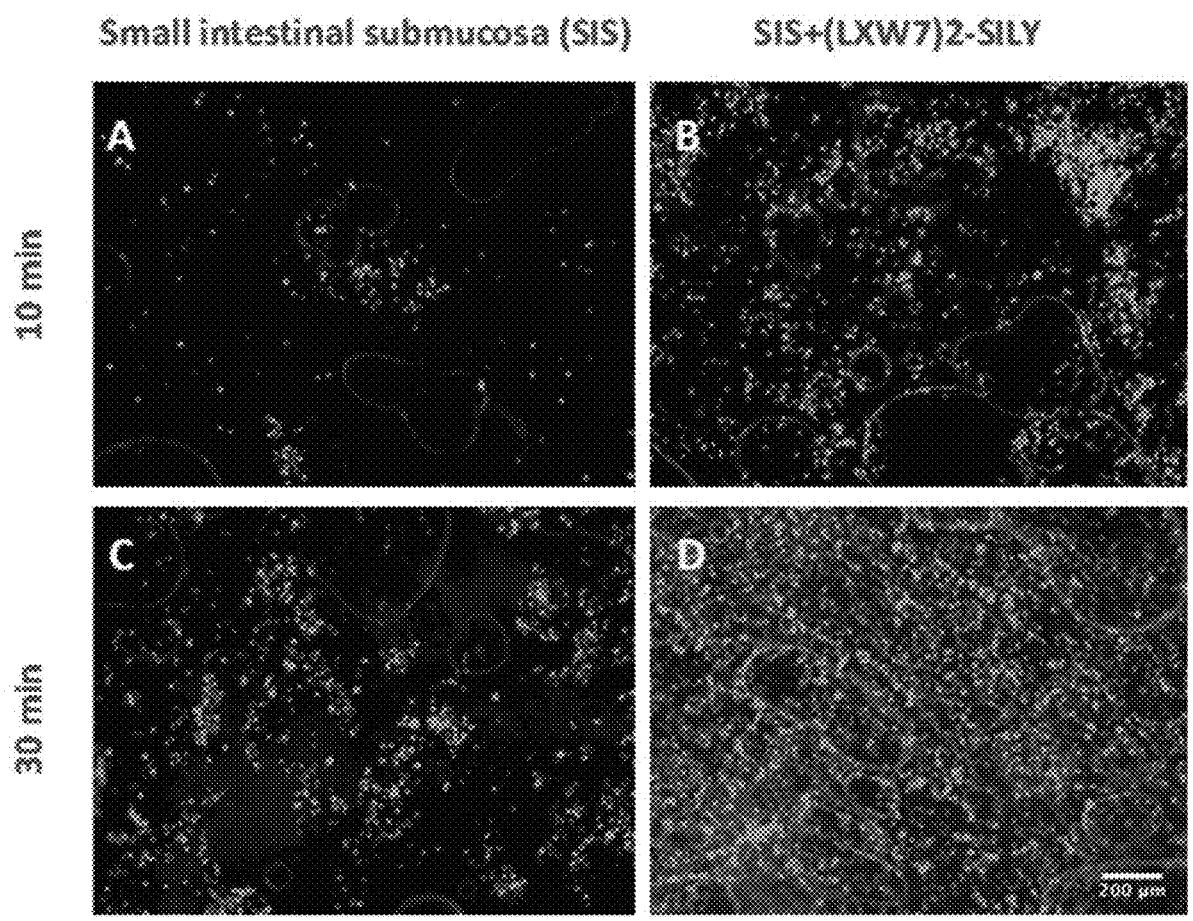
FIG. 9 presents images of EC attachment on SIS scaffold with LXW7-SILY.

SIS scaffolds were cut by 12 mm biopsy punch and incubated with DPBS or 50 µM (LXW7)2-SILY for 3 hours at 37° C. respectively. The scaffolds were then rinsed 3 times with DPBS. Onto the scaffolds were added 2×10$^5$ HECFCs transduced with a GFP reporter suspended in 15 µL EGM-2 growth medium, and the scaffolds were incubated for 10 minutes or 30 minutes at 37° C. and 5% $CO_2$, respectively. The scaffolds were washed 3 times with DPBS to wash off all the unattached cells, and the SIS/cell constructs were imaged using an Olympus IX81 microscope. As shown in FIG. 9, at both 10 minutes and 30 minutes after cell seeding, SIS scaffolds modified with (LXW7)2-SILY (B, D) showed more attached HECFCs on the surface than on the unmodified SIS scaffolds (A, C).

Figure 10:
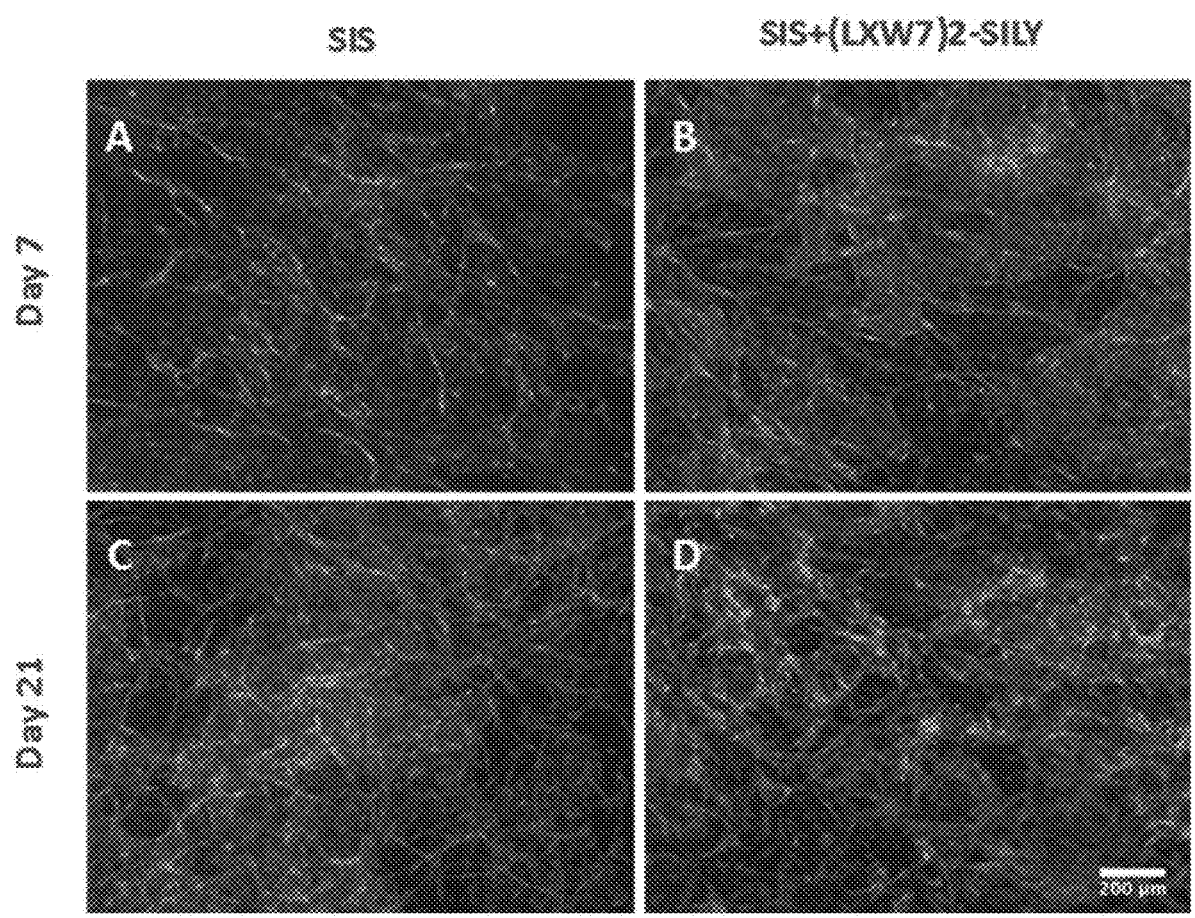
FIG. 10 presents images of EC proliferation and organization on SIS scaffolds modified with LXW7-SILY.

Example 10. EC Proliferation and Organization on SIS Scaffolds Modified with LXW7-SILY SIS scaffolds were cut by 12 mm biopsy punch and incubated with DPBS or 50 µM (LXW7)2-SILY for 3 hours at 37° C. respectively. The scaffolds were then rinsed 3 times with DPBS. Onto the scaffolds were added 2×10$^5$ HECFCs transduced with a GFP reporter suspended in 15 µL maintenance medium, and the scaffolds were incubated for 1 hour at 37° C. and 5% $CO_2$ and added with 1 ml of EGM in each culture well. The scaffolds with cells were cultured at 37° C. and 5% $CO_2$ for 7 days or 21 days respectively, and imaged using an Olympus IX81 microscope. As shown in FIG. 10, compared with SIS scaffolds with modification (A, C), SIS modified with (LXW7)2-SILY supported more rigorous endothelial cell population and denser vasculature (B, D).

Example 11. Synthesis of Pro-Angiogenic and Collagen-Binding Peptide-Hydrazides

Modified pro-angiogenic peptide-hydrazides of QK and LXW7 and collagen-binding peptide-hydrazide SILY having sequences shown in Table 1 were synthesized. The sequences of Table 1 are in 1-letter amino acid format from N to C terminus, where upper case letters indicate L-amino acids and lower case letters indicate unnatural D-amino acids, Ac indicates acetylation of the N terminus, and aeea is a short (2-(2-aminoethoxy)ethoxy)acetic acid spacer (ChemPep, Inc.) resembling PEG$_2$.

TABLE 1

Peptide sequences

| Peptide Name | Sequence | Chemical Formula | Molecular Weight (g/mol) |
|---|---|---|---|
| QK | Ac-KLT WQE LYQ LKY KGI-amide | | 1952.2 |
| VEGFp | KLT WQE LYQ LKY KGI GSG-hydrazide | $C_{99}H_{156}N_{26}O_{26}$ | 2126.5 |
| Peg2V | KLT WQE LYQ LKY KGI-(aeea)$_2$-GSG-hydrazide | $C_{111}H_{278}N_{28}O_{32}$ | 2416.8 |
| LXW7 | cG RGD dvc-(aeea)$_2$-WG-hydrazide | $C_{54}H_{84}N_{18}O_{20}S_2$ | 1369.5 |
| SILY | RRA NAA LKA GEL YKS ILY GSG-hydrazide | | 2252.6 |

A 2-chlorotrityl chloride resin (1.51 mmol/g, Anaspec) was rinsed sequentially 3 times with DMF, DCM, and DMF, and then swollen in 50% DCM/DMF for 1 hour. The resin was then reacted with 10% hydrazine hydrate (85%, Sigma) in synthesis grade DMF (Fisher) and 0.057 M DIPEA (Fisher) for 2 hours at room temperature while bubbling under nitrogen. The solution was drained and the resin was reacted again with fresh solution for 1 more hour, after which the resin was washed 3 times with DMF and reacted with 10% methanol in DMF to cap any remaining unreacted chloride groups. The hydrazide-resin was washed again 3 times with DMF and then reacted directly with the first amino acid (4 equivalents) with HOBt/HBTU (4 equivalents) and DIPEA (10 equivalents) bubbling under nitrogen overnight at room temperature. After coupling, resin was washed thoroughly with 2× DMF, 2×DCM, IPA, and then 2×DMF. Subsequent amino acids were coupled for 20 minutes to 1 hour each at 50° C. on a Liberty Blue automated microwave peptide synthesizer (CEM) using 5 equivalents each of Fmoc-amino acids (Aapptec), DIC, and OxymaPure with 0.1M DIPEA and deprotected with 20% piperidine in synthesis grade DMF for 3 minutes at 60° C. For N-terminal biotinylation, 5 equivalents of D-biotin (Anaspec) was coupled with 4 equivalents HBTU/HOBt and 10 equivalents DIPEA overnight at room temperature. Peptides were cleaved for 3 hours with 88% TFA, 5% phenol, 5% $H_2O$, and 2% TIPS and precipitated with cold diethyl ether. Crude peptides were redissolved in 5% acetonitrile and purified to >90% purity through a C18 prep column (Spirit) against an acetonitrile (HPLC grade) gradient on an AKTApure 25 FPLC (GE Healthcare) and confirmed by MALDI-TOF mass spectrometry (Bruker). Before purification, cyclization of LXW7 was performed by oxidizing cysteine residues to form intramolecular disulfide bridges with ClearOx resin (Peptides International) according to the manufacturer's protocol.

Example 12. Peptide-Hydrazide Conjugation to Dermatan Sulfate

Carboxylic acids on dermatan sulfate (Celsus Laboratories, average MW ~46275) were activated with premium grade EDC (Thermofisher) for 5 minutes in 0.1 M MES buffer with 8 M urea titrated to pH 4.5. Peptide-hydrazides were pre-dissolved in reaction buffer before addition to the activated DS solution with a final DS concentration of 10 mg/mL. After 2 to 48 hours, the reaction was stopped by titrating to pH 8 with 0.5 M NaOH for 30 minutes. The product was then purified by size-exclusion through 2 desalting columns (10-mL Bio-gel P6 desalting cartridges, Bio-Rad) in series on an AKTA purifier FPLC (GE Healthcare) and then lyophilized. For constructs with two different peptides, peptides were reacted sequentially with more EDC added upon conjugation of the second peptide, after taking a small sample of the reaction to quantify addition of the first peptide. Biotinylated molecules for detection of surface binding were similarly synthesized by sequentially conjugating 1 equivalent of biotinylated peptide followed by the desired equivalents of non-biotinylated peptide, taking into account conjugation efficiency. For example, a biotinylated DS-SILY4 was synthesized by reacting 1 equivalent of biotinylated-SILY-hydrazide followed by 4 equivalents of SILY-hydrazide; a biotinylated DS-peg2V2 was synthesized by reacting 1.33 equivalents of biotinylated-peg2V-hydrazide followed by 4 equivalents of peg2V-hydrazide. DS control molecules were also synthesized by reacting DS under the same experimental conditions with and without EDC, labeled "EDC-activated DS" and "processed DS, no EDC" respectively, for 24 hrs but without peptide. These products were also purified by size-exclusion to remove buffer salts and any unreacted EDC.

Example 13. Characterization of Conjugated Peptides

All peptides were detected by concentration-dependent 280 nm absorbance of aromatic amino acids on a NanoDrop One UV-Vis spectrophotometer (ThermoFisher). For increased specificity on molecules with multiple peptides, peptide quantification was confirmed by detection of intrinsic tryptophan (excitation at 295 nm, emission at 350 nm) and tyrosine (excitation at 280 nm, emission at 305 nm) autofluorescence on a SpectraMax M5 plate reader (Molecular Devices) in UV transparent 96-well plates (Corning). All samples were prepared at 2 mg/mL in ultrapure water and analyzed by taking the average of 5 repeated readings.

Circular dichroism spectra of peptides at 21.8 µM and constructs with equivalent total peptide concentrations were collected at room temperature in 0.01 M potassium phosphate buffer (pH 7.1) from 185 nm to 260 nm with 4 accumulations at 50 nm/minute scan speed and 4 seconds DIT in 1-mm quartz cuvettes (Starna) on a Jasco J-1500 CD Spectrophotometer. CD data was converted and presented as molar ellipticity in deg×cm$^2$/dmol, $[\theta]=100*\theta/(C\times l)$, where $\theta$ is the degrees ellipticity, C is the molar concentration, and l is the pathlength in cm. CD spectra of conjugated peptides were calculated by collecting the spectra of the DS-peptide constructs and then subtracting out the signal for an equivalent concentration of EDC-reacted DS.

Two-dimensional nuclear magnetic resonance data were obtained in the form of high resolution 1H, 13C, and HSQC NMR spectra of 45 mg/mL dermatan sulfate in $D_2O$ acquired for 6 hours on a Bruker instrument. Nanodrop absorbance spectra were obtained with 2 mg/mL samples evaluated by absorbance spectral sweeps from 220 nm to 350 nm acquired on a NanoDrop One Spectrophotometer (ThermoScientific).

Example 14. LXW7-DS-SILY and LXW7(SILY)2 Effect on Platelet Binding Under Flow Flow kits from Ibidi (Martinsried, Germany) were used to measure endothelial recruitment under flow conditions. Microchannels were coated with equine fibrillar type I collagen (Chronolog, Havertown, Pa.) diluted in 0.85% sodium chloride and incubated for one hour at room temperature. Unbound collagen was removed by rinsing three time with 1×PBS. The treatment molecule (DS-SILY, LXW7-DS-SILY, or LXW7-(SILY)2) was incubated in the channel for 30 minutes at room temperature, and unbound peptidoglycan was rinsed with 1×PBS.

Human microvascular endothelial cells purchased from Lonza were pushed through channels at a concentration of 6-8×10$^5$ cells/mL by a syringe pump at 2.3 µL/min. for a shear rate of 25 s$^{-1}$. After 30 minutes of flow, channels were rinsed with 100 µL PBS to remove unbound cells. Adherent cells were stained with 10 µM CellTracker Green (ThermoFisher Scientific) in media for 30 minutes at 37° C. Channels were rinsed with 1×PBS and total fluorescence and cell number in the channels were quantified using ImageJ (NIH, Bethesda, Md.).

Next, 15 mL of blood was drawn into sodium citrate vacutainers by venipuncture and centrifuged for 20 minutes at 200 Gs and 37° C. and the top layer of platelet-rich plasma (PRP) was collected. A syringe pump was used to flow PRP through microchannels at 4.2 mL/hr for a shear rate of 750 s$^{-1}$. After 4 minutes, the channels were rinsed with 100 µL PBS to remove unbound cells. Adherent cells were stained with 10 µM CellTracker Green (ThermoFisher Scientific) in media for 30 minutes at 37° C. Channels were rinsed with 1×PBS and total fluorescence and cell number in the channels were quantified using ImageJ (NIH, Bethesda, Md.).

Figure 11:
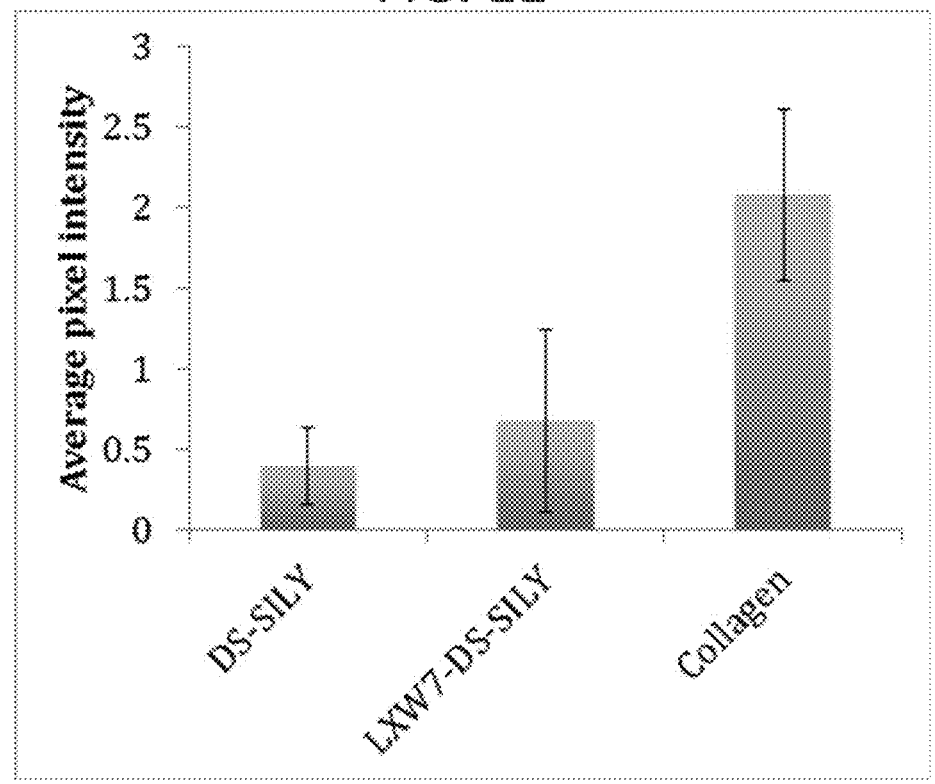
FIG. 11 presents a graph of platelet binding with LXW7-DS-SILY.
Figure 12:
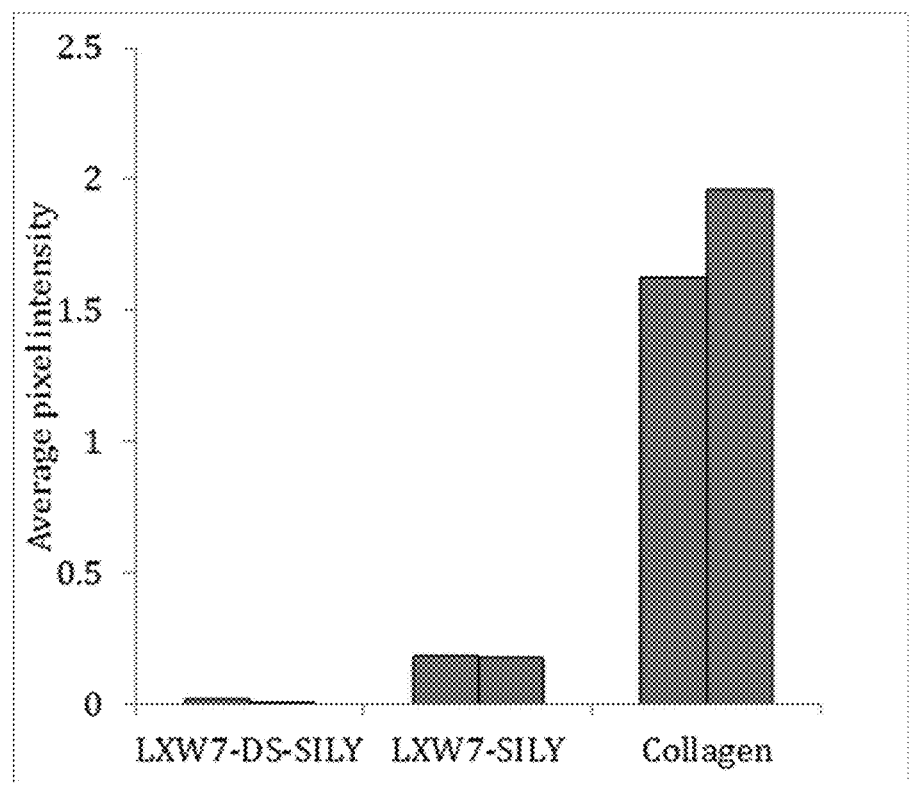
FIG. 12 presents a graph of platelet binding with LXW7-(SILY)$_2$.

The results are presented in the graphs of FIG. 11 and. The data of FIG. 11 demonstrates that LXW7-DS-SILY retains low platelet binding of DS-SILY. The data of FIG. 12 demonstrates that LXW7-(SILY)2 (without DS) retains low platelet binding, but DS further reduces binding.

Example 15. Characterization of Molecule Binding to Collagen-Coated Surfaces High-binding 96-well plates (Corning) were coated with 50 µg/mL rat tail collagen I (Corning) at 4° C. overnight or 2% reduced growth factor Matrigel (Corning #354230) in basal EBM media for 30 minutes at 37° C. and rinsed 3× with PBS before blocking non-specific binding with 1% Bovine Serum Albumin (BSA) for 1 hour at room temperature. For fibrinogen surfaces, a fibrinogen coating solution of ~2.75 mg/mL fibrinogen (Sigma) and 5.5 µg/mL aprotinin (Sigma) was incubated at 4° C. overnight in high-binding plates. Biotinylated samples dissolved in 1% BSA were allowed to bind to the surface for 30 minutes at 37° C. on a plate shaker. After 3 washes with PBS, wells were incubated with 1:200 streptavidin-HRP in 1% BSA, rinsed 3× with PBS, developed with a 1:1 A to B color solution for 20 minutes, stopped with the addition 2N $H_2SO_4$, and read on a Spectramax M5 platereader for absorbance at 450 nm with 540 nm correction.

Example 16. Cell Culture

Human Dermal Microvascular Endothelial Cells (HMVEC, Lonza CC-2543) and Human Umbilical Vein Endothelial Cells (HUVEC, Lonza CC-2935) were expanded according to the manufacturers' protocol in EGM2-MV media and EGM-Plus media, respectively, and passaged at 70-90% confluence. Cells were cryopreserved in 80% media, 10% sterile DMSO, and 10% FBS. For experiments, HMVECs were used between passages 6 and 8, and HUVECs were used between passages 3 and 6 and maintained at 37 C and 5% $CO_2$.

Example 17. Endothelial VEGFR2 Activation

HUVECs or HMVECs were seeded at 20000 cells per well in complete EGM-Plus growth media or complete EGM2-MV, respectively. Approximately 24 hours after plating, the media was replaced with serum-free, growth factor-free basal media (EBM) to serum-starve and synchronize the cells. The next day, the media was replaced with treatments dissolved in EBM for 5 minutes and then immediately lysed with 50 µL per well of complete lysis buffer for 30 minutes on ice. Lysates were frozen at −80° C. until further analysis for phosphorylated VEGF receptor 2 and total VEGF receptor 2 using a custom ELISA-type Multiplexed MesoScale Discovery (MSD) assay performed according to the manufacturer's protocol.

Example 18. Endothelial Proliferation in Response to Soluble Molecules

HMVECs were seeded at 2000 cells per well in a CELL-BIND® 96-well plate (Corning) using complete EGM-2MV media. After 24 hours, media was replaced with EBM (serum and growth-factor free) for 4 hours and then replaced with treatments dissolved in EGM-2MV media lacking VEGF or lacking both FGF and VEGF. After 24 or 72 hours, proliferation was evaluated by an endpoint MTS assay (CELLTITER 96® AQueous One Solution, Promega), by adding 10 µL of 3-(4,5-dimethylthiazol-2-yl)-5-(3-carboxymethoxyphenyl)-2-(4-sulphophenyl)-2H-tetrazolium (MTS) inner salt reagent to each well, incubating for 4 hours at 37° C., and then measuring absorbance at 490 nm.

Example 19. Endothelial Proliferation in Response to Soluble Molecules

50 µL treatments dissolved in 1% BSA in PBS were added to a Biocoat Collagen I 96-well plate (Corning) and incubated for 30 minutes at 37° C. before washing 3 times with PBS to remove unbound treatment. HMVECs were then seeded in either EGM2-MV media or EGM2-MV media without VEGF at a density of 1500 cells per well (low cell density) of 8000 cells per well (high cell density). To evaluate initial attachment, media was aspirated 5-8 hours after seeding and exchanged with alamarBlue® cell viability reagent (1:10, 110 µL/well, Molecular Probes) and incubated for 2.5 hours at 37° C. according to the manufacturers' protocol. 100 µL from each well was pipetted into a new plate and assayed for fluorescence at 560 nm excitation and 590 nm emission. Remaining reagent was aspirated and replaced with fresh media and the alamarBlue® viability assay was performed every 2 days thereafter for 1 week. To control for initial differences in HMVEC attachment, proliferation data is presented as the alamarBlue® fluorescence signal normalized to the signal at 8 hours.

Example 20. Endothelial Migration

ORIS 96-well plates (Platypus Technologies) were coated with 50 µg/mL human fibrillar collagen I (Chronolog) overnight at 4° C. Wells were rinsed 3× with PBS and left to air dry under UV for 1 hour before inserting ORIS silicone stoppers and seeding HMVECs at 8000 cells per well around the stoppers. Cells were allowed to grow to confluence for 48 hours before a 30 minute incubation with 4 µg/mL mitomycin C (Sigma) to halt proliferation. After removal of ORIS stoppers, cells and the collagen-coated surface were incubated with 10 µM of DS-SILY constructs dissolved in EGM-2MV without VEGF for 15 minutes. The treatments were removed and replaced with growth media (EGM-2MV without VEGF) for 48 hours before staining with 10 µM CellTracker Green (molecular probes) and fluorescent imaging on a Keyence BZ-X700 microscope. Fluorescent images were quantified by pixel area analysis on ImageJ.

Example 21. Endothelial Tubulogenesis

Reduced growth factor Matrigel (Corning) was mixed with treatments on ice to obtain the final desired concentrations (10, 20, and 30 µM) within the gel and distributed to Ibidi angiogenesis µ-slides at 10 µL per well to polymerize at 37° C. for 30 minutes. HMVEC cells were seeded at 7500 cells per well in reduced growth factor media (EGM-2MV lacking FGF, VEGF, and IGF supplements). After 8 hours of incubation, cells were stained with 2 µM calcein AM and imaged on a Keyence BZ-X700 microscope. Image analysis tubule quantification was performed by AngioQuant software with a prune factor of 25 to remove artefacts from cellular debris.

Example 22. Ex Ovo Chick Chorioallantoic Membrane (CAM) Assay

Fertilized Hyline eggs obtained from the Avian Facility at UC Davis were incubated at 37° C. for 72 hours with 6 rotations per day at 80% humidity in a Grumbach egg incubator. On day 3, eggs were cracked open into disinfected weighboats (VWR) and covered with lids from square petri dishes (Fisher), and the embryos developed over a week in the incubator. On day 10, treatments encapsulated in collagen I gels were gently placed on the developing CAM. For experiments involving treatments freely eluting from the collagen gels, 100 µL of gel was polymerized in a 10-mm diameter rubber mold against a sterilized glass slide, and 1 treatment gel and 1 control gel was placed per CAM. The number of vessels in a 2-mm radius immediately surrounding the gel was manually counted in imageJ immediately after placement and 24 hours later to determine changes surrounding vessels. The change in vessels over 24 hours for treatment gels were normalized to the respective change in the control gel on the same developing embryo.

For experiments studying vascular invasion into collagen gels, 30 µL collagen I gels with an embedded 3 mm×3 mm nylon mesh (Fisher) were used. 4-5 gels were placed on each CAM, with 2-3 treatment gels of the same type and 2 blank gels as internal controls to correct for embryo variability. In some embryos, the nylon meshes were dyed to improve visualization of the mesh and vessels growing into the gel. Large (4 cm×10 cm) nylon meshes were dyed by reacting in 226 mL of a 77 mM acetic acid (Sigma) solution with 10 drops of green food coloring (McCormick) or 250 µL of 3 mg/mL Evans blue (Alfa Aesar) at 121° C. for 15 minutes in an autoclave, and then cut to 3 mm×3 mm squares for embedding. Gels were imaged daily through a Dino-Eye AM7025X camera installed on a stereomicroscope; for images more than 2 days after gel implantation, 0.25 mL PBS was pipetted on top of gels to help visualize vessels. On day 16, 0.1 mL of 1 mg/mL RITC-dextran (70 kDa, Sigma) or Evans blue was injected into the CAM vasculature using a 30 G needle, and the membrane was cut away from the embryo and placed in a petri dish for brightfield and fluorescent imaging. To quantify vascularity within the gel between 72-96 hours after gel placement, two independent observers scored each gel for the proportion of grids within the mesh that showed positive vessel growth.

Example 23. Endothelial Monolayer Permeability

Using EGM2-MV media lacking VEGF, HMVECs were seeded onto 3-µm pore 24-well transwell inserts (Corning) at 10,000 cells per insert. The following day, an additional 50,000 cells were seeded to each insert and allowed to grow for another 24 hours. Media was then removed and replaced with 0.5 mL media to the bottom well and 0.1 mL of treatment media to the insert for 10 minutes. Treatment was removed and 0.3 mL of 1 mg/mL RITC-dextran in media was then added to each transwell insert and allowed to permeate for 30 minutes. Sample permeate was then assayed on a SpectraMax M5 plate reader for fluorescence (excitation: 570 nm; emission: 590 nm). RITC-dextran solutions and sample permeates were then aspirated and replaced with another 0.1 mL of treatment media in the transwell insert and 0.5 mL media in the bottom chamber. This procedure was repeated daily over 4 days. Treatments were also compared to inserts with cells removed by rubbing away with a pipette tip to determine the barrier efficacy of the monolayer and the degree of increased permeability.

Example 24. Design of Quantifiable Peptide Hydrazide Sequences with Preserved Post-Conjugation Bioactivity Peptides were synthesized as C-terminal hydrazides to allow preferential C-terminal EDC-conjugation over internal primary amines at low pH. Although unmodified QK and SILY peptides both contain multiple aromatic amino acids facilitating conjugated peptide quantification using 280 nm absorbance and intrinsic autofluorescence, the original LXW7 peptide sequence needed to be further modified by addition of a C-terminal tryptophan for ease of downstream non-destructive quantification. As expected based on greater 280 nm absorbance for tryptophan compared to tyrosine, we found that the 280 nm absorbance method was more sensitive for quantification of QK-derived peptides and LXW7 than SILY. Non-destructive quantification of 2 different sequentially conjugated peptides by analyzing 280 nm absorbance of samples immediately before addition of the second peptide provided adequate substitution estimates under the assumption that the conjugation reaction of the first peptide was complete. We achieved more specific quantification of final peptide substitution on proteoglycan mimics containing both LXW7 and SILY measuring intrinsic autofluorescence of tryptophan (excitation 295 nm, emission 350 nm) and tyrosine (excitation 280 nm, emission 305 nm). For this particular peptide combination, the autofluorescence parameters allowed for specific detection of each peptide without significant signal interference from the other peptide. Quantification of mimics with both QK-derived peptides and SILY was also possible by the autofluorescence method, although the tyrosine signal included contributions from both peptides.

Example 25. Optimization of Peptide-Specific EDC-Hydrazide Conjugation Chemistry In the synthesis process, we discovered that peptide conjugation efficiency (defined as peptide equivalents successfully attached out of total reacted equivalents) to the dermatan sulfate backbone was dependent on the peptide. Coupling of SILY was nearly 100% efficient after 2 hours of reaction, while coupling of QK-derived peptides was only ~70% efficient after a 4 hour reaction and coupling of LXW7 suffered the lowest efficiency at ~35-50% even after 48 hours of reaction and additional EDC. In addition to peptide-specific conjugation efficiencies, we also found that comparable conjugation of SILY equivalents could be achieved with EDC activation of as few as 20% of the available carboxylic acids on DS (assuming approximately 100 carboxylic acids per dermatan sulfate), whereas similar reduction of EDC significantly negatively impacted LXW7 conjugation. Given the vast differences in peptide conjugation efficiencies, it is likely that structural and steric effects affect the chemistry in a sequence-specific manner.

We attempted to improve LXW7 coupling by using linear LXW7 in hopes of reducing steric hindrance during conjugation and cyclizing the peptide after conjugation. However, Ellman's assay revealed significantly fewer free thiols than expected after conjugation and it was determined that the thiols in the linear peptide were consumed through irreversible reaction with EDC. By adjusting several experimental parameters, including lengthening reaction time, better controlling pH, increasing peptide equivalents, and adding more EDC over the course of the reaction, we achieved a maximum of 5.5 cyclized LXW7 peptides per DS. In dual peptide conjugation, we also discovered that the order of peptide addition was crucial to achieving desired peptide substitution. SILY conjugation efficiency drastically decreased to 20-50% when it was added as the second peptide (depending on the identity and quantity of the first peptide), while other peptides appeared to maintain relatively constant conjugation efficiency regardless of addition order; therefore, SILY peptides were added first in a dual peptide conjugation sequence.

Engineered molecules were given the following nomenclature to indicate the type and number of conjugated peptides per DS: DS-(peptide)$_{substitution\ \#}$. For example, a decorin mimic composed of a dermatan sulfate backbone and 4 SILY substitutions per DS is referred to as DS-SILY$_4$; a mimic with 3 peg2V peptides per DS is referred to as DS-(peg2V)$_3$. Pro-angiogenic decorin mimics are indicated as (peg2V)$_{substitution\ \#}$-DS-SILY$_4$ or substitution #LXW7-DS-SILY$_4$ to emphasize the differing degrees of LXW7 substitution on LXW7-DS-SILY$_4$ variants. Degrees of substitution are rounded to the nearest 0.5 for simplicity.

Example 26. Characterization of Free and Conjugated Peptides

Figure 13:
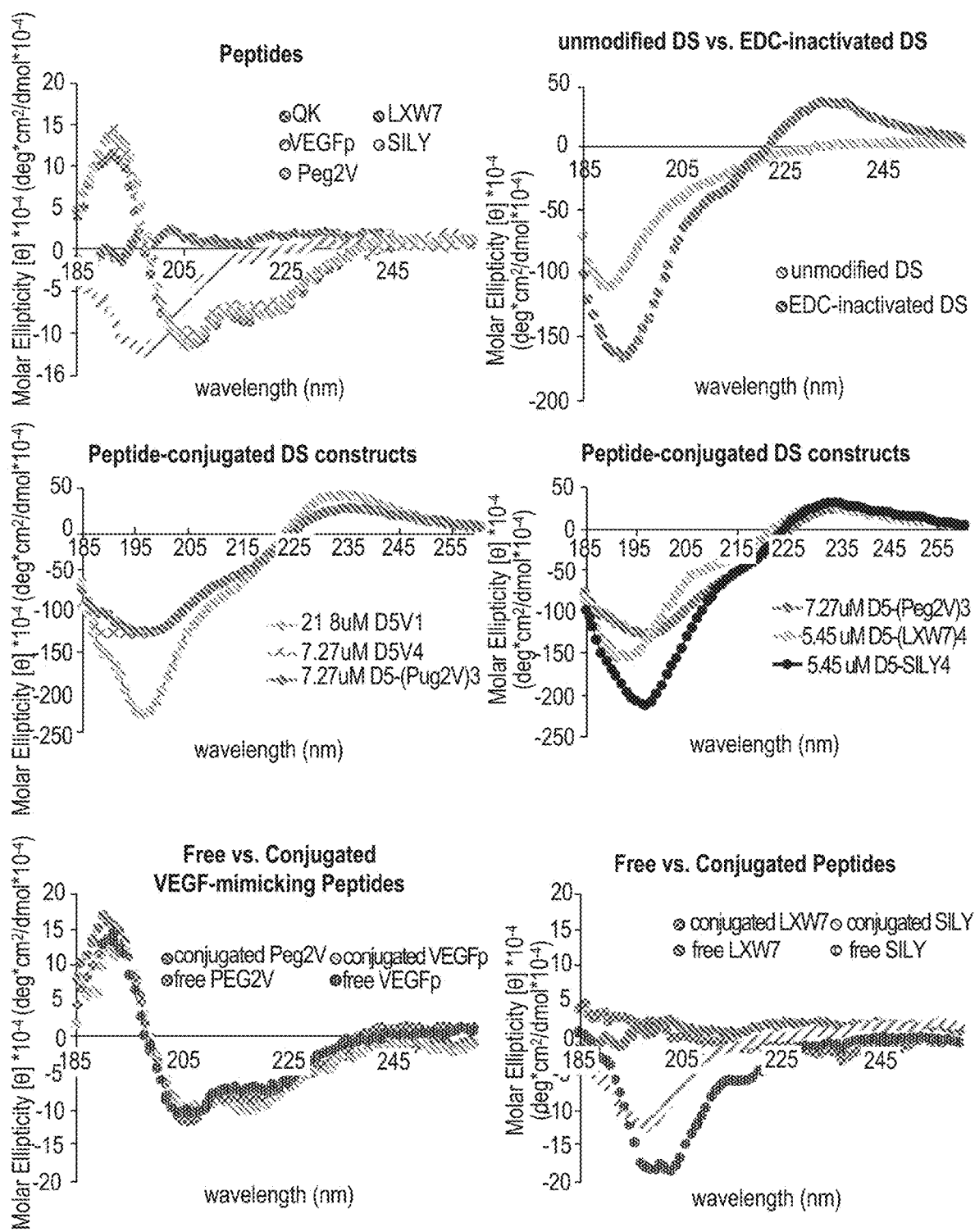
FIG. 13 presents graphs of circular dichroism spectra measured to determine any peptide conformational changes.

Circular dichroism spectra were measured to determine any peptide conformational changes upon spacer and hydrazide C-terminal modifications and upon conjugation to dermatan sulfate. As seen in FIG. 13A, circular dichroism spectra of modified peptides VEGFp and peg2V very closely matched the original alpha-helical QK signature with negative peaks at 208 nm and 222 nm and a positive peak at 193 nm, despite hydrazide modification and the addition of GSG tripeptide and GSG-peg$_2$ C-terminal spacers for VEGFp and peg2V respectively. Importantly, as seen in FIG. 13E, VEGF-mimicking peptides also maintained the alpha-helical CD signature after conjugation to dermatan sulfate, and the differences between the conjugated VEGFp and peg2V CD spectra were minimal; this is an essential finding since the close proximity of the highly negatively charged dermatan sulfate molecule could distort peptide secondary structure. In comparison to the alpha helical structure of VEGF-mimicking peptides, LXW7 had a slight negative signal from 185 to 205 nm and almost no CD signal in other wavelengths examined, while SILY revealed a signature resembling a random coil of a denatured triple-helix with a minimum at 198 nm and low ellipticity above 210 nm. Like free LXW7, conjugated LXW7 also had almost no CD signal, although the minimal signal was slightly positive in the 185 to 205 nm range (FIG. 13F). For SILY peptide, conjugation resulted in a significantly more negative and slightly right shifted spectrum but still lacking a positive signal in the 210 to 230 nm range, perhaps indicative of a slightly more organized collagen-like triple helix (FIG. 13F).

In gathering the CD spectrum of the VEGFp conjugated to DS (denoted DSV), we discovered that lower substitution DSV$_1$ had a greater negative peak around 200 nm than DSV$_3$ (FIG. 13C). This larger negative peak was attributed to a higher concentration of DS, since the DSV$_1$ concentration was 3 times greater than DSV$_3$ in order to match samples for total peptide concentration. Upon background subtraction of the unmodified DS spectra, the resultant curves generally followed the expected alpha-helical features but displayed unexpected positive features in the 225 to 245 nm range. This led us to explore changes in the DS spectra coming from the EDC reaction. In this investigation, we observed an unexpected change in the CD spectra of EDC-reacted DS, indicating a GAG structural/conformational change induced by the EDC reaction (FIG. 13B); the CD spectrum had pronounced deepening of the negative peak around 200 nm and a new positive peak at 235 nm, most closely resembling the CD spectra of intact collagen triple helices although the positive peak is slightly more right-shifted. Since the products were purified by size-exclusion prior to CD analysis, these changes could be attributed to covalent addition of EDC or co-purified EDC due to strong association.

Figure 14A:
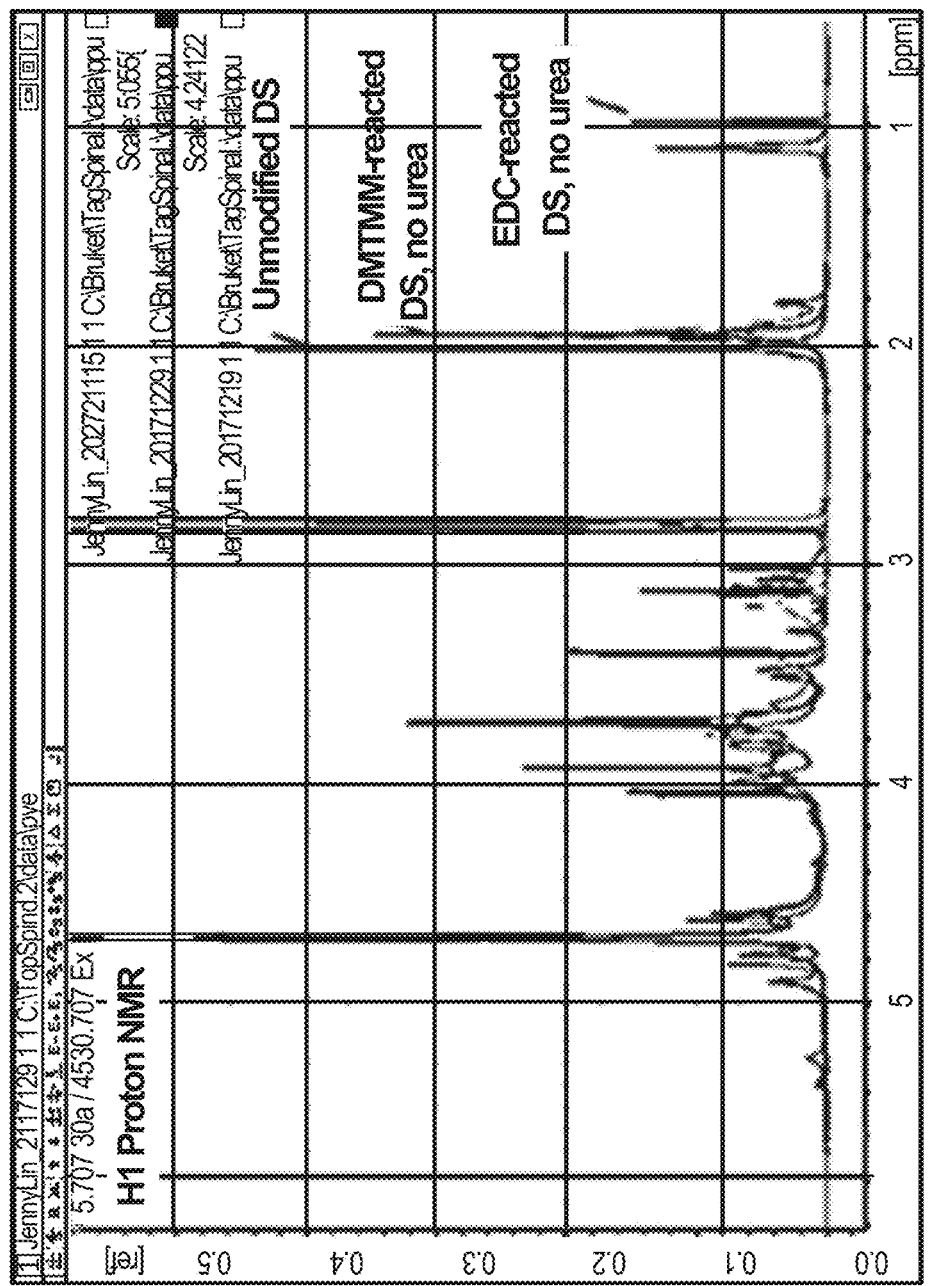
FIGS. 14A and 14B presents graphs of 13C and 1H NMR spectra.
Figure 14B:
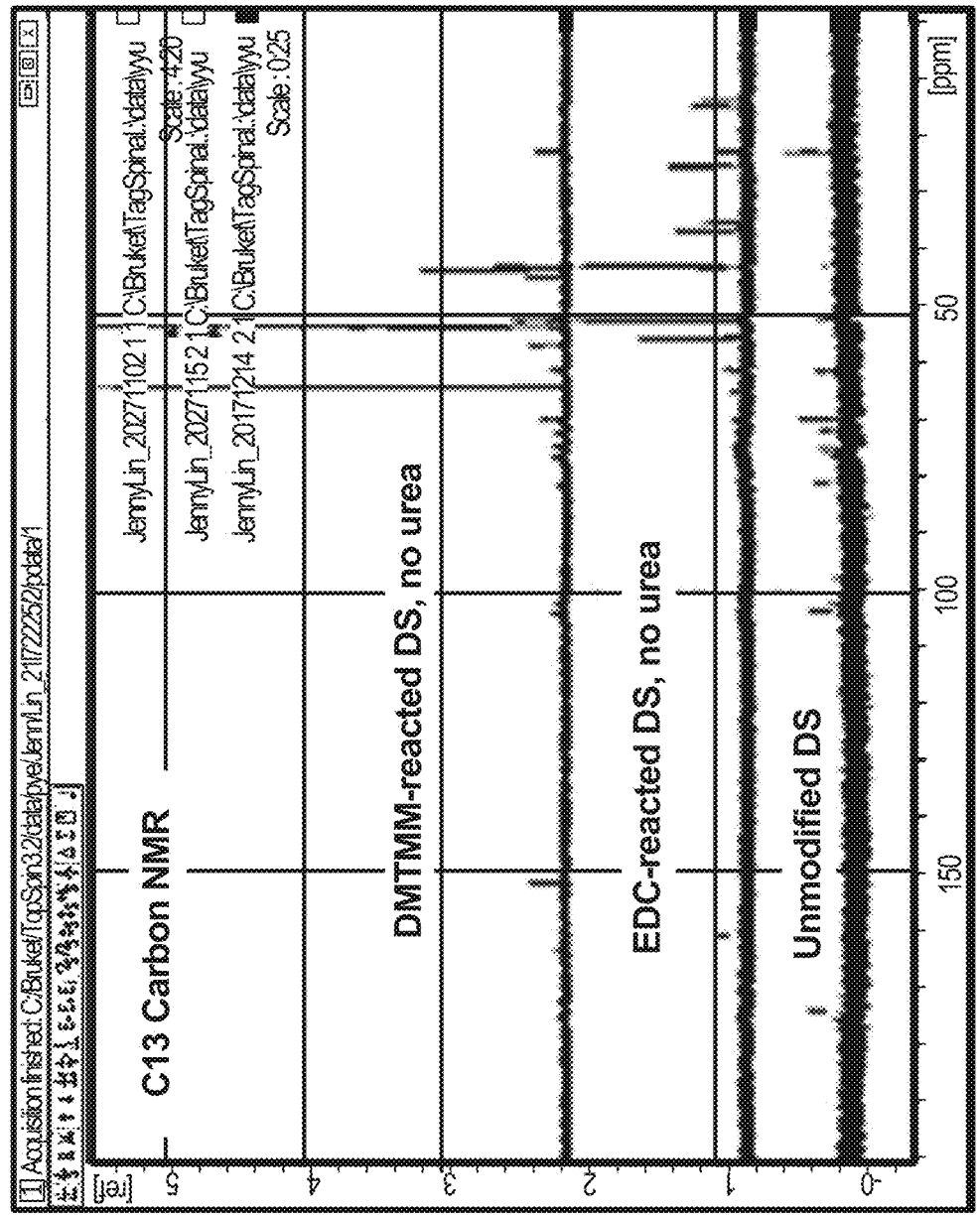
Figure 15:
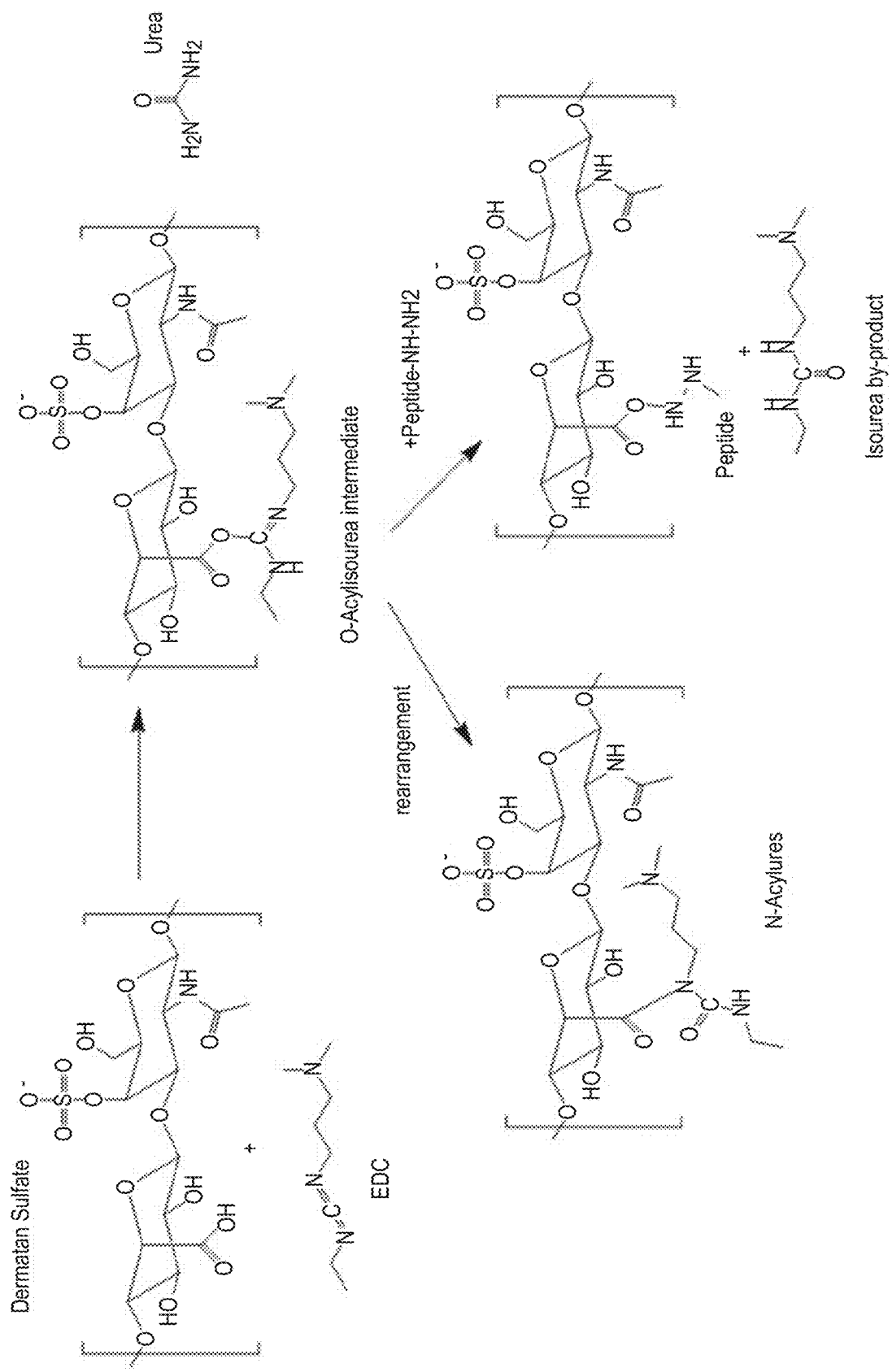
FIG. 15 illustrates the reaction scheme of O-acylisourea rearrangement to stable N-acylurea after carboxylic acid activation.

13C and 1H NMR analysis revealed multiple new carbons and protons on DS after the EDC reaction (FIGS. 14A and 14B). Additionally, absorbance spectral sweeps demonstrated increased absorbance at 220 nm proportional to the amount of reacted EDC, likely due to new imide bonds (resembling amide bonds). The CD, NMR, and absorbance data together indicate that EDC reacted covalently and irreversibly through O-acylisourea rearrangement to stable N-acylurea after carboxylic acid activation (FIG. 15). Irreversible N-acylurea formation with EDC has been well documented, and is likely more abundant in the given reaction due to the lack of NHS although the molar ratio of EDC to carboxylic acid groups was approximately 1:1. Due to modification of the carboxylic acid, the N-acylurea EDC adduct would reduce the overall negative charge on DS at neutral pH and potentially thereby cause a conformational change and affect its electrostatic interactions with other biological molecules.

Example 27. Relative Surface-Binding of Molecules to Various Coated Surfaces The ability of DS-SILY$_4$ to bind to various protein surface coatings was investigated using streptavidin-HRP detection of bound biotinylated DS-SILY$_4$ molecules. Here we studied collagen and fibrinogen binding properties of the proteoglycan mimics since this proposed therapy is designed to target angiogenic activity to the wound site by tethering to extracellular matrix. Using standard surface coating procedures for collagen (50 µg/mL) and matrigel (2%), ~7.5 µg/cm$^2$ rat tail collagen I and ~28 µg/cm$^2$ matrigel were allowed to bind to a high bind plate. Based on Corning's reported composition of matrigel (60% laminin, 30% collagen IV, and 8% entactin), the amounts of collagen I versus collagen IV in the standard coating protocols should be comparable and thus the results of this experiment were assumed to reflect differential binding of molecules to collagen I versus collagen IV and laminin.

FIG. 16A shows that DS-SILY$_4$ bound in a dose-dependent manner to collagen I, collagen IV/laminin, and fibrinogen with binding capacities of 1.6, 1.1, and 0.30 AU respectively. FIG. 16A also shows that binding detection on a plate coated with collagen following our reported protocol was roughly equivalent to the binding on a manufacturer collagen coated plate (Corning Biocoat) up to 1 µM of DS-SILY$_4$. In the ranges of 1 to 10 µM, DS-SILY$_4$ exhibited a negative binding trend on the Biocoat plate, likely resulting from preferential association of DS-SILY$_4$ with itself over the surface at higher concentrations. A similar downward binding trend was also seen for DS-SILY$_4$ on the collagen-coated plate in the 5 to 10 µM range. Differing collagen surface densities may account for these observed differences in binding behavior. Fibrinogen surfaces were exposed to ~400 µg/cm$^2$ fibrinogen. Despite the high coating density, the fibrinogen surfaces exhibited a low level of dose dependent DS-SILY$_4$ binding relative to collagen I and matrigel surfaces (FIG. 16A).

As seen in FIGS. 16A and 16B, peg2V conjugation to DS-SILY$_4$ increased binding to collagen I and matrigel. To determine whether this increase was caused by non-specific binding due to greater peptide substitution or intrinsic collagen I affinity, we studied whether removing the known collagen-binding SILY peptide would still allow for dose-dependent collagen I binding. FIG. 16B reveals that, when conjugated to DS, peg2V does have very high intrinsic collagen I affinity but appears to aggregate more readily at concentrations above 0.5 µM, represented by a significant drop in binding at high concentrations. In fact, between the concentrations of 0.05 to 1 µM, DS-(peg2V)$_2$ had the highest collagen I binding capacity of all the molecules studied. Interestingly, since DS-(peg2V)$_2$ exhibited higher collagen I binding capacity than DS-SILY$_4$, collagen may have more binding sites for peg2V than SILY. This is especially significant given that the addition of only 2 peg2V peptides produced greater binding than 4 SILY peptides. Notably, FIG. 16B also demonstrates that DS-(peg2V)$_2$ has a higher affinity for collagen I than DS-SILY$_4$, while their matrigel binding affinities were similar (FIG. 16C); however it appears that the combination of peg2V with SILY synergistically strengthens binding affinity to both collagen I and matrigel since (peg2V)$_2$-DS-SILY$_4$ demonstrated the highest collagen I and matrigel affinities, with significantly greater binding at lower concentrations <0.05 µM. The data taken altogether suggests that peg2V exhibits specific collagen I binding even greater than SILY, but the simultaneous conjugation of both peptides increases collagen I and IV affinity and reduces molecular aggregation high concentrations.

As seen in FIGS. 16B and 16C, LXW7 conjugation to DS-SILY$_4$ also increased binding to collagen I and matrigel. Taking a different approach to investigating the effects of LXW7 on collagen binding, we compared variants with differing degrees of LXW7 substitution. 3LXW7-DS-SILY$_4$ had greater binding capacity than 1LXW7-DS-SILY$_4$ at all concentrations and both bound collagen I better than DS-SILY$_4$ alone, suggesting that the addition of LXW7 increased collagen I binding sites. From FIG. 16B, addition of LXW7 also improved molecule affinity to collagen I since 3LXW7-DS-SILY$_4$ had significantly greater affinity than 1LXW7-DS-SILY$_4$. Most notably, as seen in FIGS. 16C and 16D, a higher LXW7 substitution also improved collagen I specificity over matrigel since 3LXW7-DS-SILY$_4$ had higher collagen I binding but lower matrigel binding than 1LXW7-DS-SILY$_4$. It is possible that LXW7 does this by more specifically binding collagen I or that it imparts non-specific collagen I binding and simultaneously hinders matrigel binding by unknown mechanisms, but biotinylated DS-LXW7 variants (lacking SILY) were not synthesized to rule out non-specific binding.

To study the deterioration of binding activity over time, we observed surface binding properties of (peg2V)$_2$-DS-SILY$_4$ and DS-SILY$_4$ after 2 weeks in 1% BSA at room temperature (FIG. 16F). Comparing FIGS. 16E and 16F, it is clear that the collagen I and matrigel binding curves shifted after the 2 week incubation such that higher concentrations are needed to achieve the same binding for peg2V2-DS-SILY$_4$. Although this shift was also observed for DS-SILY$_4$ to collagen I interaction, the degraded DS-SILY$_4$ binds matrigel even more than the freshly dissolved treatment. The observed concentration shifts suggest that the effective molecule concentration has decreased after the 2 week incubation, which could be caused by degradation of the full molecule or hydrolysis of the collagen-binding SILY peptide. FIG. 16F also shows that DS-SILY$_4$ had increased matrigel binding capacity after the 2 week incubation, indicating that partially degraded DS-SILY has increased matrigel binding capacity, while its affinity remained constant.

Example 28. HMVEC Attachment to Surface-Bound Molecules

Figure 16:
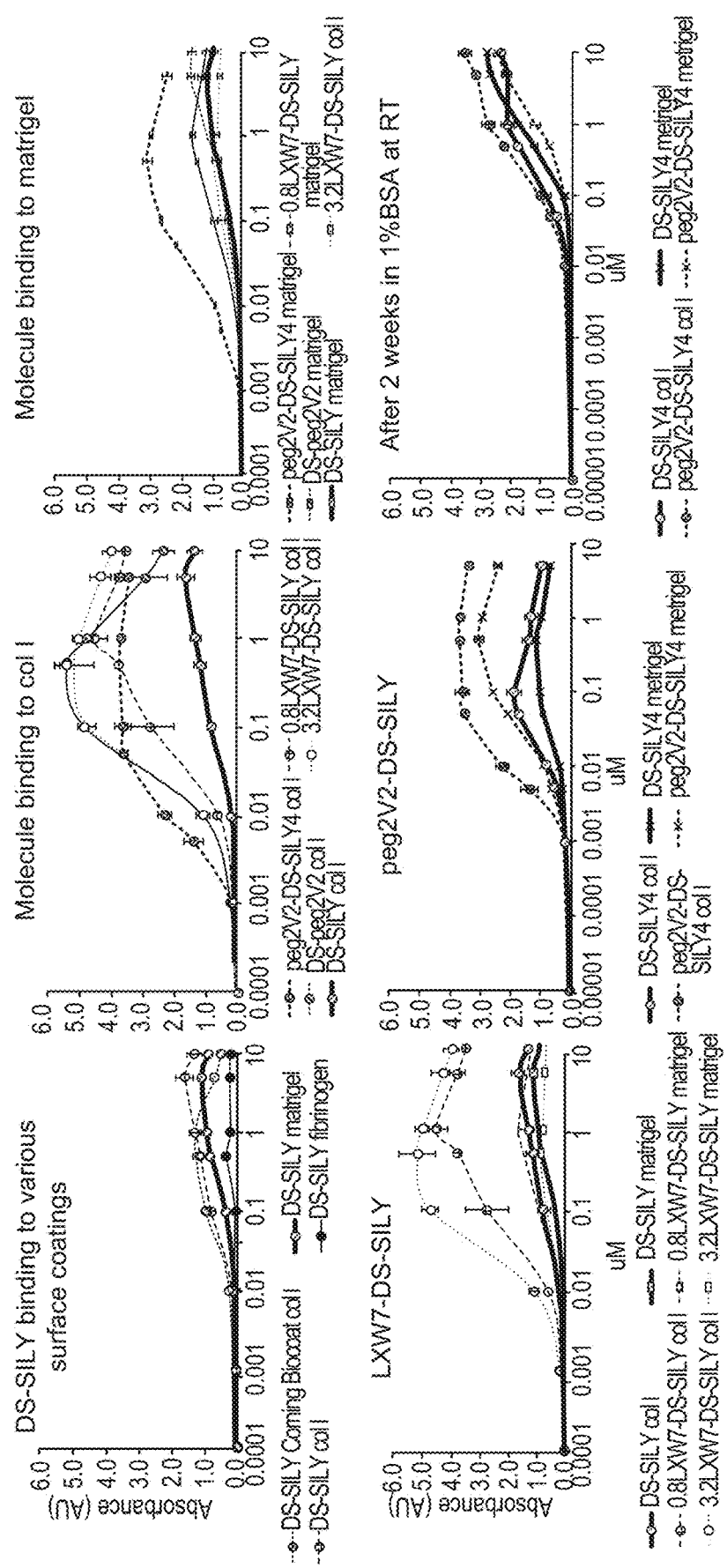
FIG. 16 presents absorbance graphs of binding.
Figure 17:
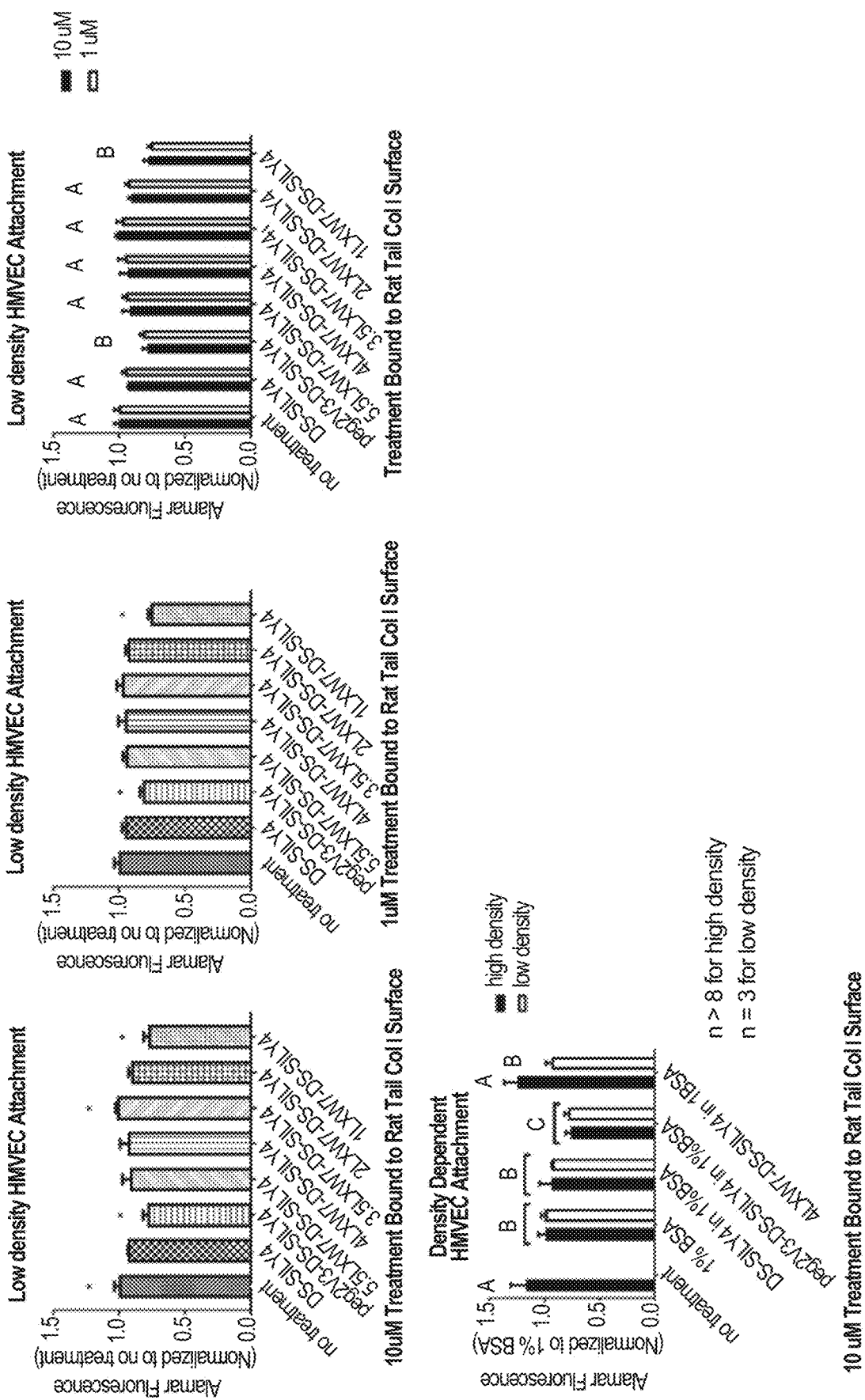
FIG. 17 presents graphs of microvascular endothelial cell adhesion to surface-bound molecules

Microvascular endothelial cell adhesion to surface-bound molecules was studied for its relevance to endothelial recruitment in the wound healing process, with results shown in FIG. 17. At low cell densities, both 1 µM and 10 µM DS-SILY$_4$ surface treatments caused a slight 7% decrease in HMVEC attachment compared to a BSA blocked collagen surface, although the decrease was only statistically significant at 10 µM (asterisks indicate treatments that were statistically different from DS-SILY$_4$ control). Since DS-SILY$_4$ binds and masks collagen fibrils, decreased adhesion is likely due to a decrease in exposed collagen and therefore reduced cell adhesion sites. Surprisingly, both 1 µM and 10 µM (peg2V)$_3$-DS-SILY$_4$ caused an even greater 15% decrease in HMVEC attachment compared to DS-SILY$_4$ alone. This additional decrease could be attributed to increased surface concentrations of peg2V3-DS-SILY$_4$ due to higher surface binding discovered through the binding experiments (FIG. 16), thereby masking the underlying collagen more effectively and further decreasing adhesion sites for cells. Alternatively, it is possible that the peg2V peptide prevents cell attachment by unknown mechanisms.

To determine the effects of LXW7 conjugation on cell adhesion, multiple variants with varying degrees of LXW7 substitution were investigated. A low LXW7 substitution of 1 caused a similarly significant 18% decrease in cell adhesion at both 1 μM and 10 μM concentrations; however, increasing LXW7 substitution caused a trending increase in HMVEC attachment, with the greatest positive effect at 3.5 LXW7. At 1 μM, it appears that a threshold substitution degree of at least 2 LXW7 is required to prevent negative effects on attachment, and all other substitutions tested (2, 4, and 5.5) have no significant effects on attachment at compared to DS-SILY$_4$. At 10 μM, a moderate degree of substitution between 3 and 4 provided optimal attachment significantly greater than DS-SILY$_4$ alone by 8% and comparable to attachment to an untreated collagen I surface blocked with 1% BSA (FIG. 17A). Cell adhesion was similar between the 1 and 10 μM concentrations for all treatments (FIG. 17C). Given the LXW7 peptide's role facilitating cell adhesion through integrin-binding, it was surprising that surface coatings with increased LXW7 substitution beyond 3.5 did not significantly increase cell attachment when cells were seeded sparsely. However, increasing the cell density more than 5 fold was able to reveal these expected increases in cell binding as seen in the 4LXW7-DS-SILY$_4$ variant and restored HMVEC attachment comparable to an unblocked collagen I surface.

Example 29. HMVEC Proliferation Responses to Soluble Molecules (MTS Assay) Vs. Surface-Bound Molecules (Alamar Assay)

Figure 18:
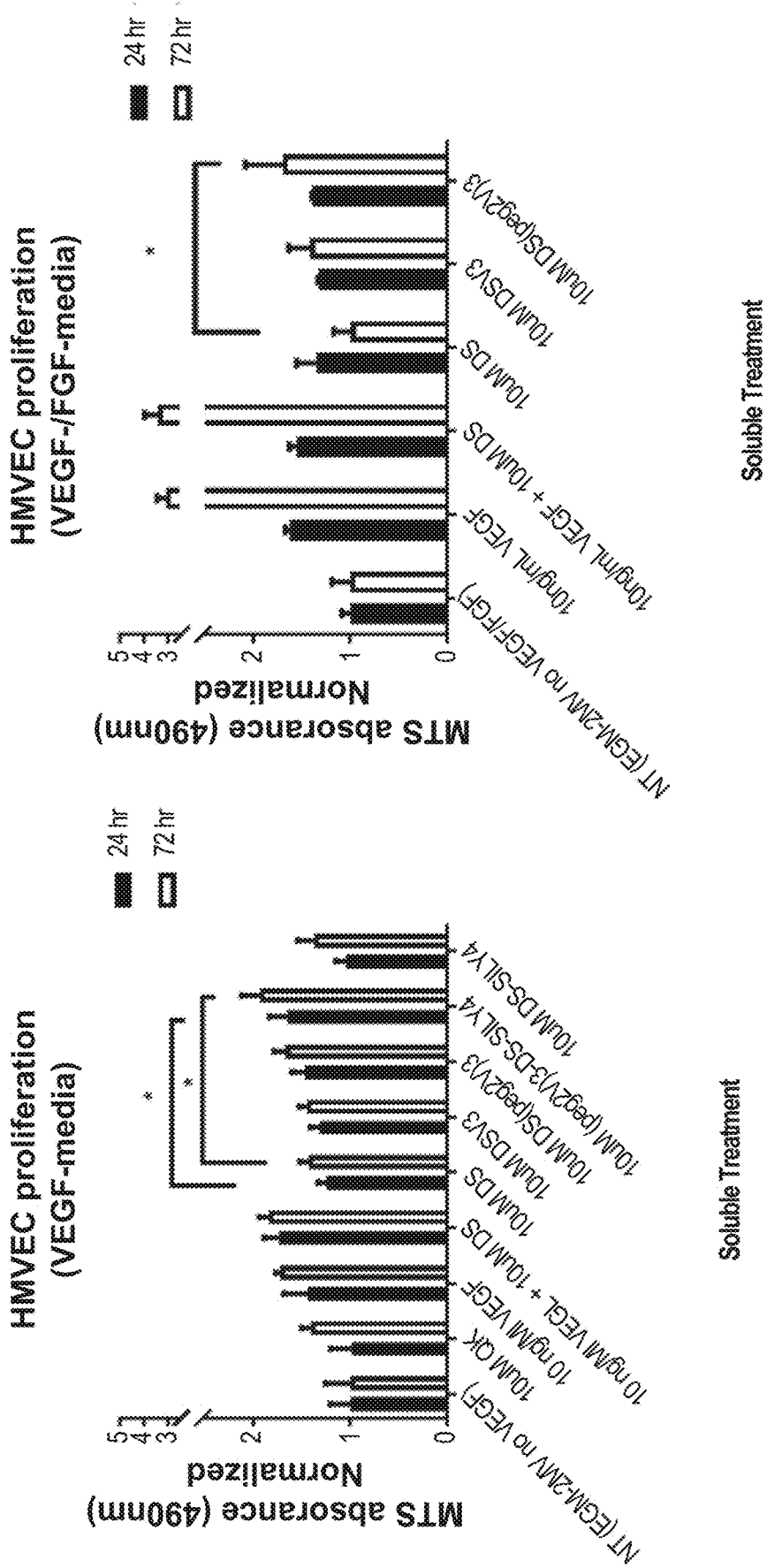
FIG. 18 presents graphs of endpoint MTS metabolic assay results.

Initial investigation of proliferative bioactivity using an endpoint MTS metabolic assay (FIG. 18) revealed a trending increase in HMVEC proliferation in response to constant 24 hour and 72 hour stimulation by 10 μM soluble DS(peg2V)$_3$ and (peg2V)$_3$-DS-SILY$_4$ but not DSV$_3$ when compared to DS alone. The trending increase in bioactivity for DS(peg2V)$_3$ compared to DSV$_3$ suggests that the longer spacer between the active QK sequence and the DS backbone improved the proliferative response, perhaps by allowing better access for peptide binding to the VEGF receptor or by better conserving the alpha-helical secondary structure. Furthermore, since free (peg2V)$_3$-DS-SILY$_4$ in solution would also bind any secreted collagen I and other extracellular matrix molecules to an extent, as seen in the binding experiments (FIG. 16), (peg2V)$_3$-DS-SILY$_4$ may be present at higher local concentrations around the cell when bound and could therefore exert a more potent proliferative response from (peg2V)$_3$-DS-SILY$_4$ in comparison to DS(peg2V)$_3$. Finally, 10 μM soluble DS(peg2V)$_3$ and (peg2V)$_3$-DS-SILY$_4$ also significantly increased proliferation compared to 10 μM soluble DS-SILY$_4$, indicating that the conjugated peg2V peptide was responsible for the proliferative response. Since LXW7-DS-SILY$_4$ variants required surface binding to enact proliferative bioactivity through integrin-binding, the LXW7-conjugated variants were not tested in the soluble proliferation assay.

Both soluble and bound forms of molecules would be present in a dynamic equilibrium in this initial experimental design and the two forms may produce differing effects, and thus we sought to investigate the effects of bound molecules alone. Furthermore, the bioactivity of a collagen-bound form would more directly reflect the application of a targeted pro-angiogenic therapy in a chronic wound. To investigate the effects of surface-bound molecules, collagen surfaces were first incubated with treatments to bind and then washed thoroughly to remove any unbound molecules before seeding and following cell growth every other day for a week with media replenished every other day. To control for differences in initial cell number due to surface effects on cell attachment, signals were normalized to the initial signal 8 hours after seeding.

Figure 19:
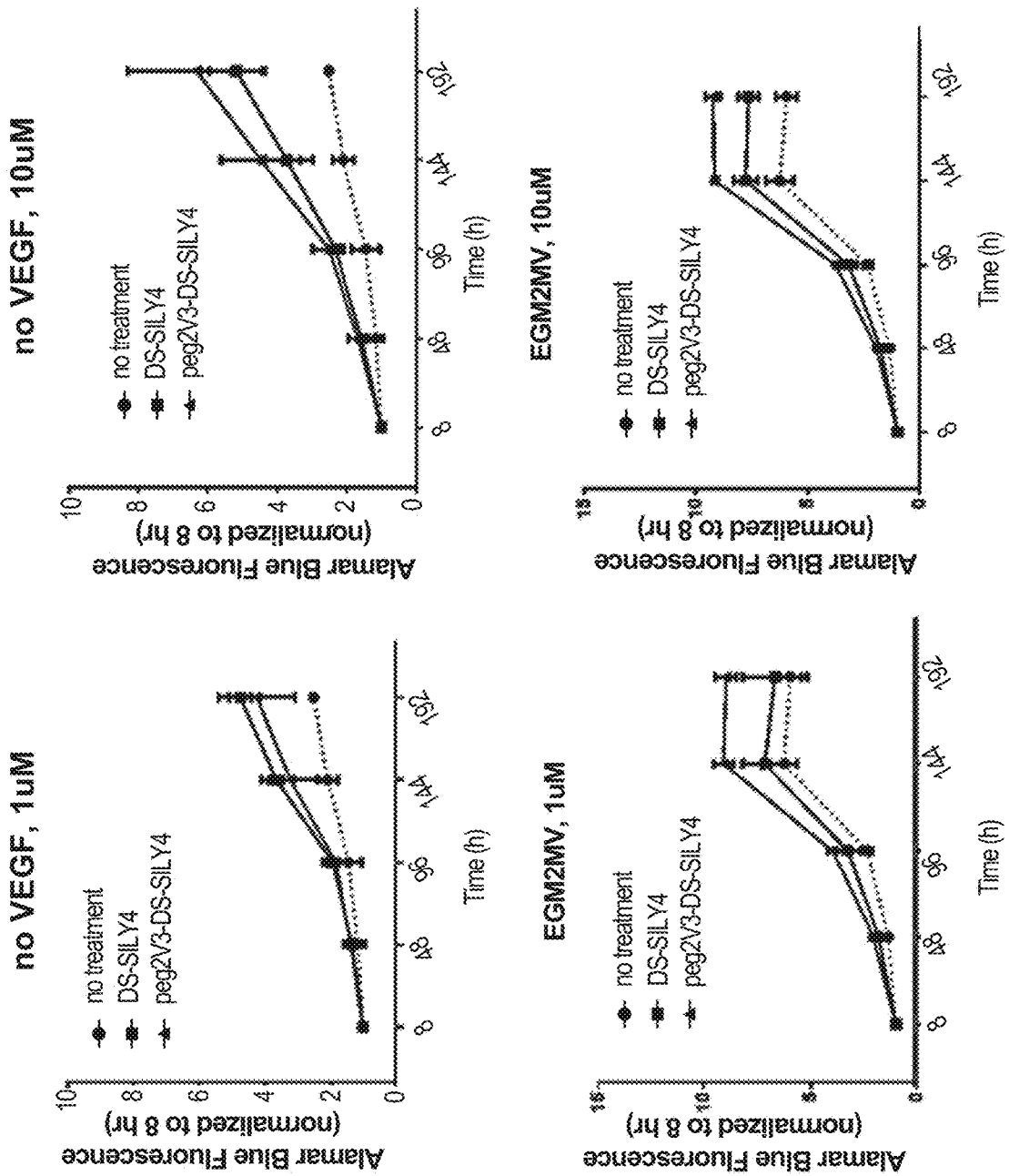
FIG. 19 presents graphs of endothelial proliferation over time for DS-SILY$_4$ and (peg2V)$_3$-DS-SILY$_4$.

From the results shown in FIG. 19, DS-SILY$_4$ surface treatments significantly improve endothelial proliferation compared to untreated collagen alone. The effects of 1 μM DS-SILY$_4$ were only statistically significant over no treatment when compared in media lacking VEGF, but 10 μM DS-SILY$_4$ significantly improved proliferation in media with and without VEGF. The effects of 1 and 10 μM concentrations were very comparable, because although 10 μM DS-SILY$_4$ improved proliferation over 1 μM by day 6 in media with VEGF, 1 μM DS-SILY$_4$ was equally as effective as 10 uM during the first 4 days of growth. The relative similarity between the 1 and 10 μM DS-SILY$_4$ concentrations could be expected given the apparently saturated collagen I-binding plateau found in the surface binding experiments (FIG. 16).

A single peg2V conjugated DS-SILY$_4$ variant was investigated in 2 concentrations to observe proliferative effects. In media lacking VEGF, (peg2V)$_3$-DS-SILY$_4$ did not have any significant proliferative effects, although the higher 10 μM concentration showed a trending improvement in proliferation (FIG. 19A). In contrast, (peg2V)$_3$-DS-SILY$_4$ surface treatment significantly improved proliferation over DS-SILY with VEGF supplementation, indicating an apparent synergistic effect of the conjugated peg2V with VEGF (FIG. 19B). At 1 μM, (peg2V)$_3$-DS-SILY$_4$ surface treatment was as effective as the 10 μM treatment, both resulting in ~9-fold increase after 144 hours of growth; however, the 1 μM more effectively potentiated VEGF activity compared to 10 μM, providing a 27% increase in proliferation over the 1 μM DS-SILY$_4$ control versus an 18% increase over the 10 μM DS-SILY$_4$ control.

Figure 20:
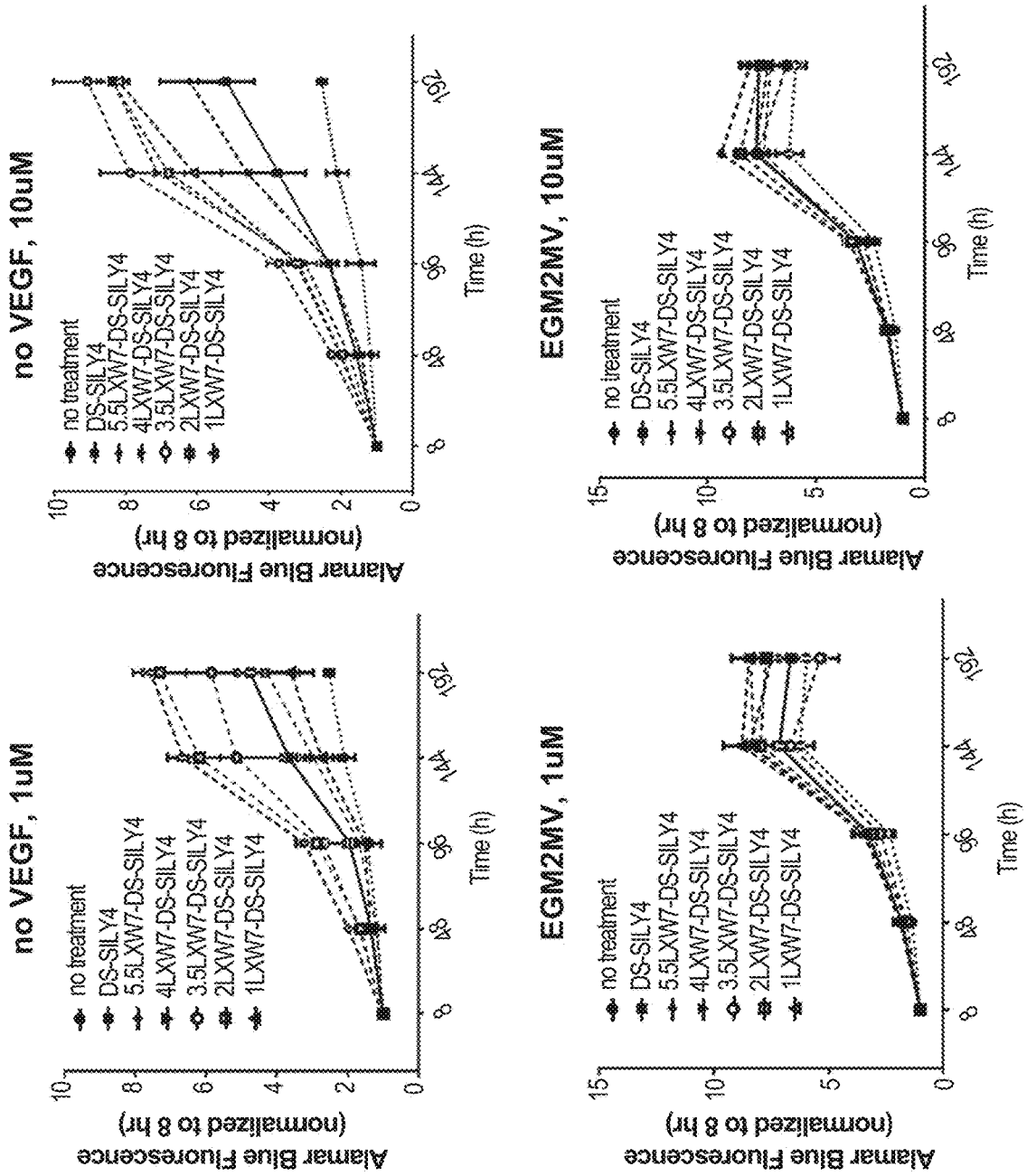
FIG. 20 presents graphs of endothelial proliferation over time for LXW7-DS-SILY$_4$ variants.
Figure 21:
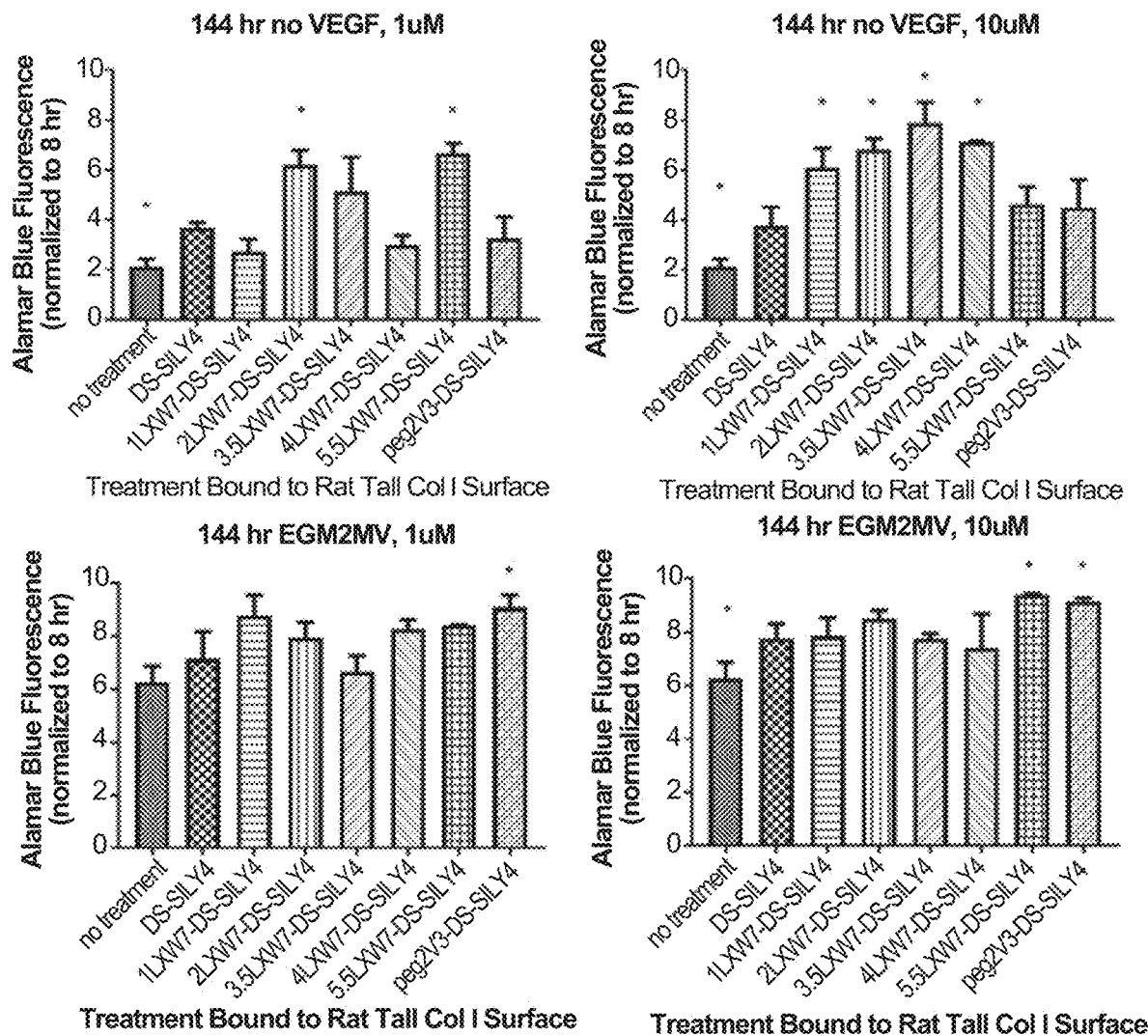
FIG. 21 presents graphs of endpoint results of endothelial proliferation using LXW7-DS-SILY$_4$ variants.

Multiple LXW7-DS-SILY$_4$ variants with differing degrees of substitution were tested to determine the effect of LXW7 density on endothelial proliferation, since the varying surface densities could affect integrin binding conformation and subsequent VEGF receptor clustering and activation. Results are shown in FIGS. 20 and 21. In media lacking VEGF and low 1 μM concentration, HMVECs exhibited a peculiar bimodal proliferative response to increasing LXW7 substitution with peaks at 2-3.5 LXW7 and 5.5 LXW7. However, at 10 μM, all substitutions less than 5.5 resulted in significantly increased HMVEC proliferation with the most significant activity at 3.5 LXW7. Interestingly, these variants were as effective as the 10 ng/mL VEGF supplementation, causing a 6-fold increase in proliferation, and the 3.5 LXW7 variant appeared to be even more effective than 10 ng/mL VEGF (although the increase was not statistically significant). With VEGF supplementation and at low 1 μM concentration, proliferation was greatest at 1 and 5.5 LXW7, but only statistically different than DS-SILY$_4$ when the degree of substitution exceeded 4. Similarly at 10 μM, the effects of degrees of substitution below 5.5 were also statistically equivalent to DS-SILY$_4$, but the 5.5LXW7-DS-SILY$_4$ showed significantly increased HMVEC proliferation over the DS-SILY$_4$ control. Based on this data, LXW7 synergy with VEGF (10 ng/mL based on manufacturers specifications) only appeared to be present for the 5.5LXW7-DS-SILY$_4$ variant, whereas this concentration of VEGF actually seemed to mask the effects of low LXW7 substitution. Taken together, the results indicated that high LXW7 substitution variants were more effective at potentiating VEGF at the 10 ng/mL tested concentration, while lower LXW7 substitution optimal at 3.5 exerted significant proliferative bioactivity without exogenous VEGF. At 1 µM, effects were variable but tended to be most effective around 2 and 5.5 LXW7 in a bimodal manner in media conditions both with and without VEGF. These results suggest that an optimal substitution of approximately 3 LXW7 per DS may promote optimal proliferative bioactivity through integrin clustering.

Example 30. HMVEC Migration Responses to Surface-Bound Molecules (ORIS Assay)

Figure 22:
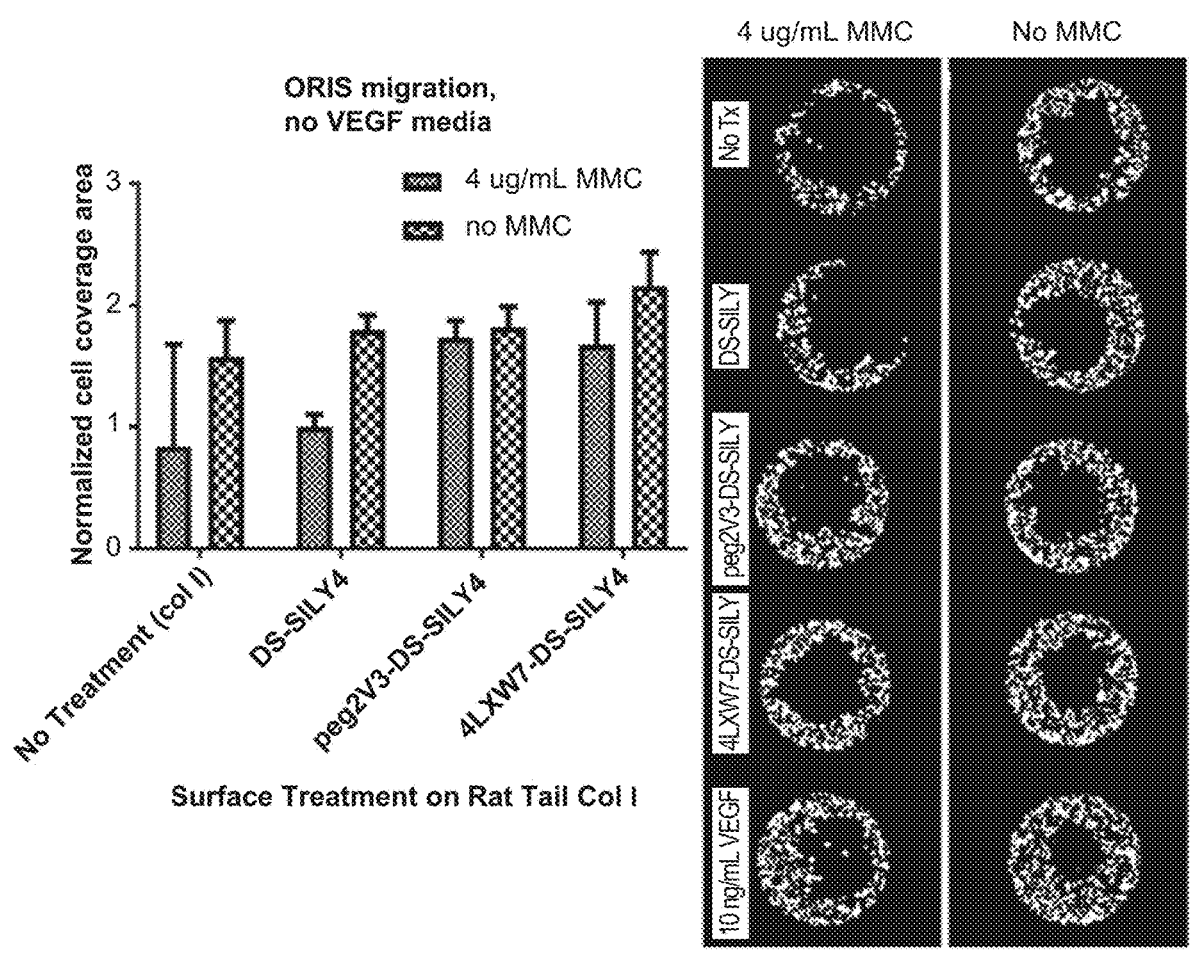
FIG. 22 presents graphs and images of migration responses to surface-bound molecules.

Migration responses were explored with and without the application of the anti-proliferative agent Mitomycin C (MMC) in the ORIS assay to study closure of a circular breach in a confluent endothelial monolayer. When cells were exposed to MMC in the absence of VEGF, Peg2V and LXW7 conjugated to DS-SILY$_4$ both significantly stimulate endothelial migration more than DS-SILY$_4$ alone (FIG. 22). Without MMC treatment, cells appearing in the previously obstructed central region could be attributed to both migration and proliferation over 48 hours; in this scenario, there were no statistically significant differences in cell coverage between the variants, although the 4LXW7-DS-SILY$_4$ stimulated slightly greater cell coverage. Nevertheless, the differences in monolayer closure with and without MMC suggest that the gap closure was mainly due to DS-SILY$_4$ is primarily a proliferative response, while coverage from (peg2V)$_3$-DS-SILY$_4$ was from a migratory response and 4LXW7-DS-SILY$_4$ had important contributions from both migration and proliferation. The migration data without MMC closely matched the observed 48 hour proliferative responses to surface-bound molecules discussed previously in our study; in the absence of VEGF, (peg2V)$_3$-DS-SILY$_4$ stimulated proliferation about the same degree as DS-SILY$_4$ over an untreated collagen surface, while 4LXW7-DS-SILY$_4$ was able to produce a greater proliferative response.

Example 31. HMVEC 2D Tubulogenesis in Response to Matrigel Embedded Molecules

Figure 23:
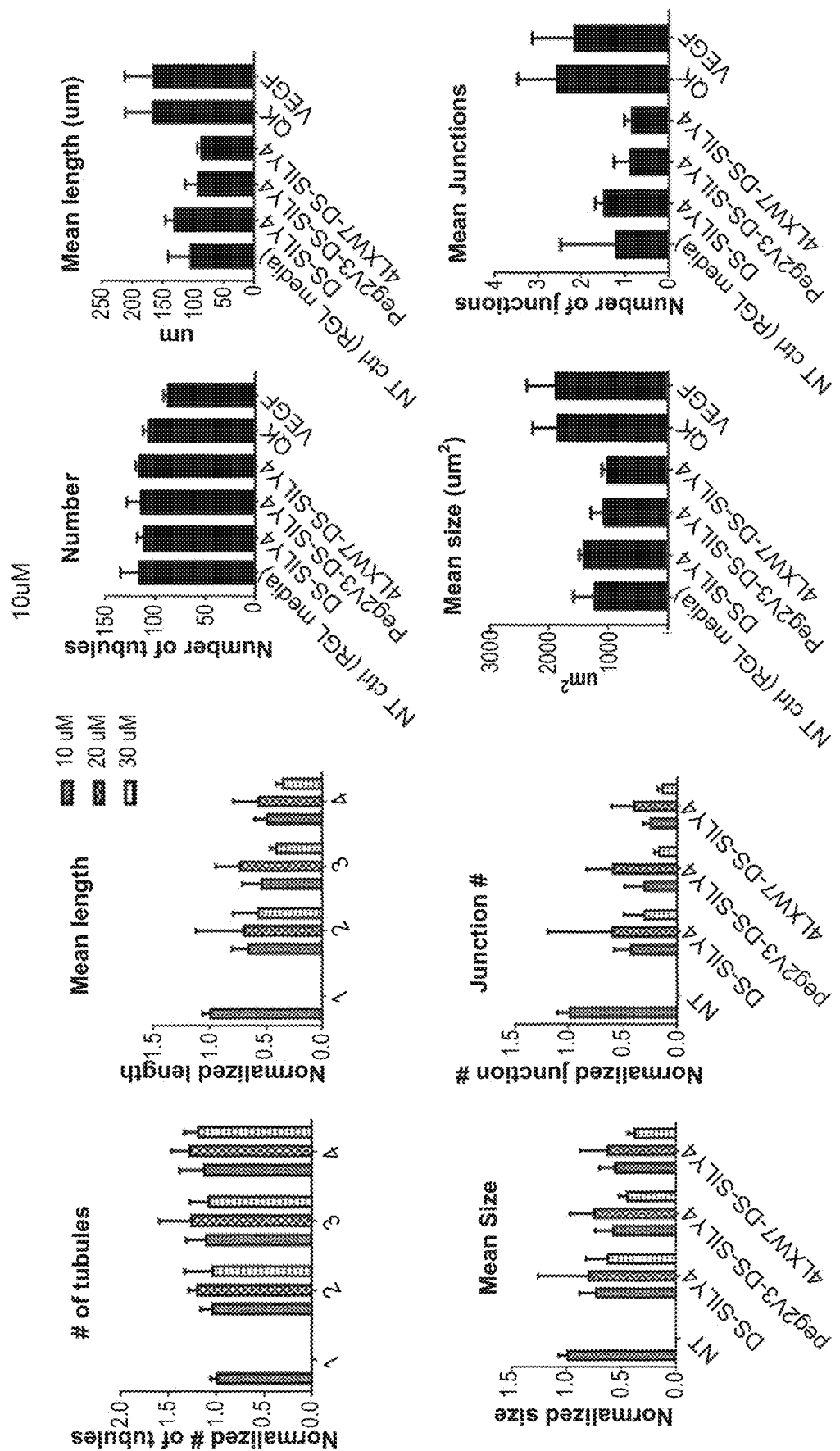
FIG. 23 presents graphs of matrigel tubulogenesis assay results using 10 µM treatments and untreated controls.
Figure 24:
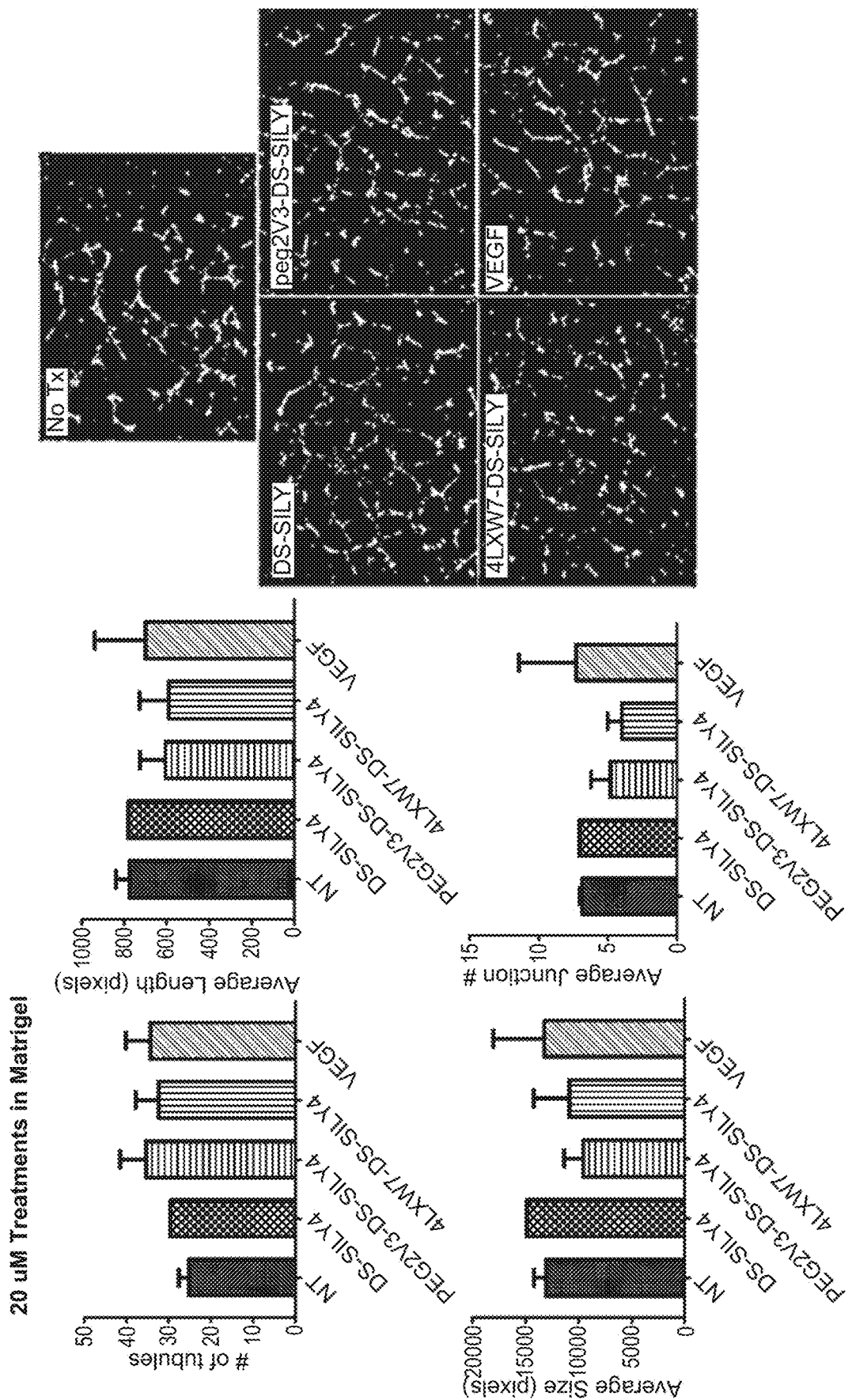
FIG. 24 presents graphs and images of matrigel tubulogenesis assay results using 20 µM treatments.

In vitro matrigel tubulogenesis assays revealed that treatments embedded within gels at a 10 µM concentration had no significant effects on HMVEC tubule number, length, size, or number of junctions compared to the untreated controls (FIG. 23). Increasing the embedded treatment concentration to 20 µM resulted in increased tubule number but trending decreases in length, size, and junction number (FIG. 24). Since this assay evaluates the responses of cells seeded on top of the gels, the data suggests that the 10 µM concentration may not present an adequate surface concentration to elicit a detectable response. Moreover while the rapid time course of the matrigel assay with tubules forming within a few hours and then destabilizing after 12 hours allows for quick screening of angiogenic factors, it may only reflect very acute cellular changes and their corresponding immediate effects on tubule formation. Nevertheless, it was clear from the matrigel assay that the vascular network formed differed in structure compared to untreated controls.

Figure 25:
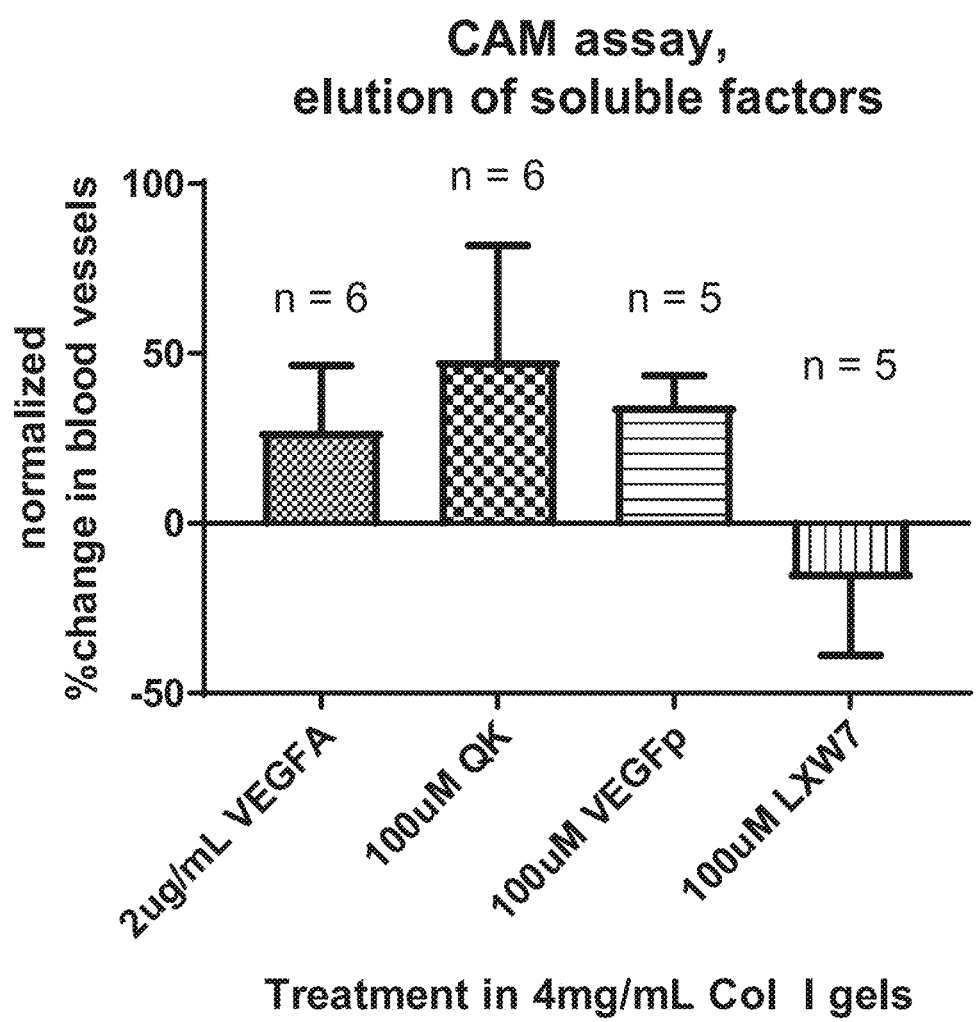
FIG. 25 presents a graph of chick chorioallantoic membrane vascularization in response to collagen gels with 100 µM peptides.

Example 32. Changes in Chick Chorioallantoic Membrane Vascularization in Response to Collagen Eels: Eluted Vs. Embedded Tethered Molecules FIG. 25 shows that 100 µM free VEGFp and QK peptides had comparable vasculogenic activity to each other and to 2 µg/mL VEGF-A, stimulating acute increases (30-50% compared to matched control gels on the same egg) in the number of blood vessels in a 2-mm radius surrounding implanted 10-mm diameter gels after 24 hours (n≥5). In contrast, elution of 100 µM LXW7 from collagen gels either decreased or caused no changes in surrounding vessel growth after 24 hours (FIG. 25 shows a decrease that is not statistically significant). The lack of increased vascularity in response to free LXW7 seen here suggests that the LXW7 peptide needs to be surface-bound to promote angiogenesis.

Figure 26:
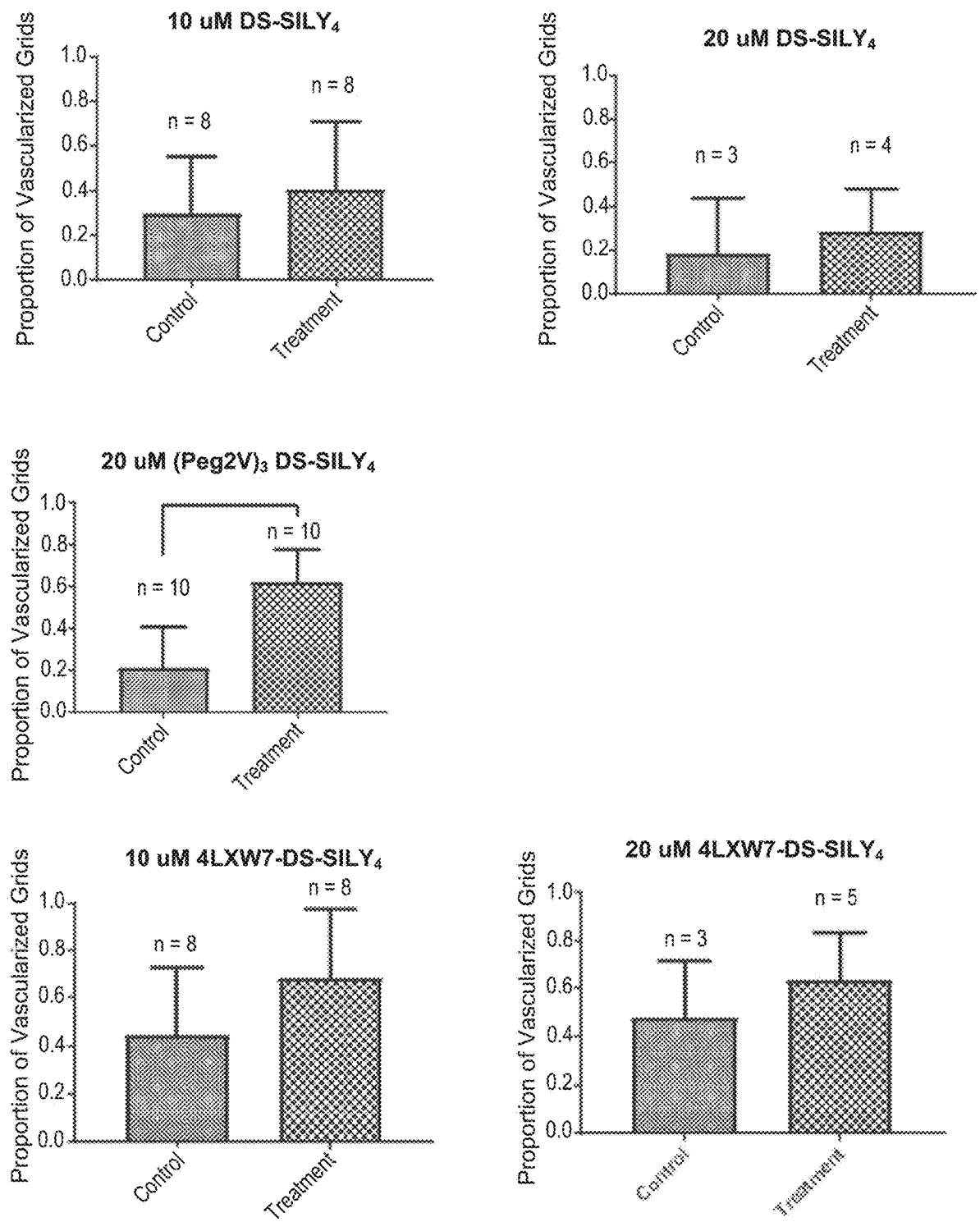
FIG. 26 presents graphs of chick chorioallantoic membrane vascularization in response to collagen gels with 10 µM or 20 µM peptides.
Figure 27:
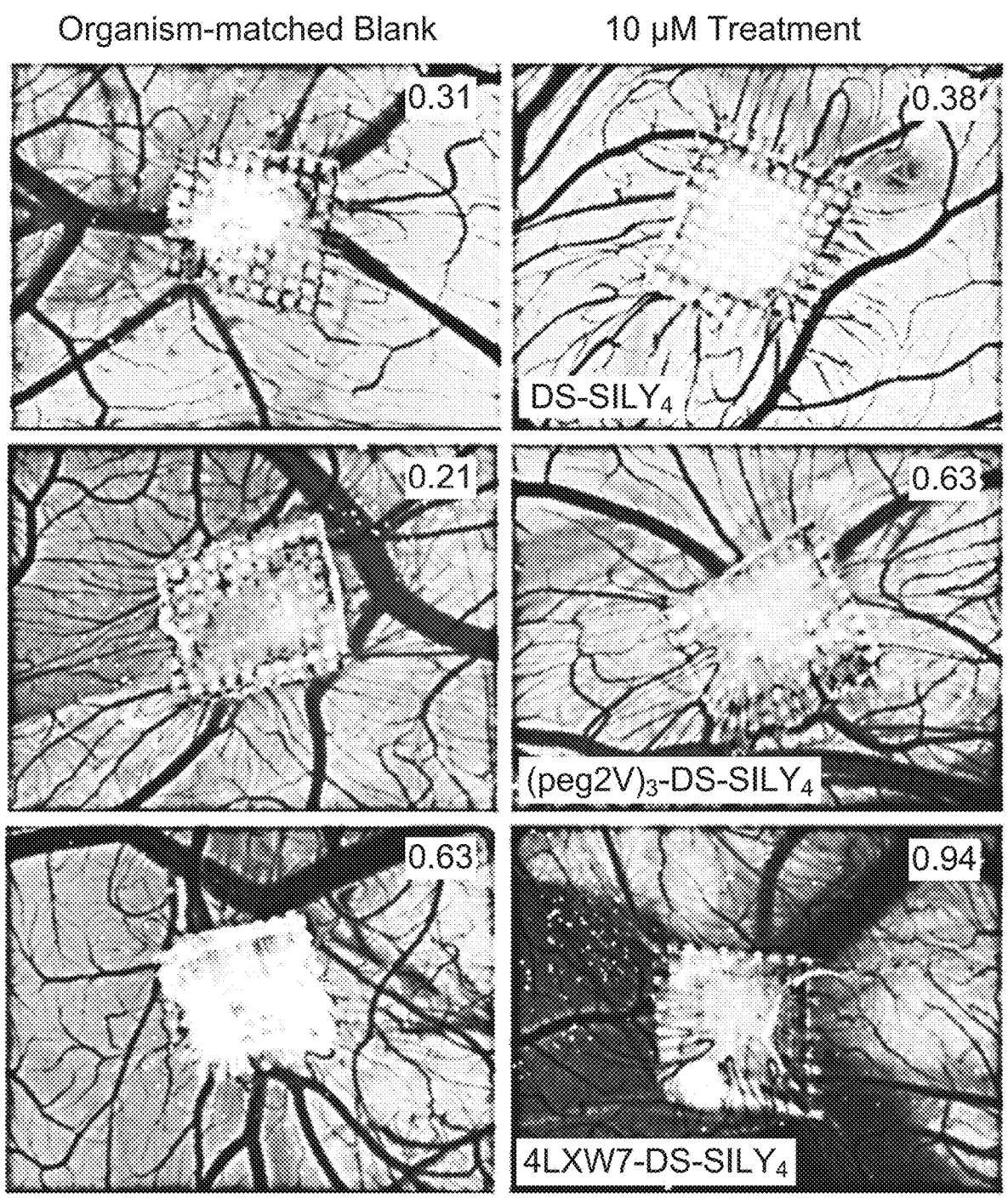
FIG. 27 presents images of representative vascularized gels.

Both 10 µM and 20 µM DS-SILY$_4$ showed a very slight increase in gel vascularity that was not statistically significant over the blank controls (FIGS. 26A and 26B). However, FIG. 26C demonstrates that 10 µM gel-embedded (peg2V)$_3$-DS-SILY$_4$ significantly increased the vascularized area within the gel compared to matched blank controls by day 4 after implantation. As can be seen in the representative vascularized gel images (FIG. 27), new vessels invaded the collagen gels in a radial fashion with many vessels going towards and then away from the center of the transplanted gel. Under high magnification through a stereoscope, rapidly flowing red blood cells were apparent within the invading capillaries with directional flow indicative of the presence of both new arterioles and venules. Since 10 µM (peg2V)$_3$-DS-SILY$_4$ already showed a significantly improved vascular response, the 20 µM concentration was not investigated.

Both 10 µM and 20 µM 4LXW7-DS-SILY$_4$ embedded gels caused a large increase in vascularized gel area, but not statistically significant than the organism-matched blank controls (FIGS. 26D and 26E). In fact, 10 µM and 20 µM 4LXW7-DS-SILY$_4$ treatments produced almost identical gel vascularization results. Interestingly, the proportion of vascularized gel area in 4LXW7-DS-SILY$_4$ treated gels was similar to that seen for (peg2V)$_3$-DS-SILY$_4$ treated gels, but the organism-matched blank controls exhibited an trending increase in vascularity compared to blank controls on eggs treated with DS-SILY$_4$ and (peg2V)$_3$-DS-SILY$_4$. Since the increase in the blank controls was not present in the DS-SILY$_4$ or (peg2V)$_3$-DS-SILY$_4$ treated eggs, it is more likely that this unexpected increase in the blank control gels results from an induced a systemic response perhaps by release of angiogenic factors into the blood circulation rather than 4LXW7-DS-SILY$_4$ releasing from the collagen gel.

In an attempt to better visualize new vasculature invading the implanted collagen gels, we injected ~100 µL 1 mg/mL high molecular weight fluorescent dextran (70 kDa RITC-dextran) into the CAM vessels 7 days after transplantation, cut out integrated collagen gels and surrounding membrane, and imaged with fluorescence microscopy. For proof-of-concept, control CAMs without transplanted gels were injected and imaged with this method and demonstrated that the fluorescent dextran reasonably represented the vasculature without leaking outside the vessels (FIG. 28A). In our studies, both treatment and blank collagen gels showed diffuse red fluorescence in all eggs (FIG. 28B). This fluorescent signal was not present in blank collagen gels not exposed to RITC-dextran (data not shown). Since all the collagen gels exhibited some degree of leakiness measured by the RITC-dextran fluorescence, it is difficult to infer the permeability effects of the collagen-bound treatment molecules. Injection of 100 µL of a 2% w/v Evans blue in PBS for better visualization of extravasate suggested that while all the collagen gels had some accumulation of the blue dye, the (peg2V)$_3$-DS-SILY$_4$ gels looked darker indicating increased vascular permeability in surrounding vessels.

Example 33. Effects of Soluble VEGF-Mimicking Molecules on HMVEC Monolayer Permeability (Transwell)

Figure 29:
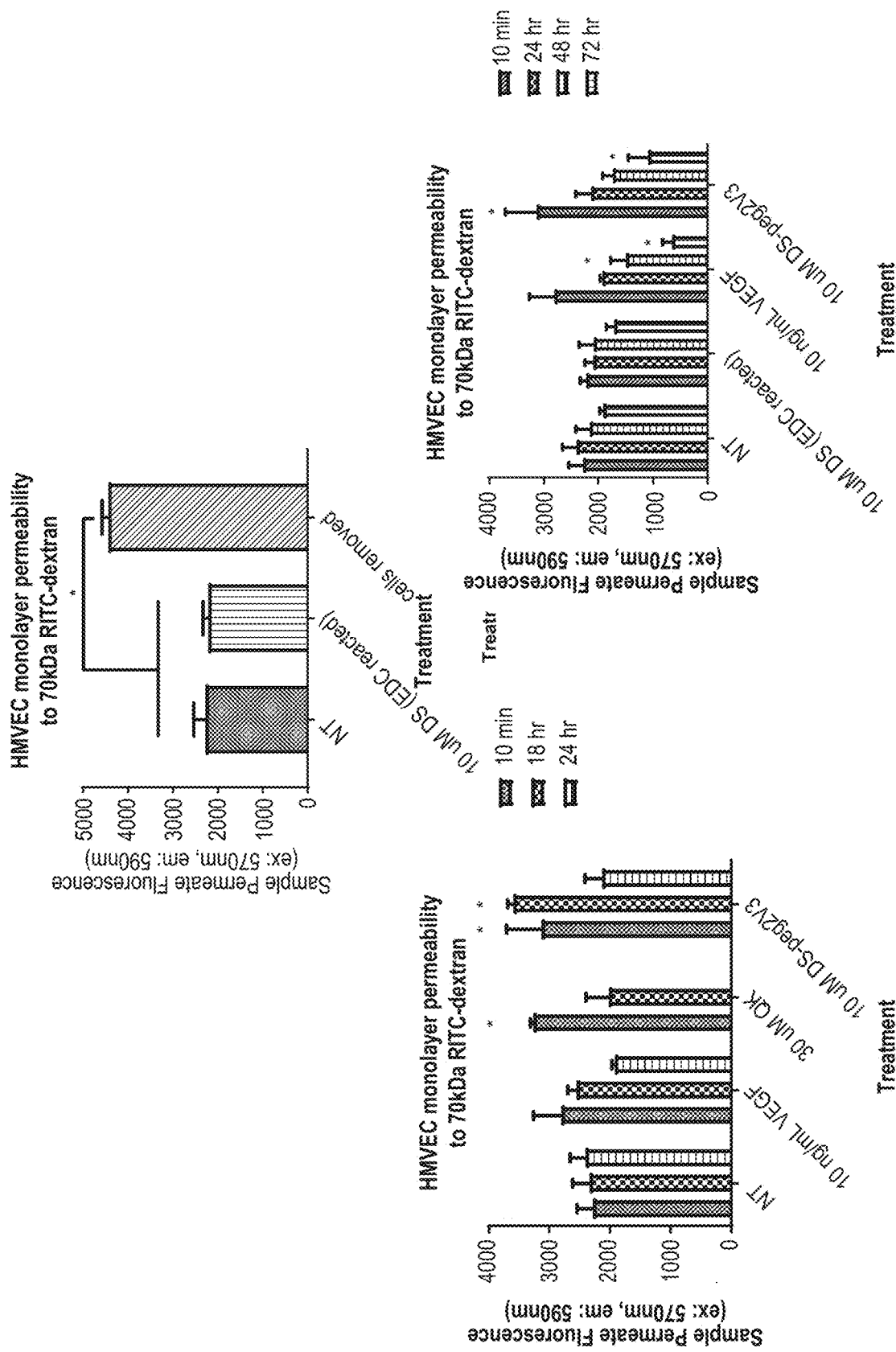
FIG. 29 presents graphs of the effects of peptides on endothelial permeability.

Given that the CAM assay suggested that the tested molecules may be altering vascular permeability and that VEGF is also known as vascular permeability factor and is hence widely known to increase vascular permeability, we were interested in the effects of VEGF-mimicking peptides on endothelial permeability in comparison to VEGF. We therefore followed treatments after 10 minutes through 3 days, although it is worth noting that our experimental method effectively investigated permeability effects after a series of repeated bolus treatments of soluble molecules on a HMVEC monolayer. The transwell results in FIG. 29A demonstrate that the seeded HMVECs indeed formed a monolayer significantly decreasing permeation of the 70 kDa RITC-dextran compared to wells with no cells, while FIGS. 29A and 29C indicate that EDC-reacted DS had no effects on permeability. FIG. 29B shows that as short as 10 minute incubation of 10 ng/mL VEGF, 30 µM QK, and 10 µM DS-(peg2V)$_3$ increased monolayer permeability compared to the non-treated media (EGM2-MV lacking VEGF) and 10 µM EDC-reacted DS, although only the QK and DS-(peg2V)$_3$ groups showed statistically significant increases in our experiment. After 18 hours, the increases in VEGF- and QK-induced permeability had disappeared, while DS-(peg2V)$_3$ still maintained significantly increased permeability (FIG. 29B). By 24 hours, the permeability of DS-(peg2V)$_3$ treated wells recovered to control levels (FIG. 29B). By extending treatments out to 48 and 72 hours, both the VEGF and DS-(peg2V)$_3$ treatments actually showed trending decreases in monolayer permeability (FIG. 29C). Both VEGF and DS-(peg2V)$_3$ were significantly different from untreated controls by 72 hours, and the effect of 10 µM DS-(peg2V)$_3$ was statistically equivalent to 10 ng/mL VEGF (FIG. 29C).

Example 34. Additional Supporting Data

Figure 30:
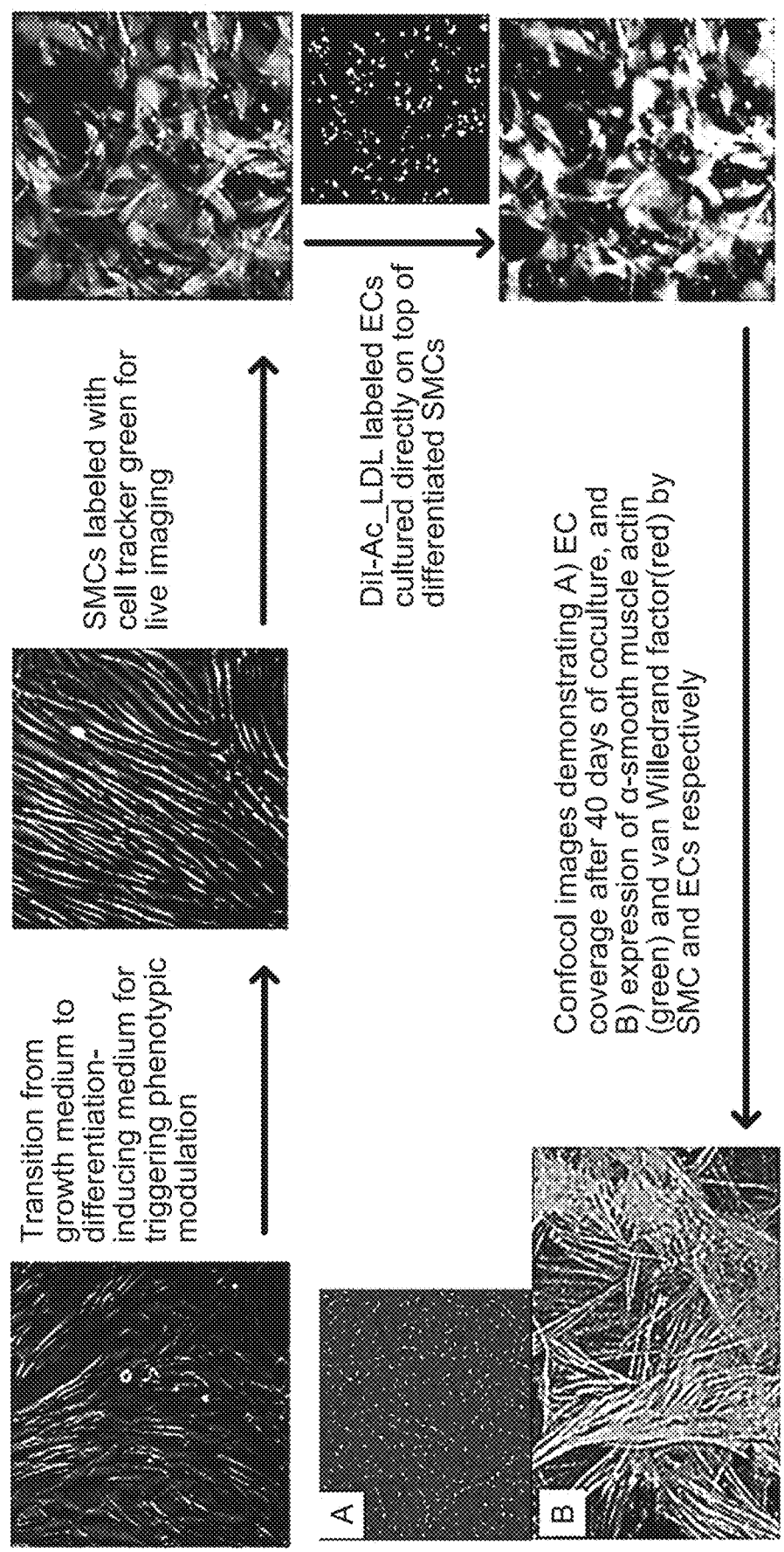
FIG. 30. EC-SMC co-culture system for evaluation of therapeutics. SMCs were tracked via CellTracker™ Green CMFDA and ECs were tracked by specifically labeling them with DiI-Ac-LDL. In image B SMCs are labeled with α-SMA (Green) and ECs are labeled with vWF (red).

Data have demonstrated that arterial mimics can be developed in the laboratory using human SMCs alone or with ECs. With the appropriate culture media components, the tissue cultured mimics can be induced to behave as the healthy or diseased arterial state. An important finding from our study is that quiescent (or contractile) SMCs support adhesion of a monolayer of ECs, while the proliferative (or hyperplastic) SMCs do not support the same EC monolayer. This unique culture system provides the opportunity to optimize the design of our therapies to prevent platelet binding to the damaged vessel wall and/or support EPC capture and monolayer formation on the medial mimetics as the mimetics can be made to behave as denuded diseased vessels or as recently denuded healthy vessel. The cultures can be maintained for over one month and can serve as a high throughput method for testing various densities of peptide grafted to the DS and multiple therapeutic concentrations. A model is shown pictorially in FIG. 30.

The antithrombotic proteoglycan mimetic, DS-SILY, binds to collagen with high affinity, such that it remains bound during blood flow, and prevents collagen-induced platelet activation in vitro. Platelet binding and activation on a collagen surface was inhibited up to nearly 90% with DS-SILY treatment. Further, DS-SILY was found to promote EC migration up to 32% compared to control collagen surfaces, presumably through its DS backbone, which can bind to and activate resident FGF-2 and FGF-10. Therefore, DS-SILY blocks platelet binding and supports EC growth, resulting in faster vessel healing.

An In vivo Ossabaw pig angioplasty model was used to assess platelet deposition (acute) and neointimal hyperplasia (1-month recovery) with DS-SILY treatment. Porous angioplasty balloons were employed for delivery of soluble DS-SILY to the target arteries in the peripheral vasculature of pigs. Renal, femoral, and iliac arteries were denuded by balloon expansion, followed by delivery through the porous balloon. Arteries were treated with and without the use of a bare metal stent and the healing response was assessed for neointimal hyperplasia.

Arteries for assessing the acute response of balloon injury were harvested within hours of angioplasty. The arteries were rinsed with saline and fixed in 10% formalin overnight, and prepared for SEM visualization. FIG. 31 shows that platelets are scarcely found on the denuded artery in DS-SILY treatment, compared to significant platelet coverage of the artery wall in sham (saline) control treated arteries. High magnification images in FIG. 31 show numerous projections and spreading of platelets on sham control arteries, indicative of platelet activation. In contrast, when platelets were found present on the DS-SILY treated artery, they remained largely rounded. These results indicate that DS-SILY binds to the exposed collagen of the vessel wall and prevents platelet binding and activation, the first steps that lead to thrombosis and intimal hyperplasia.

Neointimal hyperplasia was assessed by histology after 1-month recovery by measuring the distance between the internal elastic lamina and the lumen, or between a stent post and the lumen (FIG. 32). Neointimal hyperplasia is observed with and without stents in sham controls, whereas minimal intimal hyperplasia is observed in DS-SILY treated arteries. With respect to DS-SILY, these data show that it suppresses SMC migration and proliferation, two hallmarks of neointimal hyperplasia. Also, DS-SILY suppresses inflammatory cytokine production, a second hallmark in intimal hyperplasia. DS-SILY also suppresses, but does not eliminate protein production by SMCs. In vivo data (FIG. 32) shows that DS-SILY suppresses platelet binding to denuded blood vessels and inhibits intimal hyperplasia at 4 weeks as compared to untreated vessels.

Using primary artery-derived ECs and blood-derived EPCs as living probes to screen One-Bead-One-Compound (OBOC) combinatorial peptide libraries, several high-affinity binding ligands against the αvβ3 integrin on the surface of EPCs/ECs were identified. One of these peptides, LXW7, a cyclic octapeptide (cyclic cGRGDdvc), was found to bind strongly to primary EPCs/ECs, but weakly to platelets and does not bind to THP-1 monocytes. The LXW7 peptide, when grafted to surfaces, supports adhesion and spreading of EPCs and human coronary ECs, but not platelets or monocytes. Culture plates, 24-well, were coated with 500 µL of 20 µg/mL Avidin for 1 hour at 37° C. followed by washing with PBS and coating with either 500 µL molar equivalents of D-biotin, LXW7-biotin, or GRGD-biotin. After washing with PBS and blocking with 1% BSA wells were ready for cell attachment with $5 \times 10^4$ HCAECs or THP-1 monocytes suspended in the respective maintenance medium, or freshly isolated platelets at a density of $5 \times 10^7$ platelets/cm2 incubated for 16 h at 37° C., 5% CO2. The cells were washed with PBS, and fixed in 10% formalin for 20 min. For evaluation of HCAEC, the cells were blocked with 1% BSA and incubated overnight with mouse anti-CD31 antibody (1:100; Abcam) in 1% BSA at 4° C., followed by probing with goat anti-mouse Alexa Fluor 594 conjugate in 1% BSA. Nuclei were stained with DAPI.

Images were captured using an Olympus IX81 microscope. Phase contrast images were taken for evaluation of THP-1 monocyte and platelet attachment. Quantification of images was performed using the Image J software (NIH). Representative images are shown in FIG. 33A, and quantification is shown in FIG. 33B. LXW7 peptide supported robust HCAEC binding, but not monocyte or platelet binding, while the RGD peptide generally supported monocyte and platelet binding.

Figure 34:
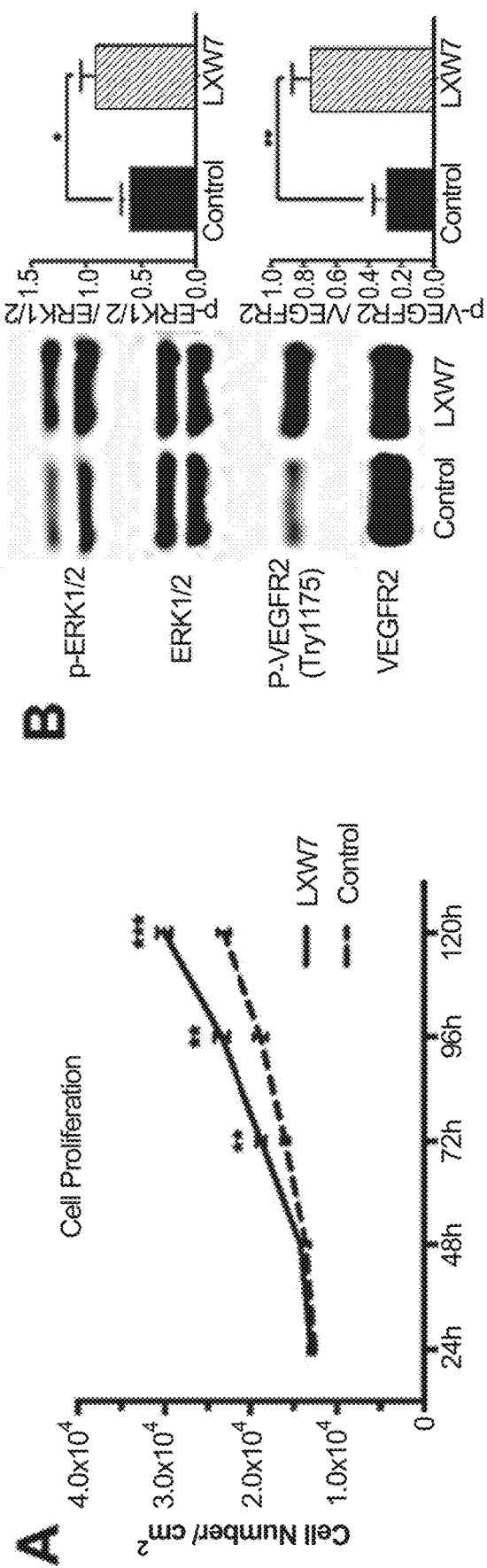
FIG. 34. Effects of LXW7 on EC biological functions. (A) Proliferation of ECs on LXW7-treated surfaces and D-biotin treated surface (control) assessed by MTS assay. Data were expressed as mean±standard deviation: $p<0.01$, *$p<0.001$ (n=4). (B) Western-blot analysis of the effect of LXW7 on phosphorylation of VEGFR2 (Tyr1175) and phosphorylation of ERK1/2 (left panels) and quantified by densitometry (right panels). Data were expressed as mean±standard deviation: *$p<0.05$, **$p<0.01$ (n=4).
Figure 35:
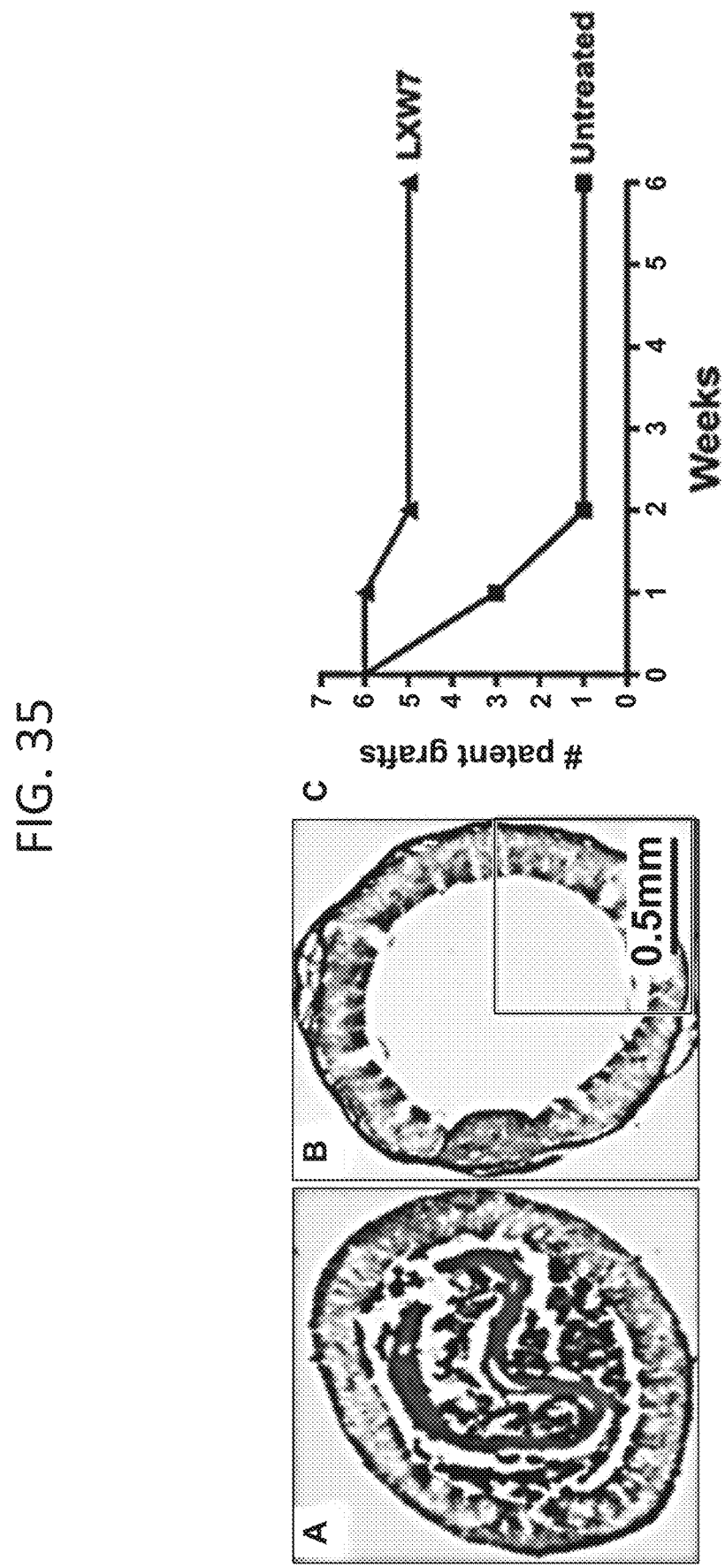
FIG. 35. Patency study of LXW7 conjugation on the luminal surface of small diameter vascular grafts increased endothelialization of the in a rat carotid artery bypass model. Representative images of (A) thrombosed (control grafts without LXW7 modification) and (B) patent grafts (LXW7-modified) at 6 weeks. Temporal patency analysis (C) showed that LXW-modified grafts maintained significant higher patency rate than the unmodified control grafts.

To further probe the effects EC and EPC binding to surface-grafted LXW7, in vitro studies were performed to investigate ERK1/2 and VEGF receptor phosphorylation as both are downstream markers of EC binding through the $\alpha_v\beta_3$. LXW7 stimulated cell proliferation (FIG. 34A) and phosphorylation of ERK ½ and VEGF2 receptor (FIG. 34B), as expected due to adhesion via the $\alpha_v\beta3$ integrin and further suggests the specificity of LXW7. To test the ability of LXW7 to promote endothelialization, we evaluated polymer-based small diameter vascular grafts (ID 1 mm) functionalized with LXW7 via Click chemistry in a rat carotid artery bypass model (FIG. 35). We found that LXW7-modified grafts showed significantly higher patency rate than the control grafts. After 6 weeks post implantation, 5 out of 6 LXW7-modified grafts were patent versus only 1 out of 6 control grafts was patent (FIG. 35). In addition, mature ECs were present throughout the whole length of the LXW7-modified grafts while only a limited number of ECs were identified in the middle segment of the control grafts. This confirms that LXW7 coating on the luminal surface of synthetic vascular grafts can generate a "living" endothelium.

Although the foregoing disclosure has been described in some detail by way of illustration and example for purpose of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound comprising:
one or more P1 subunits, wherein P1 is a synthetic peptide comprising an amino acid sequence that comprises a collagen-binding domain having the amino acid sequence RRANAALKAGELYKSILY (SEQ ID NO: 1) or a conservatively modified variant sequence having at least 80% sequence identity with the amino acid sequence RRANAALKAGELYKSILY (SEQ ID NO: 1);

one or more P2 subunits, wherein P2 is a synthetic peptide comprising an amino acid sequence that comprises an integrin-binding domain, and wherein P2 is selected from the group consisting of cGRGDdvc (LXW7), cGRGDsfc, cGRGDdfc, cGRGDsec, cGRGDdsc, cGRGDd-DBug-c, cGRGDd-DBta-c, Ac-cGRGDdvc, (β-alanine)-cGRGDdvc, (Ebes)-cGRGDdvc, cGRGDd-DAgl-c, cGRGDd-DPra-c, cGRGDd-D(NMe)Val-c, cGRGDd-D(CαMe)Val-c, cGRGDd-DAbu-c, cGRGDd-DNal1-c, cGRGDd-DNal2-c, and peg2V; and a glycan, wherein each P1 subunit and each P2 subunit is linked to the glycan.

2. The compound of claim 1, wherein P1 is a synthetic peptide comprising the amino acid sequence RRANAALKAGELYKSILY (SEQ ID NO: 1).

3. The compound of claim 1, wherein P1 is a synthetic peptide of up to 40 amino acids comprising the amino acid sequence RRANAALKAGELYKSILY (SEQ ID NO: 1).

4. The compound of claim 1, wherein P2 is a synthetic peptide comprising an amino acid sequence that comprises an αvβ3-binding domain.

5. The compound of claim 1, wherein P2 is LXW7.

6. The compound of claim 1, wherein P2 is peg2V.

7. The compound of claim 1, wherein the glycan is a glycosaminoglycan or polysaccharide.

8. The compound of claim 7, wherein the glycan is selected from the group consisting of alginate, agarose, dextran, chondroitin, dermatan, dermatan sulfate, heparan, heparin, keratin, and hyaluronan.

9. The compound of claim 8, wherein the glycan is selected from the group consisting of dermatan sulfate, dextran, and heparin.

10. A compound comprising:
one or more P1 subunits, wherein P1 is a synthetic peptide comprising an amino acid sequence that comprises a collagen-binding domain having the amino acid sequence RRANAALKAGELYKSILY (SEQ ID NO: 1) or a conservatively modified variant sequence having at least 80% sequence identity with the amino acid sequence RRANAALKAGELYKSILY (SEQ ID NO: 1); and one or more P2 subunits, wherein P2 is a synthetic peptide comprising an amino acid sequence that comprises an integrin-binding domain, and wherein P2 is selected from the group consisting of cGRGDdvc (LXW7), cGRGDsfc, cGRGDdfc, cGRGDsec, cGRGDdsc, cGRGDd-DBug-c, cGRGDd-DBta-c, Ac-cGRGDdvc, (β-alanine)-cGRGDdvc, (Ebes)-cGRGDdvc, cGRGDd-DAgl-c, cGRGDd-DPra-c, cGRGDd-D(NMe)Val-c, cGRGDd-D(CαMe)Val-c, cGRGDd-DAbu-c, cGRGDd-DNal1-c, cGRGDd-DNal2-c, and peg2V.

11. The compound of claim 10, wherein P1 is a synthetic peptide comprising the amino acid sequence RRANAALKAGELYKSILY (SEQ ID NO: 1).

12. The compound of claim 10, wherein P1 is a synthetic peptide of up to 40 amino acids comprising the amino acid sequence RRANAALKAGELYKSILY (SEQ ID NO: 1).

13. The compound of claim 10, wherein P2 is a synthetic peptide comprising an amino acid sequence that comprises an αvβ3-binding domain.

14. The compound of claim 10, wherein P2 is LXW7.

15. A composition comprising the compound of claim 1 and one or more pharmaceutically acceptable excipients, diluents, or a combination thereof.

16. A method for improving endothelialization and vascularization of endothelial cells and/or endothelial progenitor cells in a subject, the method comprising administering to the subject a composition comprising the compound of claim 1.

17. The method of claim 16, wherein the composition comprises one or more pharmaceutically acceptable excipients, diluents, or a combination thereof.

* * * * *